US009668998B2

(12) United States Patent
Bodmeier et al.

(10) Patent No.: US 9,668,998 B2
(45) Date of Patent: Jun. 6, 2017

(54) SOLID MOLECULAR DISPERSION OF FESOTERODINE HYDROGEN FUMARATE AND POLYMERIC BINDER

(75) Inventors: Roland Bodmeier, Berlin (DE); Alan Francis Carmody, Sandwich (GB); Mesut Ciper, Berlin (DE); Anne Therese Gustaaf De Paepe, Sandwich (GB); John Mark Heimlich, Sandwich (GB); Martin Korber, Berlin (DE); Mathias Walther, Sandwich (GB); Neil Feeder, Sandwich (GB)

(73) Assignee: Pfizer Limited, Sandwich, Kent (GB)

( * ) Notice: Subject to any disclaimer, the term of this patent is extended or adjusted under 35 U.S.C. 154(b) by 433 days.

(21) Appl. No.: 13/978,887

(22) PCT Filed: Jan. 17, 2012

(86) PCT No.: PCT/IB2012/050225
§ 371 (c)(1),
(2), (4) Date: Jul. 10, 2013

(87) PCT Pub. No.: WO2012/098499
PCT Pub. Date: Jul. 26, 2012

(65) Prior Publication Data
US 2013/0287847 A1 Oct. 31, 2013

Related U.S. Application Data

(60) Provisional application No. 61/433,743, filed on Jan. 18, 2011.

(51) Int. Cl.
A61K 31/222 (2006.01)
A61K 31/22 (2006.01)
A61K 47/38 (2006.01)
A61K 9/10 (2006.01)
A61K 9/14 (2006.01)
A61K 9/16 (2006.01)
A61K 9/20 (2006.01)
A61K 9/50 (2006.01)
A61K 9/08 (2006.01)

(52) U.S. Cl.
CPC .............. A61K 31/222 (2013.01); A61K 9/08 (2013.01); A61K 9/10 (2013.01); A61K 9/146 (2013.01); A61K 9/1652 (2013.01); A61K 9/1676 (2013.01); A61K 9/1694 (2013.01); A61K 9/2054 (2013.01); A61K 9/5078 (2013.01); A61K 31/22 (2013.01); A61K 47/38 (2013.01)

(58) Field of Classification Search
CPC ........ A61K 9/10; A61K 9/146; A61K 9/1652; A61K 9/1676; A61K 9/1694; A61K 9/2054; A61K 9/5078; A61K 31/22; A61K 31/222; A61K 47/38
See application file for complete search history.

(56) References Cited

U.S. PATENT DOCUMENTS

| 5,382,600 | A | 1/1995 | Jonsson et al. | |
| 6,858,650 | B1 | 2/2005 | Meese | |
| 7,384,980 | B2 | 6/2008 | Meese et al. | |
| 2003/0054037 | A1 | 3/2003 | Babcock et al. | |
| 2003/0185893 | A1* | 10/2003 | Beyerinck et al. | ........... 424/489 |
| 2007/0243252 | A1* | 10/2007 | Heinicke | .............. A61K 9/2866 424/468 |
| 2008/0138421 | A1* | 6/2008 | Arth et al. | .................... 424/489 |
| 2009/0088465 | A1 | 4/2009 | Dyar et al. | |
| 2013/0287847 | A1 | 10/2013 | Bodmeier et al. | |

FOREIGN PATENT DOCUMENTS

| EP | 0957073 | 11/1999 |
| WO | 9208459 | 5/1992 |
| WO | 9411337 | 5/1994 |
| WO | 0135957 | 5/2001 |
| WO | 03000238 | 1/2003 |
| WO | 2006059224 | 6/2006 |
| WO | 2007072169 | 6/2007 |
| WO | 2007141298 | 12/2007 |
| WO | 2008103914 | 8/2008 |
| WO | 2010043408 | 3/2010 |

OTHER PUBLICATIONS

Chiou, W.L., et al., "Pharmaceutical Applications of Solid Dispersion Systems", Journal of Pharmaceutical Sciences, Sep. 1971, pp. 1281-1302, 60(9).
Curatolo, William, et al., "Utility of Hydroxypropylmethylecellulose Acetate Succinate (HPMCAS) for Initiation and Maintenance of Drug Supersaturation in the GI Milieu", Pharmaceutical Research, Jun. 2009, pp. 1419-1431, 26(6).
Fukumori, Y., et al., "Fluid Bed Processes for Forming Functional Particles", Encyclopedia of Pharmaceutical Technology, Oct. 2006, pp. 1773-1778, Chapter 125 1(1).
Konno, et al., "Influence of Different Polymers on the Crystallization Tendency of Molecularly Dispersed Amorphous Felodipine", Journal of Pharmaceutical Science, Dec. 2006, pp. 2692-2705, 95(12).
Kennedy, Michael, et al., "Enhanced Bioavailability of a Poorly Soluble VR1 Antagonist Using an Amorphous Solid Dispersion Approach: A Case Study", Molecular Pharmaceutics, Dec. 1, 2008, pp. 981-993, 5(6).
Feng, Qain, et al., "Drug-polymer Solubility and Miscibility: Stability Consideration and Practical Challenges in Amorphous Solid Dispersion Development", Journal of Pharmaceutical Sciences, Jan. 1, 2010, pp. 2941-2947.
International Search Report of PCT Application No. PCT/IB2012/050255, filed Jan. 17, 2012, 5 pages, mailed Apr. 20, 2012.
PCT Written Opinion of the International Searching Authority of PCT Application No. PCT/IB2012/050255, filed Jan. 17, 2012, 7 pages, mailed Apr. 20, 2012.

(Continued)

Primary Examiner — Michael B Pallay
(74) Attorney, Agent, or Firm — Richard V. Zanzalari

(57) ABSTRACT

The present invention relates to a solid molecular dispersion of from 3:97 to 12:88 weight % ratio of fesoterodine hydrogen fumarate and a polymeric binder selected from the group consisting of an alkyl hydroxyalkylcellulose ether, a hydroxyalkylcellulose ether, an ester of either thereof, and a mixture of any two or more thereof.

34 Claims, 19 Drawing Sheets

(56) References Cited

OTHER PUBLICATIONS

WO2001/035957 Machine Translation.
WO2010/043408 Machine Translation.
Janssens, Sandrien, et al., "Review: physical chemistry of solid dispersions", Journal of Pharmacy and Pharmacology, 2009, pp. 1571-1586, 61(12).
Kothari, Khushboo, et al, "The Role of Drug-Polymer Hydrogen Bonding Interactions on the Molecular Mobility and Physical Stability of Nifedipine Solid Dispersions", Molecular Pharmaceutics, 2015, pp. 162-170, vol. 12.
Kuo, Shiao Wei, et al, "Study of Hydrogen-Bonding Strength in Poly(e-caprolactone)Blends by DSC and FTIR", Journal of Polymer Science: Part B: Polymer Physics, 2001, pp. 1348-1359, vol. 39.
Ditropan XL Prescribing Information, Revised Jul. 2013. (Petition Paper 20, Exhibit 2036).
Baigrie, R.J., et al., "Oxybutynin: is it Safe?", British Journal of Urology, 1988, pp. 319-322, vol. 62. (Petition Paper 20, Exhibit 2037).
Madersbacher, H., et al., "A Urodynamically Controlled Multicenter Study in Patients with Urge Incontinence: Tolerability and Efficacy of Propiverine Hydrochloride in Comparison to Oxybutynin", Abstract 187, Sep. 1993. (Petition Paper 20, Exhibit 2038).
Miyachi, Hiroyuki, et al., "Novel Imidazole Derivatives with Subtype-Selective Antimuscarinic Activity (2)", Bioorganic & Med. Chemistry Letters, 1998, pp. 2163-2168, vol. 8. (Petition Paper 20, Exhibit 2039).
Nilvebrant, Lisbeth, "Clinical Experiences with Tolterodine", Life Sciences, 2001, pp. 2549-2556, vol. 68. (Petition Paper 20, Exhibit 2040).
Smith, Carolyn M., et al., "Characterization of [3H]-Darifenacin As A Novel Radioligand For The Study of Muscarinic M3 Receptors", Journal of Receptor & Signal Transduction Research, 1997, pp. 177-184, 17(1-3). (Petition Paper 20, Exhibit 2041).
Andersson, Karl-Erk, "The Overactive Bladder: Pharmacologic Basis of Drug Treatment", Urology, Dec. 1997, pp. 74-84, 50(Supplement 6A). (Petition Paper 20, Exhibit 2042).
Taniguchi, Kiyoshi, et al., "Agents for the Treatment of Overactive Detrusor. IX. Synthesis and Pharmacological Properties of Metabolites of N-tert-Butyl-4, 4-diphenyl-2-cyclopentenylamine (FK584) in Human Urine", Chem. Pharm. Bull., 1996, pp. 1188-1195, 44(6). (Petition Paper 20, Exhibit 2043).
Sasaki, Yasuo, et al., "Effect of NS-21, an Anticholinergic Drug with Calcium Antagonistic Activity, on Lower Urinary Tract Function in a Rat Model of Urinary Frequency", International Journal Urology, 1997, pp. 401-406, vol. 4. (Petition Japer 20, Exhibit 2044).
Kikukawa, Hiroaki, et al., "Pharmacologic Actions of Temiverine (p-INN) and its Active Metabolite, Rcc-36, on Isolated Human Urinary Bladder Muscle", International Journal of Urology, 1998, pp. 268-275, vol. 5. (Petition Paper 20, Exhibit 2045).
Mealy, N., et al., "YM-905 Treatment of Urinary Incontinence Muscarinic M3 Antagonist", Drugs of the Furture, 1999, pp. 871-874, 24(8). (Petition Paper 20, Exhibit 2046).
Balant, L.P. et al., "Prodrugs for the Imporvement of Drug Absorption via Different Routes of Administration" European Journal of Drug Metabolism and Pharmacokinetics, 1990, pp. 143-153, 15(2). (Petition Paper 20, Exhibit 2047).
Beaumont, Kevin, et al., "Design of Ester Prodrugs to Enhance Oral Absorption of Poorly Permeable Compounds: Challenges to the Discovery Scientist", Current Drug Metabolism, 2003, pp. 461-485, vol. 4. (Petition Paper 20, Exhibit 2048).
Stella, Valentino J., "Prodrugs and Site-Specific Drug Delivery" Journal of Medicinal Chemistry, Dec. 1980, pp. 1275-1282, 23(12). (Petition Paper 20, Exhibit 2049).
Ettmayer, Peter, et al., "Lesson Learned from Marketed and Investigational Prodrugs", Journal of Medicinal Chemistry, 2004, pp. 2393-2404, 47(10). (Petition Paper 20, Exhibit 2050).
Roth, Bruce D., et al., "Relationship between Tissue Selectivity and Lipophilicity for Inhibitors of HMG-CoA Reductase" Journal of Medicinal Chemistry, 1991, pp. 463-466, vol. 34. (Petition Paper 20, Exhibit 2051).
Magyar, János, et al. "Effects of Norfluoxetine on the Action Potential and Transmembrane Ion Currents in Canine Ventricular Cardiomyocytes", Naunyn-Schmiedeberg's Arch. Pharmacol, 2004, pp. 203-210, vol. 370. (Petition Paper 20, Exhibit 2052).
Prescribing Information for Accupril (Quinapril Hydrochloride Tablets) retrieved Mar. 10, 2015. (Petition Paper 20, Exhibit 2054).
Narurkar, Milind M., et al., "Synthesis, Physicochemical Properties, and Cytotoxicity of a Series of 5'-Ester Prodrugs of 5-Iodo-2'-Deoxyuridine", Pharmaceutical Research, 1988-pp. 734-737, 5(11). (Petition Paper 20, Exhibit 2055).
Hartung, Thomas, "For for Thought Look Back in Anger—What Clinical Studies Tell Us About Preclinical Work", Nature, 1984, pp. 275-291, vol. 312. (Petition Paper 20, Exhibit 2056).
Chart of FDA Approvals of New Drug Applications (NDAs) for New Molecular Entities and New Active Ingredients Jan. 1994-Dec. 1998. (Petition Paper 20, Exhibit 2057).
Sitar, Daniel S., "Clinical Pharmacokinetics of Bambuterol", Clinical Pharmacokinet, Oct. 1996, pp. 246-256, 31(4). (Petition Paper 20, Exhibit 2058).
Balant, L.P. et al., "Prodrugs for the Imporvement of Drug Absorption via Different Routes of Administration" European Journal of Drug Metabolism and Pharmacokinetics, 1990, pp. 143-153, 15(2). (Petition Paper 17, Exhibit 2047).
Beaumont, Kevin, et al., "Design of Ester Prodrugs to Enhance Oral Absorption of Poorly Permeable Compounds: Challenges to the Discovery Scientist", Current Drug Metabolism, 2003, pp. 461-485, vol. 4. (Petition Paper 17, Exhibit 2048).
Stella, Valentino J., "Prodrugs and Site-Specific Drug Delivery" Journal of Medicinal Chemistry, Dec. 1980, pp. 1275-1282, 23(12). (Petition Paper 17, Exhibit 2049).
Ettmayer, Peter, et al., "Lesson Learned from Marketed and Investigational Prodrugs", Journal of Medicinal Chemistry, 2004, pp. 2393-2404, 47(10). (Petition Paper 17, Exhibit 2050).
Roth, Bruce D., et al., "Relationship between Tissue Selectivity and Lipophilicity for Inhibitors of HMG-CoA Reductase" Journal of Medicinal Chemistry, 1991, pp. 463-466, vol. 34. (Petition Paper 17, Exhibit 2051).
Magyar, János, et al. "Effects of Norfluoxetine on the Action Potential and Transmembrane Ion Currents in Canine Ventricular Cardiomyocytes", Naunyn-Schmiedeberg's Arch. Pharmacol, 2004, pp. 203-210, vol. 370. (Petition Paper 17, Exhibit 2052).
Prescribing Information for Accupril (Quinapril Hydrochloride Tablets) retrieved Mar. 10, 2015. (Petition Paper 17, Exhibit 2054).
Narurkar, Milind M., et al., "Synthesis, Physicochemical Properties, and Cytotoxicity of a Series of 5'-Ester Jrodrugs of 5-Iodo-2'-Deoxyuridine", Pharmaceutical Research, 1988-pp. 734-737, 5(11). (Petition Paper 17, Exhibit 2055).
Hartung, Thomas, "For for Thought Look Back in Anger—What Clinical Studies Tell Us About Preclinical Work", Nature, 1984, pp. 275-291, vol. 312. (Petition Paper 17 Exhibit 2056).
Chart of FDA Approvals of New Drug Applications (NDAs) for New Molecular Entities and New Active Ingredients Jan. 1994-Dec. 1998. (Petition Paper 17, Exhibit 2057).
Sitar, Daniel S., "Clinical Pharmacokinetics of Bambuterol", Clinical Pharmacokinet, Oct. 1996, pp. 246-256, 31(4). (Petition Paper 17, Exhibit 2058).
Slatter, J.G., et al., "Bioactivation of the Anticancer Agent CPT-11 to SN-38 by Human Hepatic Micorsomal Carboxylesterases and the In Vitro Assessment of Potential Drug Interactions", Drug Metabolism and Disposition, 1997, pp. 1157-1164, 25(10). (Petition Paper 20, Exhibit 2059).
CV-Scott Avard MacDiarmid, M.D., FRCPSC. (Petition Paper 20, Exhibit 2060).
Abrams, Paul, et al., "The Standardisation of Terminology of Lower Urinary Tract Function: Report from the Standardisation Subcommittee of the International Continence Society", Neurourology and Urodynamics, 2002, pp. 167-178, vol. 21. (Petition Paper 20, Exhibit 2061).
Abrams, Paul, et al., "Incontinence", 5th International Consultation on Incontinence, Paris Feb. 2012, 5th Edition 2013. (Petition Paper 20, Exhibit 2062).

(56) References Cited

OTHER PUBLICATIONS

Abrams, Paul, et al., "Overactive Bladder Significantly Affects Quality of Life", Symposium Proceedings. The American Journal of Managed Care, Jul. 2000, pp. S580-S590. 6(11)Sup. (Petition Paper 20, Exhibit 2063).

Stewart, Walter F., et al., The prevalence and impact of overactive bladder in the U.S. : results from the NOBLE program, Neurourology and Urodynamics, 2001. (Petition Paper 20, Exhibit 2064).

Chapple, Christopher R., et al., "Tolterodine: Selectivity for the Urinary Bladder Over the Eye (as Measured by Visual Accommodation) in Healthy Volunteers", Drugs R&D, 2002, pp. 75-81, 3(2). (Petition Paper 20, Exhibit 2065).

Chapple, Christopher, et al., "The Effects of Antimuscarinic Treatments in Overactive Bladder: An Update of a Systematic Review and Meta-Analysis", European Urology, 2008, pp. 543-562, vol. 54. (Petition Paper 20, Exhibit 2066).

FDA, Drugs@FDS:Ditropan, https://www.accessdata.fda.gov/scripts/cder/drugsatfda/index.cfm(last visited Oct. 14, 2016). (Petition Paper 20, Exhibit 2067).

Andersson, K.E. "Current Concepts in the Treatment of Disorders of Micturition", Drugs, 1988, pp. 477-494, vol. 35. (Petition Paper 20, Exhibit 2068).

Stahl, M.M.S., et al., "Urodynamic and Other Effects of Tolterodine: A Novel Antimuscarinic Drug for the Treatment of Detrusor Overactivity", Neurourology and Urodynamics, 1995, pp. 647-655, vol. 14. (Petition Paper 20, Exhibit 2069).

Slatter, J.G., et al., "Bioactivation of the Anticancer Agent CPT-11 to SN-38 by Human Hepatic Microsomal Carboxylesterases and the In Vitro Assessment of Potential Drug Interactions", Drug Metabolism and Disposition, 1997, pp. 1157-1164, 25(10). (Petition Paper 17, Exhibit 2059).

CV-Scott Avard MacDiarmid, M.D., FRCPSC. (Petition Paper 17, Exhibit 2060).

Abrams, Paul, et al., "The Standardisation of Terminology of Lower Urinary Tract Function: Report from the Standardisation Subcommittee of the International Continence Society", Neurourology and Urodynamics, 2002, pp. 167-178, vol. 21. (Petition Paper 17 Exhibit 2061).

Abrams, Paul, et al., "Incontinence", 5th International Consultation on Incontinence, Paris Feb. 2012, 5th Edition 2013. (Petition Paper 17, Exhibit 2062).

Abrams, Paul, et al., "Overactive Bladder Significantly Affects Quality of Life", Symposium Proceedings. The American Journal of Managed Care, Jul. 2000, pp. S580-S590. 6(11)Sup. (Petition Paper 17, Exhibit 2063).

Stewart, Walter F., et al., The prevalence and impact of overactive bladder in the U.S. : results from the NOBLE program, Neurourology and Urodynamics, 2001. (Petition Paper 17, Exhibit 2064).

Chapple, Christopher R., et al., "Tolterodine: Selectivity for the Urinary Bladder Over the Eye (as Measured by Visual Accommodation) in Healthy Volunteers", Drugs R&D, 2002, pp. 75-81, 3(2). (Petition Paper 17, Exhibit 2065).

Chapple, Christopher, et al., "The Effects of Antimuscarinic Treatments in Overactive Bladder: An Update of a Systematic Review and Meta-Analysis", European Urology, 2008, pp. 543-562, vol. 54. (Petition Paper 17, Exhibit 2066).

FDA, Drugs@FDS:Ditropan, https://www.accessdata.fda.gov/scripts/cder/drugsatfda/index.cfm(last visited Oct. 14, 2016). (Petition Paper 17, Exhibit 2067).

Andersson, K.E. "Current Concepts in the Treatment of Disorders of Micturition", Drugs, 1988, pp. 477-494, vol. 35. (Petition Paper 17, Exhibit 2068).

Stahl, M.M.S., et al., "Urodynamic and Other Effects of Tolterodine: A Novel Antimuscarinic Drug for the Treatment of Detrusor Overactivity", Neurourology and Urodynamics, 1995, pp. 647-655, vol. 14. (Petition Paper 17, Exhibit 2069).

Detrol LA Prescribing Information, Revised Aug. 2012. (Petition Paper 20, Exhibit 2070).

Malhotra, B.K., et al., "Thorough QT Study with Recommended and Supratherapeutic Doses of Tolterodine", Clinical Pharmacology & Therapeutics, Mar. 2007, pp. 377-385, 81(2). (Petition Paper 20, Exhibit 2071).

FDA Approval Package NDA 20-771. (Petition Paper 20, Exhibit 2072).

Michel, Martin, "Fesoterodine: A novel muscarinic receptor antagonist for the treatment of overactive bladder syndrome", Expert Opinion Pharmacother, 2008, pp. 1787-1796, 9(10). (Petition Paper 20, Exhibit 2073).

Malhotra, B., et al., "The Design and Development of Fesoterodine as a Prodrug of 5-Hydroxymethyl Tolterodine (5-HMT), the Active Metabolite of Tolterodine", Current Medicinal Chemistry, 2009, pp. 4481-4489, vol. 16. (Petition Japer 20, Exhibit 2074).

Nitti, V., et al., "Fesoterodine Is An Effective Antimuscarinic For Patients With Overactive Bladder (OAB): Results of A Phase 2 Trial". (Petition Paper 20, Exhibit 2075).

Chapple, C., "Fesoterodine a New Effective and Well-Tolerated Antimuscarinic for the Treatment of Urgency-Frequency Syndrome: Results of a Phase 2 Controlled Study". (Petition Paper 20, Exhibit 2076).

Chapple, Christopher, et al., "Clinical Efficacy, Safety, and Tolerability of Once-Daily Fesoterodine in Subjects with Overactive Bladder", European Urology, 2007, pp. 1204-1212, vol. 52. (Petition Paper 20, Exhibit 2077).

Nitti, V., et al., "Efficacy, Safety and Tolerability of Fesoterodine for Overactive Bladder Syndrome", The Journal of Urology, Dec. 2007, pp. 2488-2494, vol. 178. (Petition Paper 20, Exhibit 2078).

Dmochowski, Roger R., et al., "Randomized, Double-blind, Placebo-controlled Trial of Flexible-dose Fesoterodine in Subjects with Overactive Bladder", Urology, 2010-pp. 62-68, 75(1). (Petition Paper 20, Exhibit 2079).

Herschorn, Sender, et al., "Efficacy and Tolerability of Fesoterodine in Men with Overacitve Bladder: A Pooled Analysis of 2 Phase III Studies", Journal of Urology, 2010, pp. 1149-1155, 75(5). (Petition Paper 20, Exhibit 2080).

Detrol LA Prescribing Information, Revised Aug. 2012. (Petition Paper 17, Exhibit 2070).

Malhotra, B.K., et al., "Thorough QT Study with Recommended and Supratherapeutic Doses of Tolterodine", Clinical Pharmacology & Therapeutics, Mar. 2007, pp. 377-385, 81(2). (Petition Paper 17, Exhibit 2071).

FDA Approval Package NDA 20-771. (Petition Paper 17, Exhibit 2072).

Michel, Martin, "Fesoterodine: A novel muscarinic receptor antagonist for the treatment of overactive bladder syndrome", Expert Opinion Pharmacother, 2008, pp. 1787-1796, 9(10). (Petition Paper 17, Exhibit 2073).

Malhotra, B., et al., "The Design and Development of Fesoterodine as a Prodrug of 5-Hydroxymethyl Tolterodine (5-HMT), the Active Metabolite of Tolterodine", Current Medicinal Chemistry, 2009, pp. 4481-4489, vol. 16. (Petition Japer 17, Exhibit 2074).

Nitti, V., et al., "Fesoterodine Is an Effective Antimuscarinic for Patients With Overactive Bladder (OAB): Results of A Phase 2 Trial". (Petition Paper 17, Exhibit 2075).

Chapple, C., "Fesoterodine a New Effective and Well-Tolerated Antimuscarinic for the Treatment of Urgency-Frequency Syndrome: Results of a Phase 2 Controlled Study". (Petition Paper 17, Exhibit 2076).

Chapple, Christopher, et al., "Clinical Efficacy, Safety, and Tolerability of Once-Daily Fesoterodine in Subjects with Overactive Bladder", European Urology, 2007, pp. 1204-1212, vol. 52. (Petition Paper 17, Exhibit 2077).

Nitti, V., et al., "Efficacy, Safety and Tolerability of Fesoterodine for Overactive Bladder Syndrome", The Journal of Urology, Dec. 2007, pp. 2488-2494, vol. 178. (Petition Paper 17, Exhibit 2078).

Omochowski, Roger R., et al., "Randomized, Double-blind, Placebo-controlled Trial of Flexible-dose Fesoterodine in Subjects with Overactive Bladder", Urology, 2010-pp. 62-68, 75(1). (Petition Paper 17, Exhibit 2079).

(56) References Cited

OTHER PUBLICATIONS

Herschorn, Sender, et al., "Efficacy and Tolerability of Fesoterodine in Men with Overacitve Bladder: A Pooled Analysis of 2 Phase III Studies", Journal of Urology, 2010, pp. 1149-1155, 75(5). (Petition Paper 17, Exhibit 2080).
Khullar, Vik, et al., "Fesoterodine Dose Response in Subjects With Overactive Bladder Syndrome", Urology, 2008-pp. 839-843, 71(5). (Petition Paper 17, Exhibit 2081).
Chaplin, Steve, et al., "New Products-Fesoterodine (Toviaz): New option for overactive bladder.", Prescriber Nov. 5, 2008, pp. 12-19, www.prescriber.co.uk. (Table 2). (Petition Paper 17, Exhibit 2082).
Malhotra, B., et al., "Thorough QT study of the effect of fesoterodine on cardiac repolarization", International Journal of Clinical Pharmacology and Therapeutics, 2010, pp. 309-318, 48(5). (Petition Paper 17, Exhibit 2083).
Kay, Gary G., et al., Evaluation of Cognitive Function in Healthy Older Subjects Treated with Fesoterdine, Postgraduate Medicine, May 2012, pp. 7-15, 124(3). (Petition Paper 17, Exhibit 2084).
Chapple, Christopher, et al., "Superiority of fesoterodine 8 mg vs 4 mg in reducing urgency urinary incontinence episodes in patients with overactive bladder: results of the randomised, double-blind, placebo-controlled EIGHT trial", British Journal of Urology International, 2014, pp. 415-426, vol. 114. (Petition Paper 17, Exhibit 2085).
Wyndaele, J.J. et al., "Flexible dosing with fesoterodine 4 and 8 mg: a systematic review of data from clinical trials", International Journal of Clinical Practice, Jul. 2014, pp. 830-840, 68(7). (Petition Paper 17, Exhibit 2086).
Khullar, Vik, et al., "Fesoterodine Dose Response in Subjects With Overactive Bladder Syndrome", Urology, 2008-pp. 839-843, 71(5). (Petition Paper 20, Exhibit 2081).
Chaplin, Steve, et al., "New Products-Fesoterodine (Toviaz): New option for overactive bladder.", Prescriber Nov. 5, 2008, pp. 12-19, www.prescriber.co.uk. (Table 2). (Petition Paper 20, Exhibit 2082).
Malhotra, B., et al., "Thorough QT study of the effect of fesoterodine on cardiac repolarization", International Journal of Clinical Pharmacology and Therapeutics, 2010, pp. 309-318, 48(5). (Petition Paper 20, Exhibit 2083).
Kay, Gary G., et al., Evaluation of Cognitive Function in Healthy Older Subjects Treated with Fesoterdine, Postgraduate Medicine, May 2012, pp. 7-15, 124(3). (Petition Paper 20, Exhibit 2084).
Chapple, Christopher, et al., "Superiority of fesoterodine 8 mg vs 4 mg in reducing urgency urinary incontinence episodes in patients with overactive bladder: results of the randomised, double-blind, placebo-controlled EIGHT trial", British Journal of Urology International, 2014, pp. 415-426, vol. 114. (Petition Paper 20, Exhibit 2085).
Wyndaele, J.J. et al., "Flexible dosing with fesoterodine 4 and 8 mg: a systematic review of data from clinical trials", International Journal of Clinical Practice, Jul. 2014, pp. 830-840, 68(7). (Petition Paper 20, Exhibit 2086).
Herschorn, Sender, et al., "Comparison of Fesoterodine and Tolterodine Extended Release for the Treatment of Overactive Bladder: A Head-to-Head Placebo-Controlled Trial", British Journal of Urology, International, Oct. 7, 2009, pp. 58-66, vol. 105. (Petition Paper 20, Exhibit 2087).
Kaplan, S.A., et al., "Superior efficacy of fesoterodine over tolterodine extended release with rapid onset: a prospective, head-to-head placebo-controlled trial", British Journal of Urology, International, 2010, pp. 1432-1440, vol. 107. (Petition Paper 20, Exhibit 2088).
Chapple, Christopher R., et al., "Comparison of fesoterodine and tolterodine in patients with overactive bladder", British Journal of Urology, International, 2008, pp. 1128-1132, vol. 102. (Petition Paper 20, Exhibit 2089).
Kaplan, S.A., et al., "Efficacy and safety of fesoterodine 8 mg in subjects with overactive bladder after a suboptimal response to tolterodine ER", International Journal of Clinical Practice, Sep. 2014, pp. 1065-1073, 68(9). (Petition Paper 20, Exhibit 2090).
Macdiarmid, Scott A., MD., "Overactive Bladder: Improving the Efficacy of Anticholinergics by Dose Escalation"Current Urology Reports, 2003, pp. 446-451, vol. 4. (Petition Paper 20, Exhibit 2091).
CV Leonard J. Chyall, Ph.D. (Petition Paper 20, Exhibit 2092).
History of SPM007—dated Nov. 17, 2000. (Petition Paper 20, Exhibit 2093).
"Chemical Development Plan Incontinence Project", Feb. 10, 1998-Feb. 20, 1998. (Petition Paper 20, Exhibit 2094).
"Timetable of the development of Fesoterodine". (Petition Paper 20, Exhibit 2095).
Minutes Team Meeting "NCE Incontinence" Aug. 10, 1998. (Petition Paper 20, Exhibit 2096).
"Chemical Development Plan Incontinence Project", Jan. 30, 1999-Feb. 24, 1999. (Petition Paper 20, Exhibit 2097).
Herschorn, Sender, et al., "Comparison of Fesoterodine and Tolterodine Extended Release for the Treatment of Overactive Bladder: A Head-to-Head Placebo-Controlled Trial", British Journal of Urology, International, Oct. 7, 2009, pp. 58-66, vol. 105. (Petition Paper 17, Exhibit 2087).
Kaplan, S.A., et al., "Superior efficacy of fesoterodine over tolterodine extended release with rapid onset: a prospective, head-to-head placebo-controlled trial", British Journal of Urology, International, 2010, pp. 1432-1440, vol. 107. (Petition Paper 17, Exhibit 2088).
Chapple, Christopher R., et al., "Comparison of fesoterodine and tolterodine in patients with overactive bladder", British Journal of Urology, International, 2008, pp. 1128-1132, vol. 102. (Petition Paper 17, Exhibit 2089).
Kaplan, S.A., et al., "Efficacy and safety of fesoterodine 8 mg in subjects with overactive bladder after a suboptimal response to tolterodine ER", International Journal of Clinical Practice, Sep. 2014, pp. 1065-1073, 68(9). (Petition Paper 17, Exhibit 2090).
Macdiarmid, Scott A., MD., "Overactive Bladder: Improving the Efficacy of Anticholinergics by Dose Escalation"Current Urology Reports, 2003, pp. 446-451, vol. 4. (Petition Paper 17, Exhibit 2091).
CV Leonard J. Chyall, Ph.D. (Petition Paper 17, Exhibit 2092).
History of SPM007- dated Nov. 17, 2000. (Petition Paper 17, Exhibit 2093).
"Chemical Development Plan Incontinence Project", Feb. 10, 1998-Feb. 20, 1998. (Petition Paper 17, Exhibit 2094).
"Timetable of the development of Fesoterodine". (Petition Paper 17, Exhibit 2095).
Minutes Team Meeting "NCE Incontinence" Aug. 10, 1998. (Petition Paper 17, Exhibit 2096).
"Chemical Development Plan Incontinence Project", Jan. 30, 1999-Feb. 24, 1999. (Petition Paper 17, Exhibit 2097).
Laborjournal: A. Cawello, AC8273.DOC, Dated: Aug. 19, 1999. (Petition Paper 17, Exhibit 2098).
NCE-Incontinece Meeting, Monheim, May 28, 1999. (Petition Paper 17, Exhibit 2099).
"Some Information about SPM 8224" & "Some information about SPM 8272". (Petition Paper 17, Exhibit 2100.
Email from Dr. Arth to Dr. Claus Meese, dated Aug. 31, 1999. (Petition Paper 17, Exhibit 2101).
*Mylan Pharmaceutical Inc.* v. *UCB Pharma GMBH*, U.S. Pat. No. 7,384,980. Petitioner Power of Attorney. (Petition Paper 2).
*Mylan Pharmaceutical Inc.* v. *UCB Pharma GMBH*, U.S. Pat. No. 7,384,980, Petitioner Power of Attorney. (Petition Paper 3).
*Mylan Pharmaceutical Inc. and Mylan Laboratories Limited* v. *UCB Pharma GMBH*, U.S. Pat. No. 7,384,980, Notice of Filing Date Accorded to Petition and Time for the Filing Patent Owner Preliminary Response. (Petition Paper 4).
*Mylan Pharmaceutical Inc.* v. *UCB Pharma GMBH*, U.S. Pat. No. 7,384,980. Petition for Inter Partes Review Under 35 U.S.C. §§ 311-319 and 37 C.F.R. §§42.100 ET SEQ. (Petition Paper 5).
*Mylan Pharmaceutical Inc. and Mylan Laboratories Limited* v. *UCB Pharma GMBH*, U.S. Pat. No. 7,384,980, Notice of Accepting Corrected Petition. (Petition Paper 6).
*Mylan Pharmaceutical Inc. and Mylan Laboratories Limited* v. *UCB Pharma GMBH*, U.S. Pat. No. 7,384,980, Patent owner Power of Attorney. (Petition Paper 7).

(56) References Cited

OTHER PUBLICATIONS

*Mylan Pharmaceutical Inc. and Mylan Laboratories Limited* v. *UCB Pharma GMBH*, U.S. Pat. No. 7,384,980, Patent owner Mandatory Notice Information Under 27 C.F.R. § 42.8 (Petition Paper 8).
*Mylan Pharmaceutical Inc.* v. *UCB Pharma GMBH*, U.S. Pat. No. 7,855,230. Petitioner Power of Attorney. (Petition Paper 2).
*Mylan Pharmaceutical Inc.* v. *UCB Pharma GMBH*, U.S. Pat. No. 7,855,230, Petitioner Power of Attorney. (Petition Paper 3).
*Mylan Pharmaceutical Inc. and Mylan Laboratories Limited* v. *UCB Pharma GMBH*, U.S. Pat. No. 7,855,230, Notice of Filing Date Accorded to Petition and Time for the Filing Patent Owner Preliminary Response. (Petition Paper 4).
*Mylan Pharmaceutical Inc.* v. *UCB Pharma GMBH*, U.S. Pat. No. 7,855,230. Petition for Inter Partes Review Under 35 U.S.C. §§ 311-319 and 37 C.F.R. §§42.100 ET SEQ. (Petition Paper 5).
*Mylan Pharmaceutical Inc. and Mylan Laboratories Limited* v. *UCB Pharma GMBH*, U.S. Pat. No. 7,855,230, Notice of Accepting Corrected Petition. (Petition Paper 6).
*Mylan Pharmaceutical Inc. and Mylan Laboratories Limited* v. *UCB Pharma GMBH*, U.S. Pat. No. 7,855,230, Patent owner Power of Attorney. (Petition Paper 7).
*Mylan Pharmaceutical Inc. and Mylan Laboratories Limited* v. *UCB Pharma GMBH*, U.S. Pat. No. 7,855,230, Patent owner Mandatory Notice Information Under 27 C.F.R. § 42.8 (Petition Paper 8).
*Mylan Pharmaceutical Inc.* v. *UCB Pharma GMBH*, U.S. Pat. No. 8,338,478. Petitioner Power of Attorney. (Petition Paper 2).
*Mylan Pharmaceutical Inc.* v. *UCB Pharma GMBH*, U.S. Pat. No. 8,338,478, Petitioner Power of Attorney. (Petition Paper 3).
*Mylan Pharmaceutical Inc. and Mylan Laboratories Limited* v. *UCB Pharma GMBH*, U.S. Pat. No. 8,338,478, Notice of Filing Date Accorded to Petition and Time for the Filing Patent Owner Preliminary Response. (Petition Paper 4).
*Mylan Pharmaceutical Inc.* v. *UCB Pharma GMBH*, U.S. Pat. No. 8,338,478. Petition for Inter Partes Review Under 35 U.S.C. §§ 311-319 and 37 C.F.R. §§42.100 ET SEQ. (Petition Paper 5).
*Mylan Pharmaceutical Inc. and Mylan Laboratories Limited* v. *UCB Pharma GMBH*, U.S. Pat. No. 8,338,478, Notice of Accepting Corrected Petition. (Petition Paper 6).
*Mylan Pharmaceutical Inc. and Mylan Laboratories Limited* v. *UCB Pharma GMBH*, U.S. Pat. No. 8,338,478, Patent owner Power of Attorney. (Petition Paper 7).
*Mylan Pharmaceutical Inc. and Mylan Laboratories Limited* v. *UCB Pharma GMBH*, U.S. Pat. No. 8,338,478, Patent owner Mandatory Notice Information Under 27 C.F.R. § 42.8 (Petition Paper 8).
*Mylan Pharmaceutical Inc.* v. *UCB Pharma GMBH*, U.S. Pat. No. 7,985,772. Petitioner Power of Attorney. (Petition Paper 2).
*Mylan Pharmaceutical Inc.* v. *UCB Pharma GMBH*, U.S. Pat. No. 7,985,772, Petitioner Power of Attorney. (Petition Paper 3).
*Mylan Pharmaceutical Inc. and Mylan Laboratories Limited* v. *UCB Pharma GMBH*, U.S. Pat. No. 7,985,772, Notice of Filing Date Accorded to Petition and Time for the Filing Patent Owner Preliminary Response. (Petition Paper 4).
*Mylan Pharmaceutical Inc.* v. *UCB Pharma GMBH*, U.S. Pat. No. 7,985,772. Petition for Inter Partes Review Under 35 U.S.C. §§ 311-319 and 37 C.F.R. §§42.100 ET SEQ. (Petition Paper 5).
*Mylan Pharmaceutical Inc. and Mylan Laboratories Limited* v. *UCB Pharma GMBH*, U.S. Pat. No. 7,985,772, Notice of Accepting Corrected Petition. (Petition Paper 6).
*Mylan Pharmaceutical Inc. and Mylan Laboratories Limited* v. *UCB Pharma GMBH*, U.S. Pat. No. 7,985,772, Patent owner Power of Attorney. (Petition Paper 7).
*Mylan Pharmaceutical Inc. and Mylan Laboratories Limited* v. *UCB Pharma GMBH*, U.S. Pat. No. 7,985,772, Patent owner Mandatory Notice Information Under 27 C.F.R. § 42.8 (Petition Paper 8).
Laborjournal: A. Cawello, AC8273.DOC, Dated: Aug. 19, 1999. (Petition Paper 20, Exhibit 2098).
NCE-Incontinece Meeting, Monheim, May 28, 1999. (Petition Paper 20, Exhibit 2099).
"Some Information about SPM 8224" & "Some information about SPM 8272". (Petition Paper 20, Exhibit 2100.
Email from Dr. Arth to Dr. Claus Meese, dated Aug. 31, 1999. (Petition Paper 20, Exhibit 2101).
*Mylan Pharmaceutical Inc.* v. *UCB Pharma GMBH*, U.S. Pat. No. 6,858,650. Petitioner Power of Attorney. (Petition Paper 2).
*Mylan Pharmaceutical Inc.* v. *UCB Pharma GMBH*, U.S. Pat. No. 6,858,650, Petitioner Power of Attorney. (Petition Paper 3).
*Mylan Pharmaceutical Inc. and Mylan Laboratories Limited* v. *UCB Pharma GMBH*, U.S. Pat. No. 6,858,650, Notice of Filing Date Accorded to Petition and Time for the Filing Patent Owner Preliminary Response. (Petition Paper 4).
*Mylan Pharmaceutical Inc.* v. *UCB Pharma GMBH*, U.S. Pat. No. 6,858,650. Corrected Petition or Inter Partes Review Under 35 U.S.C. §§ 311-319 and 37 C.F.R. §§42.100 ET SEQ. (Petition Paper 5).
*Mylan Pharmaceutical Inc. and Mylan Laboratories Limited* v. *UCB Pharma GMBH*, U.S. Pat. No. 6,858,650, Notice of Accepting Corrected Petition. (Petition Paper 6).
*Mylan Pharmaceutical Inc. and Mylan Laboratories Limited* v. *UCB Pharma GMBH*, U.S. Pat. No. 6,858,650, Patent Owner Mandatory Notice Information Under 37 C.F.R. § 42.8 (Petition Paper 7).
*Mylan Pharmaceutical Inc. and Mylan Laboratories Limited* v. *UCB Pharma GMBH*, U.S. Pat. No. 6,858,650, Patent Owner Power of Attorney. (Petition Paper 8).
*Mylan Pharmaceutical Inc. and Mylan Laboratories Limited* v. *UCB Pharma GMBH*, IPR2016-00510 (U.S. Pat. No. 6,858,650), IPR2016-00512 (U.S. Pat. No. 7,384,980), IPR2016-00514 (U.S. Pat. No. 7,855,230), IPR2016-00516 (U.S. Pat. No. 8,338,478), IPR2016-00517 (U.S. Pat. No. 7,985,772); Order Conduct of Proceedings 37 C.F.R. § 42.5. (Petition Paper 11).
*Mylan Pharmaceutical Inc. and Mylan Laboratories Limited* v. *UCB Pharma GMBH*, U.S. Pat. No. 6,858,650, Decision Institution of Inter Partes Review 37 C.F.R. §42.108. (Petition Paper 12).
*Mylan Pharmaceutical Inc. and Mylan Laboratories Limited* v. *UCB Pharma GMBH*, IPR2016-00510 (U.S. Pat. No. 6,858,650), IPR2016-00512 (U.S. Pat. No. 7,384,980), IIPR2016-00517(U.S. Pat. No. 7,985,772); Scheduling Order. (Petition Paper 13).
*Mylan Pharmaceutical Inc. and Mylan Laboratories Limited* v. *UCB Pharma GMBH*, U.S. Pat. No. 6,858,650, Decision Patent Owner's Request for Rehearing 37 C.F.R. §42.71. (Petition Paper 18).
*Mylan Pharmaceutical Inc. and Mylan Laboratories Limited* v. *UCB Pharma GMBH*, U.S. Pat. No. 6,858,650, Patent owner's Notice of Objections to Evidence 37 C.F.R. §42.64. (Petition Paper 16).
*Mylan Pharmaceutical Inc. and Mylan Laboratories Limited* v. *UCB Pharma GMBH*, U.S. Pat. No. 6,858,650, Patent Owner's Notice of Deposition of Steven E. Patterson, Ph.D. (Petition Paper 19).
*Mylan Pharmaceutical Inc. a* v. *UCB Pharma GMBH*, U.S. Pat. No. 6,858,650, Petitioner's Objections to Patent Owner's Evidence Pursuant to 37 C.F.R. §42.64. (Petition Paper 21).
Patent Trial and Appeal Board; *Alembic Pharmaceuticals Limited* v. *UCB Pharma GMBH*; IPR2016-01596-US6858650-Petition for Inter Partes Review Under 35 U.S.C. §§ 311-319 and 37 C.F.R. §§42.100 ET SEQ. (Petition Paper 1).
*Alembic Pharmaceuticals Limited* v. *UCB Pharma GMBH*, IPR2016-01596-US6858650. Petitioner Alembic Pharmaceuticals Limited Power of Attorney. (Petition Paper 2).
*Alembic Pharmaceuticals Limited* v. *UCB Pharma GMBH*, IPR2016-01596-US6858650. Motion for Joinder Pursuant to 35 U.S.C. § 315(c) and C.F.R. § 42.122(b). (Petition Paper 3).
*Alembic Pharmaceuticals Limited* v. *UCB Pharma GMBH*, IPR2016-01596-US6858650, Notice of Filing Date Accorded to Petition and Time for the Filing Patent Owner Preliminary Response. (Petition Paper 4).
*Alembic Pharmaceuticals Limited* v. *UCB Pharma GMBH*, IPR2016-01596-US6858650. Patent Owner Mandatory Notice Information Under 37 C.F.R. § 42.8. (Petition Paper 5).

(56) References Cited

OTHER PUBLICATIONS

*Alembic Pharmaceuticals Limited v. UCB Pharma GMBH,* IPR2016-01596-US6858650. Patent Power of Attorney. (Petition Paper 6).
*Torrent Pharmaceuticals Limited v. UCB Pharma GMBH,* IPR2016-01636-US6858650. Petitioner Torrent Pharmaceuticals Limited's Power of Attorney. (Paper 1).
Patent Trial and Appeal Board; *Torrent Pharmaceuticals Limited v. UCB Pharma GMBH,* IPR2016-01636-US6858650. Petition for Inter Partes Review Under 35 U.S.C. §§ 311-319 and 37 C.F.R. §§42.100 ET SEQ. (Petition Paper 2).
*Torrent Pharmaceuticals Limited v. UCB Pharma GMBH,* IPR2016-01636-US6858650. Motion for Joinder Pursuant to 35 U.S.C. § 315(c) and C.F.R. § 42.122(b). (Petition Paper 3).
*Torrent Pharmaceuticals Limited v. UCB Pharma GMBH,* IPR2016-01636-US6858650. Certificate of Word Count of Petition for Inter Partes Review. (Petition Paper 4).
*Torrent Pharmaceuticals Limited v. UCB Pharma GMBH,* IPR2016-01636-US6858650. Notice of Filing Date Accorded to Petition and Time for the Filing Patent Owner Preliminary Response. (Petition Paper 5).
*Torrent Pharmaceuticals Limited v. UCB Pharma GMBH,* IPR2016-01636-US6858650. Patent Owner Mandatory Notice Information Under 37 C.F.R. § 42.8. (Petition Paper 8).
*Torrent Pharmaceuticals Limited v. UCB Pharma GMBH,* IPR2016-01636-US6858650, Patent Owner Power of Attorney. (Paper 9).
Patent Trial and Appeal Board; *Amerigen Pharmaceuticals Limited v. UCB Pharma GMBH,* IPR2016-01665-US6858650. Petition for Inter Partes Review Under 35 U.S.C. §§ 311-319 and 37 C.F.R. §§42.100 ET SEQ. (Petition Paper 1).
*Amerigen Pharmaceuticals Limited v. UCB Pharma GMBH,* IPR2016-01665-US6858650. Power of Attorney for Amerigen Pharmaceuticals, Ltd. (Paper 2).
*Amerigen Pharmaceuticals Limited v. UCB Pharma GMBH,* IPR2016-01665-US6858650. Motion for Joinder Pursuant b 35 U.S.C. § 315(c) and C.F.R. § 42.122(b). (Petition Paper 3).
*Amerigen Pharmaceuticals Limited v. UCB Pharma GMBH,* IPR2016-01665-US6858650. Certificate of Word Count of Petition for Inter Partes Review. (Petition Paper 4).
*Amerigen Pharmaceuticals Limited v. UCB Pharma GMBH,* IPR2016-01665-US6858650. Notice of Filing Date Accorded to Petition and Time for the Filing Patent Owner Preliminary Response. (Petition Paper 5).
*Amerigen Pharmaceuticals Limited v. UCB Pharma GMBH,* IPR2016-01665-US6858650. Patent Owner Mandatory Notice Information Under 37 C.F.R. § 42.8 (Petition Paper 6).
*Amerigen Pharmaceuticals Limited v. UCB Pharma GMBH,* IPR2016-01665-US6858650. Patent Owner Power of Attorney (Petition Paper 7).
Patent Trial and Appeal Board; *Mylan Pharmaceuticals Inc., vs UCB Pharma GMBH;* IPR2016-00512-US7384980. Petition for Inter Partes Review Under 35 U.S.C. §§ 311-319 and 37 C.F.R. §§42.100 ET SEQ. (Petition Paper 1).
Declaration of Steven E. Patterson, Ph.D. (Petition Paper 1, Exhibit 1003).
Andersson, K.E., et al., "The pharmacological treatment of urinary incontinence", British Journal of Urology International, 1999, pp. 923-947, vol. 84. (Petition Paper 1, Exhibit 1006).
Brynne, Niclas, et al., "Pharmacokinetics and pharmacodynamics of tolterodine in man: a new drug for the treatment of urinary bladder overactivity", International Journal of Clinical Pharmacology and Therapeutics, 1997, pp. 287-295, 35(7). (Petition Paper 1, Exhibit 1007).
Thomas, Simon H.L., et al., "Concentration dependent cardiotoxicity of terodine in patients treated for urinary Incontinence", British Heart Journal, 1995, pp. 53-56, vol. 74. (Petition Paper 1, Exhibit 1008).
Detrol tolterodine tartrate tablets, Label. Phamacia & UpJohn. (Petition Paper 1, Exhibit 1009).

Postlind, Hans, et al., "Tolterodine, A New Muscarinic Receptor Antagonist, Is Metabolized by Cytochromes P450 2D6 and 3A In Human Liver Microsomes", Drug Metabolism and Dispositon, 1998, pp. 289-293, 26(4). (Petition Paper 1, Exhibit 1010).
Brynne, Niclas, et al., "Influence of CYP2D6 polymorphism on the pharmacokinetics and pharmacodynamics of tolterodine", Clinical Pharmacology & Therapeutics, May 1998, pp. 529-539, 63(5). (Petition Paper 1, Exhibit 1011).
Bundgaard, Hans, "Design of Prodrugs", 1985, pp. 1-360. (Petition Paper 1, Exhibit 1012-Parts 1-4).
Berge, Stephen M., et al., "Pharmaceutical Salts", Journal of Pharmaceutical Sciences Review Article, Jan. 1977, pp. 1-19, 66(1). (Petition Paper 1, Exhibit 1013).
Patent Trial and Appeal Board; *Mylan Pharmaceuticals Inc., vs UCB Pharma GMBH;* IPR2016-00514-US7855230. Petition for Inter Partes Review Under 35 U.S.C. §§ 311-319 and 37 C.F.R. §§42.100 ET SEQ. (Petition Paper 1).
Patent Trial and Appeal Board; *Mylan Pharmaceuticals Inc., vs UCB Pharma GMBH;* IPR2016-00516-US8,338,478. Petition for Inter Partes Review Under 35 U.S.C. §§ 311-319 and 37 C.F.R. §§42.100 ET SEQ. (Petition Paper 1).
Patent Trial and Appeal Board; *Mylan Pharmaceuticals Inc., vs UCB Pharma GMBH;* IPR2016-00517-US7985772. Petition for Inter Partes Review Under 35 U.S.C. §§ 311-319 and 37 C.F.R. §§42.100 ET SEQ. (Petition Paper 1).
Patent Trial and Appeal Board; *Mylan Pharmaceuticals Inc., vs UCB Pharma GMBH;* IPR2016-00510-US6858650-Petition for Inter Partes Review Under 35 U.S.C. §§ 311-319 and 37 C.F.R. §§42.100 ET SEQ. (Petition Paper 1).
Andersson, STIG H.G., et al., "Biotransformation of Tolterodine, A New Muscarinic Receptor Antagonist, In Mice, Rats and Dogs", Drug Metabolism and Disposition, 1998, pp. 528-535, 26(6). (Petition Paper 1, Exhibit 1014).
Nilvebrant, Lisbeth, "Antimuscarinic Potency and Bladder Selectivity of PNU-200577, a Major Metabolite of Tolterodine", Pharmacology & Toxicology, 1997, pp. 169-172, vol. 81. (Petition Paper 1, Exhibit 1015).
Demaagd, George, A., et al., "Management of Urinary Incontinence", P&T, Jun. 2012, pp. 345-361H, 37(6). (Petition Paper 1, Exhibit 1016).
Appell, Rodney A., "Clinical Efficacy and Safety of Tolterodine in the Treatment of Overactive Bladder: A Pooled Analysis", Urology, Dec. 1997, pp. 90-96, 50(Supplement 6A). (Petition Paper 1, Exhibit 1017).
Ashworth, Laurel, "Is My Antihistamine Safe", Home Care Provider, Jun. 1997, pp. 117-120, 2(3). (Petition Paper 1, Exhibit 1018).
Lipinski, Christopher A., "Experimental and computational approaches to estimate solubility and permeability in drug discovery and development settings", Advanced Drug Delivery Reviews, 1997, pp. 3-25, vol. 23. (Petition Paper 1, Exhibit 1019).
Gormley E. Ann, et al., "Diagnosis and Treatment of Overactive Bladder (Non-Neurogenic) in Adults: AUA/SUFU Guideline", American Urological Association Education and Research Inc., 2014, pp. 1-57. (Petition Paper 1, Exhibit 1021).
Pfizer Press Release "Study shows Toviaz Is Effective in Reducing Urge Urinary Incontinence in Patients with Overactive Bladder After Suboptimal Response to Detrol LA", Aug. 2, 2012. (Petition Paper 1, Exhibit 1022).
Leonhauser, Melissa, "PM360-Apr. 2, 2012, Overactive Bladder Market: Managing the Future", https://www.pm360online.com/overactive-bladder-market-managing-the-furture/[Jan. 13, 2016 10:29:38 AM], (Petition Paper 1, Exhibit 1023).
Toviaz-Pfizer Label-Highlight of Prescribing Information. (Petition Paper 1, Exhibit 1024).
FDA Approval Letter NDA 20-771, (Petition Paper 1, Exhibit 1025).
"FDA Guidance" Applications Covered by Section 505(b)(2)-Oct. 1999-FDA(CDER). (Petition Paper 1, Exhibit 1026).
Gould, Philip L., "Salt selection for basic drugs", International Journal of Pharmaceutics, 1986, pp. 201-217, vol. 33. (Petition Paper 1, Exhibit 1027).

(56) References Cited

OTHER PUBLICATIONS

Alabaster, V.A., "Discovery & Development of Selective M3 Antagonists for Clinical Use", Life Sciences, 1997, pp. 1053-1060, 60(13/14). (Petition Paper 1, Exhibit 1028).
Takeuchi, M., et al., "1,2,3,4-Tetrahydro-2-Isoquinolinecarboxylate Derivatives: A Novel Class of Selective Muscarinic Antagonists. III", Abstract of Papers Part 2, 213th ACS National Meeting 0/8412-3500-7, American Chemical Society, San Francisco, CA, Apr. 13-17, 1997. (Petition Paper 1, Exhibit 1029).
Goldberg, Michael R., et al., DuP 532, an angiotensin II receptor antagonist: First administration and comparison with losartan, Clinical Pharmacology & Therapeutics, Jan. 1997, pp. 59-69, 61(1). (Petition Paper 1, Exhibit 1030).
Begley, David J., "The Blood-brain Barrier: Principles for Targeting Peptides and Drugs to the Central Nervous System", Journal Pharmaceutical Pharmacology, 1996, pp. 136-146, vol. 48. (Petition Paper 1, Exhibit 1031).
Declaration of Deforest McDuff, Ph.D. (Petition Paper 1, Exhibit 1033).
Toviaz-Don't Let Overactive Bladder Stop You in Your Track. (Petition Paper 1, Exhibit 1035).
Toviaz U.S and Worldwide Sales. (Petition Paper 1, Exhibit 1036).
U.S. OAB Prescriptions and Shares by Drug (2008-2014). (Petition Paper 1, Exhibit 1037).
U.S. OAB Sales and Shares by Drug (2008-2014). (Petition Paper 1, Exhibit 1038).
U.S. OAB Market Share, Prescriptions, and Sales by Drug (2000-2007). Prescription Path of Toviaz and Other OAB Drugs. (Petition Paper 1, Exhibit 1039).
Prescription Path of Toviaz and Other OAB Drugs. (Petition Paper 1, Exhibit 1040).
Sales Path of Toviaz and Other OAB Drugs. (Petition Paper 1, Exhibit 1041).
Sales Path of Toviaz Compared to Pharmaceutical Industry Benchmarks. (Petition Paper 1, Exhibit 1042).
Comparison of Toviaz Sales to Pharmaceutical Industry Benchmarks. (Petition Paper 1, Exhibit 1043).
Chart Sales Path of Toviaz Compared to Pharmaceutical Industry Benchmarks. (Petition Paper 1, Exhibit 1044).
Present Value of Toviaz U.S. Sales. (Petition Paper 1, Exhibit 1045).
Present Value of Toviaz Worldwide Sales. (Petition Paper 1, Exhibit 1046).
Estimate of Expected R&D Cost. (Petition Paper 1, Exhibit 1047).
U.S. OAB Detail Shares by Drug (2008-2015). (Petition Paper 1, Exhibit 1048).
Consumer Price Index (CPI). (Petition Paper 1, Exhibit 1049).
CV of Steven E. Patterson, Ph.D. (Petition Paper 1, Exhibit 1004).
Dkt. 6-2015-01-28 Summon Returned Executed, Civil Action. Case No. 1:15-cv-00079-GMS, *Pfizer, et al* v *Mylan Pharmaceutical Inc.* (Dist. of DE). (Petition Paper 1, Exhibit 1032).
CV of DeForest McDuff, Jan. 2016. (Petition Paper 1, Exhibit 1034).
Petitioner *Mylan Pharmaceutical Inc. and Mylan Laboratories Limited* v. *UCB Pharma GMBH*. Patent Owner's Response. U.S. Pat. No. 7,384,980, IPR2016-00512-US7384980. (Petition Paper 17).
UBS—Investment Research-US Pharmaceuticals USB Large Cap Pharmaceutical Monthly Handbook (20110824) Excerpt. (Petition Paper 15, Exhibit 1051).
UBS—Investment Research-US Pharmaceuticals USB Large Cap Pharmaceutical Monthly Handbook (20160104) Excerpt. (Petition Paper 15, Exhibit 1052).
US Securities and Exchange Commission—2012 Form 10-K. (Petition Paper 15, Exhibit 1053).
Petitioner *Mylan Pharmaceutical Inc. and Mylan Laboratories Limited* v. *UCB Pharma GMBH*. Patent Owner's Response. U.S. Pat. No. 7,855,230, IPR2016-00514-US7855230. (Petition Paper 17).

Petitioner *Mylan Pharmaceutical Inc. and Mylan Laboratories Limited* v. *UCB Pharma GMBH*. Patent Owner's Response. U.S. Pat. No. 8,338,478, IPR2016-00516-US8338478. (Petition Paper 17).
Petitioner *Mylan Pharmaceutical Inc. and Mylan Laboratories Limited* v. *UCB Pharma GMBH*. Patent Owner's Response. U.S. Pat. No. 7,985,772, IPR2016-00517-US7985772. (Petition Paper 17).
Petitioner Mylan Pharmaceutical Inc.'s Response to Patent Owner's Objections and Supplemental Evidence Pursuant to 37 C.F.R. § 42.64(b)(2).U.S. Patent No. 6,858,650, IPR2016-00510-US6858650. (Petition Paper 17).
UBS—Investment Research-US Pharmaceuticals USB Large Cap Pharmaceutical Monthly Handbook (20110824) Excerpt. (Petition Paper 17, Exhibit 1050).
UBS—Investment Research-US Pharmaceuticals USB Large Cap Pharmaceutical Monthly Handbook (20160104) Excerpt. (Petition Paper 17, Exhibit 1051).
US Securities and Exchange Commission—2012 Form 10-K. (Petition Paper 17, Exhibit 1052).
US Securities and Exchange Commission-2012 Form 10-K 2015. (Petition Paper 15, Exhibit 1054).
UBS—Investment Research—US Pharmaceuticals USB Large Cap Pharmaceutical Monthly Handbook (20101126) Excerpt. (Petition Paper 15, Exhibit 1055).
UBS—Investment Research—US Pharmaceuticals USB Large Cap Pharmaceutical Monthly Handbook (20131115) Excerpt. (Petition Paper 15, Exhibit 1056).
Cowen Pharmaceutical Therapeutic Categories Outlook (200110) Excerpt. (Petition Paper 15, Exhibit 1057).
Cowen Pharmaceutical Therapeutic Categories Outlook (200210) Excerpt. (Petition Paper 15, Exhibit 1058).
Cowen Pharmaceutical Therapeutic Categories Outlook (200310) Excerpt. (Petition Paper 15, Exhibit 1059).
Cowen Pharmaceutical Therapeutic Categories Outlook (200403) Excerpt. (Petition Paper 15, Exhibit 1060).
Cowen Pharmaceutical Therapeutic Categories Outlook (200510) Excerpt. (Petition Paper 15, Exhibit 1061).
Cowen Therapeutic Categories Outlook (200610) Excerpt. (Petition Paper 15, Exhibit 1062).
Cowen Therapeutic Categories Outlook (200710) Excerpt. (Petition Paper 15, Exhibit 1063).
US Securities and Exchange Commission-2012 Form 10-K 2015. (Petition Paper 17, Exhibit 1053).
UBS—Investment Research—US Pharmaceuticals USB Large Cap Pharmaceutical Monthly Handbook (20101126) Excerpt. (Petition Paper 17, Exhibit 1054).
UBS—Investment Research—US Pharmaceuticals USB Large Cap Pharmaceutical Monthly Handbook (20131115) Excerpt. (Petition Paper 17, Exhibit 1055).
Cowen Pharmaceutical Therapeutic Categories Outlook (200110) Excerpt. (Petition Paper 17, Exhibit 1056).
Cowen Pharmaceutical Therapeutic Categories Outlook (200210) Excerpt. (Petition Paper 17, Exhibit 1057).
Cowen Pharmaceutical Therapeutic Categories Outlook (200310) Excerpt. (Petition Paper 17, Exhibit 1058).
Cowen Pharmaceutical Therapeutic Categories Outlook (200403) Excerpt. (Petition Paper 17, Exhibit 1059).
Cowen Pharmaceutical Therapeutic Categories Outlook (200510) Excerpt. (Petition Paper 17, Exhibit 1060).
Cowen Therapeutic Categories Outlook (200610) Excerpt. (Petition Paper 17, Exhibit 1061).
Cowen Therapeutic Categories Outlook (200710) Excerpt. (Petition Paper 17, Exhibit 1062).
Cowen Pharmaceutical Therapeutic Categories Outlook (200809) Excerpt. (Petition Paper 15, Exhibit 1064).
Grabowski, Henry, et al., "Returns on Research and Development for 1990s New Drug Introductions", Pharmacoeconomics 2002, pp. 11-29, 20(Suppl 3). (Petition Paper 15, Exhibit 1065).
Grabowski, Henry, et al., "Briefing Cost of Developing a New Drug" Tufts Center for the Study of Drug Development, Nov. 18, 2014. (Petition Paper 15, Exhibit 1066).

(56) References Cited

OTHER PUBLICATIONS

Moore, Thomas, et al., "Development Times, Clinical Testing, Postmarket Follow-up, and Safety Risks for the New Drugs Approved by the US Food and Drug Administration The Class of 2008", 2014 JAMA Intern Med., pp. 90-95, 174 (1). (Petition Paper 15, Exhibit 1067).
Adams, Christopher, et al., "Estimating the Cost of New Drug Development: Is It Really $802 Million?" Health Affairs, Mar./Apr. 2006, pp. 420-428, 25(2). (Petition Paper 15, Exhibit 1068).
Adams, Christopher, et al., "Spending on New Drug Development" Health Economics, 2009, pp. 130-141, 19(2). (Petition Paper 15, Exhibit 1069).
Clinical Trials.gov, Two Phase extension Trial of SP668 to Investigate the Safety and Tolerability of Sustained Release Fesoterodine in Subjects with Overactive Bladder: A Double-Blind Phase Followed by an Open-Label Extension Phase, https://www.clinicaltrials.gov/ct2/show/NCT00220389?term=fesoterodine&rank=50. (Petition Paper 15, Exhibit 1071).
FDA Approval Letter NDA 22-030 Toviaz, Oct. 31, 2008. (Petition Paper 15, Exhibit 1072).
St. Louis Federal Reserve Consumer Price Index for All Urban Consumers: All Items (CPI), https://research.stlouisfed.org/fred2/data/USACPIALLAINMEI.txt. (Petition Paper 15, Exhibit 1073).
Memorandum Opinion, *Pfizer Inc., and UCB Pharma GMBH* v. *Sandoz Inc., et al.*, CA. No., 1;13/1110-GMS (D. Del. Apr. 20, 2016), ECF No. 304. (Petition Paper 17, Exhibit 2001).
Petitioner *Mylan Pharmaceutical Inc. and Mylan Laboratories Limited* v. *UCB Pharma GMBH*. Patent Owner's Response. U.S. Pat. No. 8,338,478 IPR2016-00516-US8338478. (Petition Paper 17).
Petitioner *Mylan Pharmaceutical Inc. and Mylan Laboratories Limited* v. *UCB Pharma GMBH*. Patent Owner's Response. U.S. Pat. No. 7,985,772 IPR2016-00517-US7985772. (Petition Paper 17).
Cowen Pharmaceutical Therapeutic Categories Outlook (200809) Excerpt. (Petition Paper 17, Exhibit 1063).
Grabowski, Henry, et al., "Returns on Research and Development for 1990s New Drug Introductions", Pharmacoeconomics 2002, pp. 11-29, 20(Suppl 3). (Petition Paper 17, Exhibit 1064).
Grabowski, Henry, et al., "Briefing Cost of Developing a New Drug" Tufts Center for the Study of Drug Development, Nov. 18, 2014. (Petition Paper 17, Exhibit 1065).
Moore, Thomas, et al., "Development Times, Clinical Testing, Postmarket Follow-up, and Safety Risks for the New Drugs Approved by the US Food and Drug Administration the Class of 2008", 2014 JAMA Intern Med., pp. 90-95, 174 (1). (Petition Paper 17, Exhibit 1066).
Adams, Christopher, et al., "Estimating the Cost of New Drug Development: Is It Really $802 Million?" Health Affairs, Mar./Apr. 2006, pp. 420-428, 25(2). (Petition Paper 17, Exhibit 1067).
Adams, Christopher, et al., "Spending on New Drug Development" Health Economics, 2009, pp. 130-141, 19(2). (Petition Paper 17, Exhibit 1068).
Clinical Trials.gov, Two Phase extension Trial of SP668 to Investigate the Safety and Tolerability of Sustained Release Fesoterodine in Subjects with Overactive Bladder: A Double-Blind Phase Followed by an Open-Label Extension Phase, https://www.clinicaltrials.gov/ct2/show/NCT00220389?term=fesoterodine&rank=50. (Petition Paper 17, Exhibit 1070).
FDA Approval Letter NDA 22-030 Toviaz, Oct. 31, 2008. (Petition Paper 17, Exhibit 1071).
St. Louis Federal Reserve Consumer Price Index for All Urban Consumers: All Items (CPI), https://research.stlouisfed.org/fred2/data/USACPIALLAINMEI.txt. (Petition Paper 17, Exhibit 1072).
*Mylan Pharmaceutical Inc. and Mylan Laboratories Limited* v. *UCB Pharma GMBH* Case IPR2016-00510, Patent Owner Preliminary Response. (Petition Paper 9).
Memorandum Opinion, *Pfizer Inc., and UCB Pharma GMBH* v. *Sandoz Inc., et al.*, CA. No., 1;13/1110-GMS (D. Del. Apr. 20, 2016), ECF No. 304. (Petition Paper 9, Exhibit 2001).

Declaration William R. Roush, Ph.D. (Petition Paper 17, Exhibit 2002).
CV for William R. Roush Biographical Data (Petition Paper 17, Exhibit 2003).
Nilvebrant, et al., "Tolterodine—A New Bladder Selective Muscarinic Receptor Antagonist: Preclinical Pharmacological and Clinical Data", Life Science, 1997, pp. 1129-1136, 60(13114). (Petition Paper 17, Exhibit 2004).
Callegari, E, et al., "A comprehensive non-clinical evaluation of the CNS penetration potential of antimuscarinic agents for the treatment of overactive bladder", British Journal of Clinical Pharmacology, 2011, pp-235-246, 72(2). (Petition Paper 17, Exhibit 2005).
Trial Transcript, *Pfizer Inc., et al.,* v. *Sandoz Inc., et al.*, C.A. No., 1;13/1110-GMS (D. Del. Jul. 13-16, 2015). (Petition Paper 17, Exhibit 2006).
Wein, A.J., Mundy, A.R., et al., "Urodynamics Principles, Practice and Application" Second Edition, 1994, pp. 43-70-"Pharmacologic treatment of voiding dysfunction". (Petition Paper 17, Exhibit 2008).
Detrol LA tolterodine tartrate extened release capsules. (Petition Paper 17, Exhibit 2009).
Krise, Jeffrey P., et al., "Novel Prodrug Approach for Tertiary Amines: Synthesis and Preliminary Evaluation of N-Phosphonooxymethyl Prodrugs", Journal of Medicinal Chemistry, 1999, pp. 3094-3100, vol. 42. (Petition Paper 17, Exhibit 2013).
Sinkul, A.A. et al., "Rationale for Design of Biologically Reversible Drug Derivatives: Prodrugs", Journal of Pharmaceutical Scienes, Feb. 1975, pp. 181-210, 64(2). (Petition Paper 17, Exhibit 2014).
Bundgaard, H, "Novel Chemical Approaches in Prodrug Design", Drugs of the Future, 1991, pp. 443-458, 16(5). (Petition Paper 17, Exhibit 2015).
Jann, Michael W., et al., Clinical Pharmacokinetics of the Deport Antipsychotics, Clinical Pharmacokinetics, 1985, pp. 315-333, vol. 10. (Petition Paper 17, Exhibit 2016).
Declaration William R. Roush, Ph.D. (Petition Paper 9, Exhibit 2002).
CV for William R. Roush Biographical Data (Petition Paper 9, Exhibit 2003).
Nilvebrant, et al., "Tolterodine—A New Bladder Selective Muscarinic Receptor Antagonist: Preclinical Pharmacological and Clinical Data", Life Science, 1997, pp. 1129-1136, 60(13114). (Petition Paper 9, Exhibit 2004).
Callegari, E, et al., "A comprehensive non-clinical evaluation of the CNS penetration potential of antimuscarinic agents for the treatment of overactive bladder", British Journal of Clinical Pharmacology, 2011, pp-235-246, 72(2). (Petition Paper 9, Exhibit 2004).
Trial Transcript, *Pfizer Inc., et al.,* v. *Sandoz Inc., et al.*, C.A. No., 1;13/1110-GMS (D. Del. Jul. 13-16, 2015). (Petition Paper 9, Exhibit 2005).
Wein, A.J., Mundy, A.R., et al., "Urodynamics Principles, Practice and Application" Second Edition, 1994, pp. 43-70-"Pharmacologic treatment of voiding dysfunction". (Petition Paper 9, Exhibit 2008).
Detrol LA tolterodine tartrate extened release capsules. (Petition Paper 9, Exhibit 2009).
Krise, Jeffrey P., et al., "Novel Prodrug Approach for Tertiary Amines: Synthesis and Preliminary Evaluation of N-Phosphonooxymethyl Prodrugs", Journal of Medicinal Chemistry, 1999, pp. 3094-3100, vol. 42. (Petition Paper 9, Exhibit 2013).
Sinkul, A.A. et al., "Rationale for Design of Biologically Reversible Drug Derivatives: Prodrugs", Journal of Pharmaceutical Scienes, Feb. 1975, pp. 181-210, 64(2). (Petition Paper 9, Exhibit 2014).
Bundgaard, H, "Novel Chemical Approaches in Prodrug Design", Drugs of the Future, 1991, pp. 443-458, 16(5). (Petition Paper 9, Exhibit 2015).
Jann, Michael W., et al., Clinical Pharmacokinetics of the Deport Antipsychotics, Clinical Pharmacokinetics, 1985, pp. 315-333, vol. 10. (Petition Paper 9, Exhibit 2016).
Beresford, R., et al., "Haloperidol Decanoate A Preliminary Review of Its Pharmacodynamic and Pharmacokinetic Properties and Therapeutic Use in Psychosis", Drugs, 1987, pp. 31-49, vol. 33. (Petition Paper 17, Exhibit 2017).

(56) References Cited

OTHER PUBLICATIONS

*Mylan Pharmaceuticals Inc. and Mylan Laboratories Limited v. UCB Pharma GMBH*; IPR2016-00510-US6858650, Petition Owner's Response. (Petition Paper 20).
Transcript of the Deposition of Steven Patterson, Ph.D., dated Oct. 4, 2016, Case IPR2016-00510, Case IPR2016-00512, Case IPR2016-00514, Case IPR2016-00516, Case IPR2016-0517. (Petition Paper 17, Exhibit 2020).
Declaration of Hans Maag, Sc.D. (Petition Paper 17, Exhibit 2021).
Declaration William R. Roush, Ph.D. (Petition Paper 17 Exhibit 2022).
Declaration of Scott A. Macdiarmid, M.D., FRCPSC. (Petition Paper 17, Exhibit 2023).
Declaration of Leonard J. Chyall, Ph.D. (Petition Paper 17, Exhibit 2024).
Declaration Clause 0. Meese, Ph.D. (Petition Paper 17, Exhibit 2025).
Transcript of the Deposition of Gulley C. Carson III, M.D., dated Aug. 25, 2016, C.A. No. 15-cv-0079 (D. Del.). (Petition Paper 17, Exhibit 2026).
Transcript of the Deposition of David R. Janero, Ph.D., dated Aug. 16, 2016, C.A. No. 15-cv-0079 (D. Del.). (Petition Paper 17, Exhibit 2027).
Lin, Jiunn H., et al., "Role of Pharmacokinetics and Metabolism in Drug Discovery and Development", Pharmacological Reviews 407, 1997, pp. 433-449, 49(4). (Petition Paper 17, Exhibit 2028).
*Mylan Pharmaceuticals Inc. and Mylan Laboratories Limited v. UCB Pharma GMBH*; IPR2016-00514-US7855230, Petition Owner's Response. (Petition Paper 17).
Declaration Clause O. Meese, Ph.D. (Petition Paper 17, Exhibit 2025).
*Mylan Pharmaceuticals Inc. and Mylan Laboratories Limited v. UCB Pharma GMBH*; IPR2016-00517-US7985772, Petition Owner's Response. (Petition Paper 17).
Beresford, R., et al., "Haloperidol Decanoate a Preliminary Review of Its Pharmacodynamic and Pharmacokinetic Properties and Therapeutic Use in Psychosis", Drugs, 1987, pp. 31-49, vol. 33. (Petition Paper 9, Exhibit 2017).
Transcript of the Deposition of Steven Patterson, Ph.D., dated Oct. 4, 2016, Case IPR2016-00510, Case IPR2016-00512, Case IPR2016-00514, Case IPR2016-00516, Case IPR2016-0517. (Petition Paper 20, Exhibit 2020).
Declaration of Hans Maag, Sc.D. (Petition Paper 20, Exhibit 2021).
Declaration William R. Roush, Ph.D. (Petition Paper 20, Exhibit 2022).
Declaration of Scott A. Macdiarmid, M.D., FRCPSC. (Petition Paper 20, Exhibit 2023).
Declaration of Leonard J. Chyall, Ph.D. (Petition Paper 20, Exhibit 2024).
Declaration Clause O. Meese, Ph.D. (Petition Paper 20, Exhibit 2025).
Transcript of the Deposition of Gulley C. Carson III, M.D., dated Aug. 25, 2016, C.A. No. 15-cv-0079 (D. Del.). (Petition Paper 20, Exhibit 2026).
Transcript of the Deposition of David R. Janero, Ph.D., dated Aug. 16, 2016, Ca. No. 15-cv-0079 (D. Del.). (Petition Paper 20, Exhibit 2027).
Lin, Jiunn H., et al., "Role of Pharmacokinetics and Metabolism in Drug Discovery and Development", Pharmacological Reviews 407, 1997, pp. 433-449, 49(4). (Petition Paper 20, Exhibit 2028).
Brynne, N., et al., "Fluoxetine inhibits the metabolism of tolterodine-pharmacokinetic implications and proposed clincial relevance", British Journal of Clinical Pharmacol. 1999, pp. 553-563, vol. 48. (Petition Paper 17, Exhibit 2029).
CV Hans Maag. (Petition Paper 17, Exhibit 2030).
Wein, Alan, J., et al., "Pharmacologic Options for the Overactive Bladder", 51 Urology, Supplement to Feb. 1998, pp. 43-47, 51(Suppl 2A). (Petition Paper 17, Exhibit 2031).

Nilvebrant, Lisbeth, et al., "a new bladder-selective antimuscarinic agent" European Journal of Pharmacology, 1997, pp. 195-207, vol. 327. (Petition Paper 17 Exhibit 2032).
Fanati, J.A., et al., "Urinary Incontinence in Adults: Acute and Chronic Management, in Clinical Practice Guideline", 1996 Update, (U.S. Department of Health & Human Services, AHCPR Publication No. 96-0682, 1996). (Petition Paper 17, Exhibit 2033).
Madersbacher, H., et al., "Trospium Chloride versus Oxybutynin: A Randomized, Double-Blind, Multicentre Trial in the Treatment of Detrusor Hyper-Reflexia", British Journal of Urology, 1995, pp. 452-456, vol. 75. (Petition Paper 17, Exhibit 2034).
Schladitz-Keil, G., et al., "Determination of the Bioavailability of the Quaternary Compound Trospium Chloride in Man from Urinary Excretion Data", Arzneimittel Forschung/Drug Research, 1986, pp. 984-987, 36(1). (Petition Paper 17, Exhibit 2035).
Brynne, N., et al., "Fluoxetine inhibits the metabolism of tolterodine-pharmacokinetic implications and proposed clincial relevance", British Journal of Clinical Pharmacol. 1999, pp. 553-563, vol. 48. (Petition Paper 20, Exhibit 2029).
CV Hans Maag. (Petition Paper 20, Exhibit 2030).
Wein, Alan, J., et al., "Pharmacologic Options for the Overactive Bladder", 51 Urology, Supplement to Feb. 1998, pp. 43-47, 51(Suppl 2A). (Petition Paper 20, Exhibit 2031).
Nilvebrant, Lisbeth, et al., "a new bladder-selective antimuscarinic agent" European Journal of Pharmacology, 1997, pp. 195-207, vol. 327. (Petition Paper 20 Exhibit 2032).
Fanati, J.A., et al., "Urinary Incontinence in Adults: Acute and Chronic Management, in Clinical Practice Guideline", 1996 Update, (U.S. Department of Health & Human Services, AHCPR Publication No. 96-0682, 1996). (Petition Paper 20, Exhibit 2033).
Madersbacher, H., et al., "Trospium Chloride versus Oxybutynin: A Randomized, Double-Blind, Multicentre Trial in the Treatment of Detrusor Hyper-Reflexia", British Journal of Urology, 1995, pp. 452-456, vol. 75. (Petition Paper 20, Exhibit 2034).
Schladitz-Keil, G., et al., "Determination of the Bioavailability of the Quaternary Compound Trospium Chloride in Man from Urinary Excretion Data", Arzneimittel Forschung/Drug Research, 1986, pp. 984-987, 36(1). (Petition Paper 20, Exhibit 2035).
*Mylan Pharmaceutical Inc. and Mylan Laboratories Limited v. UCB Pharma GMBH*, IPR2016-00512-U.S. Pat. No. 7,384,980, Patent Owner Preliminary Response. (Petition Paper 9).
*Mylan Pharmaceutical Inc. and Mylan Laboratories Limited v. UCB Pharma GMBH*, IPR2016-00510 (U.S. Pat. No. 3,858,650), IPR2016-00512 (U.S. Pat. No. 7,384,980), IPR2016-00514 (U.S. Pat. No. 7,855,230), IPR2016-00516 (U.S. Pat. No. 3,338,478), IPR2016-00517 (U.S. Pat. No. 7,985,772); Order Conduct of Proceedings 37 C.F.R. § 42.5. (Petition Paper 11).
*Mylan Pharmaceutical Inc. and Mylan Laboratories Limited v. UCB Pharma GMBH*, U.S. Pat. No. 7,384,980, Decision Institution of Inter Partes Review 37 C.F.R. §42.108. (Petition Paper 12).
*Mylan Pharmaceutical Inc. and Mylan Laboratories Limited v. UCB Pharma GMBH*, IPR2016-00510 (U.S. Pat. No. 3,858,650), IPR2016-00512 (U.S. Pat. No. 7,384,980), IIPR2016-00517(U.S. Pat. No. 7,985,772); Scheduling Order. (Petition Paper 13).
*Mylan Pharmaceutical Inc. and Mylan Laboratories Limited v. UCB Pharma GMBH*, U.S. Pat. No. 7,384,980, Patent owner's Notice of Objections to Evidence 37 C.F.R. §42.64. (Petition Paper 14).
*Mylan Pharmaceutical Inc. a v. UCB Pharma GMBH*, U.S. Pat. No. 7,384,980, Petitioner's Mylan Pharmaceuticals Inc.'s Response to Patent Owner's Objections and Supplemental Evidence Pursuant to 37 C.F.R. §42.64(b)(2).(Petition Paper 15).
*Mylan Pharmaceutical Inc. and Mylan Laboratories Limited v. UCB Pharma GMBH*, U.S. Pat. No. 7,384,980, Patent owner's Notice of Deposition of Steven E. Patterson, Ph.D. (Petition Paper 16).
*Mylan Pharmaceutical Inc. and Mylan Laboratories Limited v. UCB Pharma GMBH*, IPR2016-00514-U.S. Pat. No. 7,855,230, Patent Owner Preliminary Response. (Petition Paper 9).
*Mylan Pharmaceutical Inc. and Mylan Laboratories Limited v. UCB Pharma GMBH*, U.S. Pat. No. 7,855,230, Decision Institution of Inter Partes Review 37 C.F.R. §42.108. (Petition Paper 12).

(56) References Cited

OTHER PUBLICATIONS

*Mylan Pharmaceutical Inc. and Mylan Laboratories Limited* v. *UCB Pharma GMBH*, IPR2016-00514-U.S. Pat. No.7,855,230; Scheduling Order. (Petition Paper 13).
*Mylan Pharmaceutical Inc. and Mylan Laboratories Limited* v. *UCB Pharma GMBH*, U.S. Pat. No. 7,855,230, Patent Owner's Notice of Objections to Evidence 37 C.F.R. §42.64. (Petition Paper 14).
*Mylan Pharmaceutical Inc. a* v. *UCB Pharma GMBH*, U.S. Pat. No. 7,855,230, Petitioner's Mylan Pharmaceuticals Inc.'s Response to Patent Owner's Objections and Supplemental Evidence Pursuant to 37 C.F.R. §42.64(b)(2). (Petition Paper 15).
*Mylan Pharmaceutical Inc. and Mylan Laboratories Limited* v. *UCB Pharma GMBH*, U.S. Pat. No. 7,855,230, Patent owner's Notice of Deposition of Steven E. Patterson, Ph.D. (Petition Paper 16).
*Mylan Pharmaceutical Inc.* v. *UCB Pharma GMBH*, U.S. Pat. No. 7,855,230, Petitioner's Objections to Patent Owner's Evidence Pursuant 37 C.F.R. §42.64. (Petition Paper 18).
*Mylan Pharmaceutical Inc. and Mylan Laboratories Limited* v. *UCB Pharma GMBH*, IPR2016-00514-U.S. Pat. No. 8,338,478, Patent Owner Preliminary Response. (Petition Paper 9).
*Mylan Pharmaceutical Inc. and Mylan Laboratories Limited* v. *UCB Pharma GMBH*, U.S. Pat. No. 8,338,478, Decision Institution of Inter Partes Review 37 C.F.R. §42.108. (Petition Paper 12).
*Mylan Pharmaceutical Inc. and Mylan Laboratories Limited* v. *UCB Pharma GMBH*, IPR2016-00514-US8338478; Scheduling Order. (Petition Paper 13).
*Mylan Pharmaceutical Inc. and Mylan Laboratories Limited* v. *UCB Pharma GMBH*, U.S. Pat. No. 8,338,478, Patent Owner's Notice of Objections to Evidence 37 C.F.R. §42.64. (Petition Paper 14).
*Mylan Pharmaceutical Inc. a* v. *UCB Pharma GMBH*, U.S. Pat. No. 8,338,478, Petitioner's Mylan Pharmaceuticals Inc.'s Response to Patent Owner's Objections and Supplemental Evidence Pursuant to 37 C.F.R. §42.64(b)(2). (Petition Paper 15).
*Mylan Pharmaceutical Inc. and Mylan Laboratories Limited* v. *UCB Pharma GMBH*, U.S. Pat. No. 8,338,478, Patent owner's Notice of Deposition of Steven E. Patterson, Ph.D. (Petition Paper 16).
*Mylan Pharmaceutical Inc.* v. *UCB Pharma GMBH*, U.S. Pat. No. 8,338,478, Petitioner's Objections to Patent Owner's Evidence Pursuant 37 C.F.R. §42.64. (Petition Paper 18).
*Mylan Pharmaceutical Inc. and Mylan Laboratories Limited* v. *UCB Pharma GMBH*, IPR2016-00514-U.S. Pat. No. 7,985,772, Patent Owner Preliminary Response. (Petition Paper 9).
*Mylan Pharmaceutical Inc. and Mylan Laboratories Limited* v. *UCB Pharma GMBH*, U.S. Pat. No. 7,985,772, Decision Institution of Inter Partes Review 37 C.F.R. §42.108. (Petition Paper 12).
*Mylan Pharmaceutical Inc. and Mylan Laboratories Limited* v. *UCB Pharma GMBH*, IPR2016-00514-US7985772; Scheduling Order. (Petition Paper 13).
*Mylan Pharmaceutical Inc. and Mylan Laboratories Limited* v. *UCB Pharma GMBH*, U.S. Pat. No. 7,985,772, Patent Owner's Notice of Objections to Evidence 37 C.F.R. §42.64. (Petition Paper 14).
*Mylan Pharmaceutical Inc. a* v. *UCB Pharma GMBH*, U.S. Pat. No. 7,985,772, Petitioner's Mylan Pharmaceuticals Inc.'s Response to Patent Owner's Objections and Supplemental Evidence Pursuant to 37 C.F.R. §42.64(b)(2). (Petition Paper 15).
*Mylan Pharmaceutical Inc. and Mylan Laboratories Limited* v. *UCB Pharma GMBH*, U.S. Pat. No. 7,985,772, Patent owner's Notice of Deposition of Steven E. Patterson, Ph.D. (Petition Paper 16).
*Mylan Pharmaceutical Inc.* v. *UCB Pharma GMBH*, U.S. Pat. No. 7,985,772, Petitioner's Objections to Patent Owner's Evidence Pursuant 37 C.F.R. §42.64. (Petition Paper 18).

\* cited by examiner

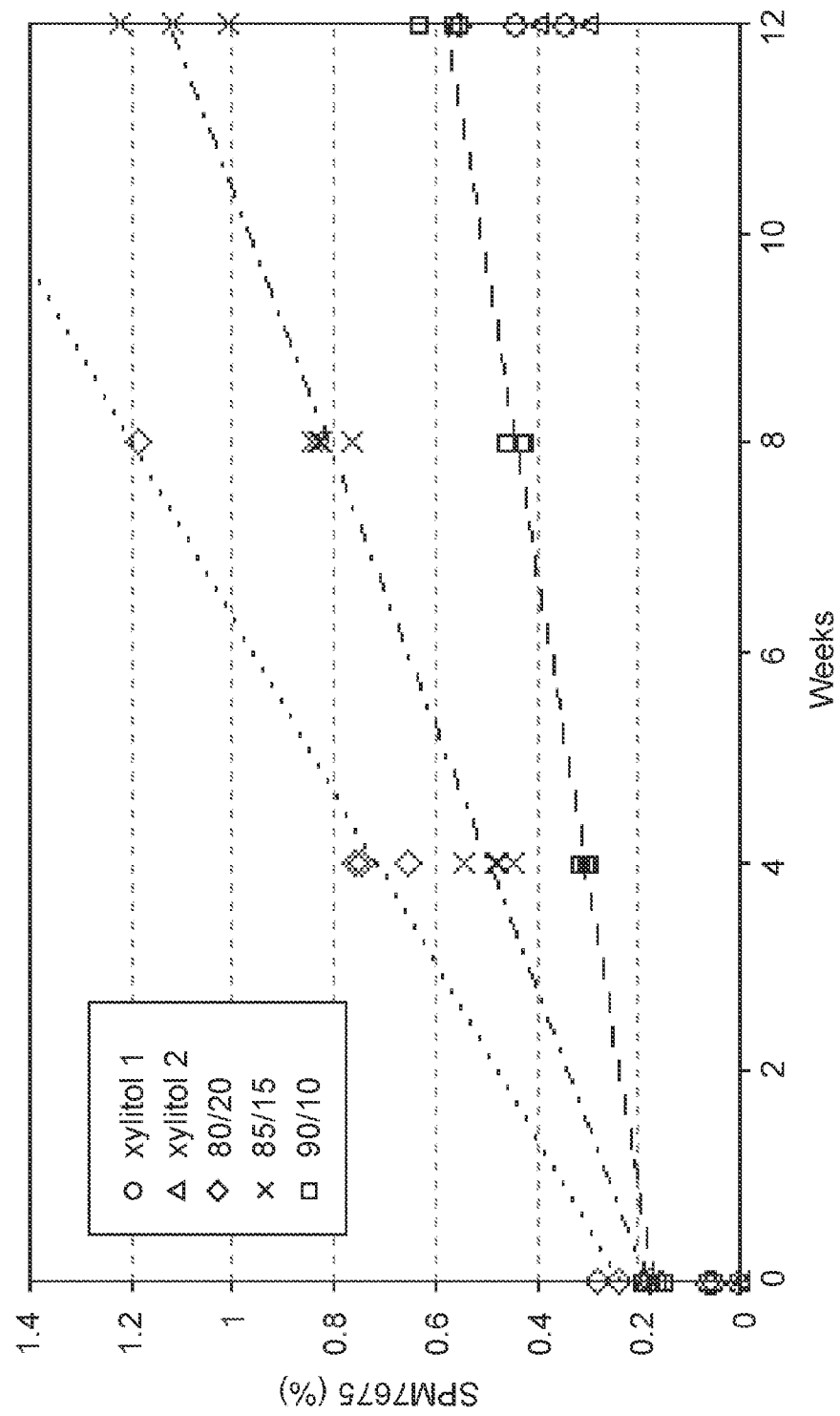

(a) crystalline fesoterodine hydrogen fumarate
(b) amorphous fesoterodine hydrogen fumarate
(c) HPMC- hypromellose-Methocel E5LV Fingerprint region of FIG. 2

Area for assessment from FIGS. 2 and 2A (a) crystalline fesoterodine hydrogen fumarate
(b) amorphous fesoterodine hydrogen fumarate
(c) IR layer from IR beads
(d) HPMC- hypromellose-Methocel E5LV (a) crystalline fesoterodine hydrogen fumarate
(b) amorphous fesoterodine hydrogen fumarate
(c) (d) and (e) IR layer from IR beads
(three different samples showing sample variability)
(f) HPMC- hypromellose-Methocel E5LV (a) crystalline fesoterodine hydrogen fumarate
(b) amorphous fesoterodine hydrogen fumarate
(c) IR layer from 10% MR beads
(d) HPMC- hypromellose-Methocel E5LV Absorbance/Wavenumber (cm-1)

(a) crystalline fesoterodine hydrogen fumarate
(b) amorphous fesoterodine hydrogen fumarate
(c) and (d) IR layer from 10% MR beads
    (two different samples showing sample variability)
(e) HPMC- hypromellose-Methocel E5LV (a) crystalline fesoterodine hydrogen fumarate
(b) amorphous fesoterodine hydrogen fumarate
(c) IR layer from 20% MR beads
(d) HPMC- hypromellose-Methocel E5LV (a) crystalline fesoterodine hydrogen fumarate
(b) amorphous fesoterodine hydrogen fumarate
(c) and (d) IR layer from 20% MR beads (two different samples showing sample variability)
(d) HPMC- hypromellose-Methocel E5LV Absorbance/Wavenumber (cm-1)

(a) crystalline fesoterodine hydrogen fumarate
(b) amorphous fesoterodine hydrogen fumarate
(c) HPMC- hypromellose-Methocel E5LV
(d) Lactose (Pharmatose 110 mesh)

Fingerprint region of FIG. 6

Area for assessment from FIGS. 6 and 6A (a) crystalline fesoterodine hydrogen fumarate
(b) amorphous fesoterodine hydrogen fumarate
(c) 1:9 weight % fesoterodine hydrogen fumarate/HPMC on lactose particles
(d) HPMC- hypromellose- (Methocel E5LV)
(e) Lactose (Pharmatose 110 mesh)

(a) crystalline fesoterodine hydrogen fumarate
(b) amorphous fesoterodine hydrogen fumarate
(c) (d) and (e) 1:9 weight % fesoterodine hydrogen fumarate/HPMC
on lactose particles (three different samples showing sample variability)
(f) HPMC- hypromellose- (Methocel E5LV)
(g) Lactose (Pharmatose 110 mesh)

(a) crystalline fesoterodine hydrogen fumarate
(b) amorphous fesoterodine hydrogen fumarate
(c) 1:9 weight % fesoterodine hydrogen fumarate/HPMC on lactose particles
(d) HPMC- hypromellose- (Methocel E5LV)
(e) Lactose (Pharmatose 110 mesh)

(a) crystalline fesoterodine hydrogen fumarate
(b) amorphous fesoterodine hydrogen fumarate
(c) (d) and (e) 1:9 weight % fesoterodine hydrogen fumarate/HPMC on lactose particles (three different samples showing sample variability)
(f) HPMC- hypromellose- (Methocel E5LV)
(g) Lactose (Pharmatose 110 mesh)

SOLID MOLECULAR DISPERSION OF FESOTERODINE HYDROGEN FUMARATE AND POLYMERIC BINDER

This application is a national stage application under 35 U.S.C. 371 of PCT/IB2012/050225, filed on Jan. 17, 2012, which claims the benefit of U.S. Provisional Patent Application No. 61/433,743, filed on Jan. 18, 2011, the disclosures of which are hereby incorporated by reference in their entirety.

The present invention relates to a solid dispersion comprising from 3:97 to 12:88 weight % ratio of fesoterodine hydrogen fumarate:an alkyl hydroxyalkylcellulose ether or a hydroxyalkylcellulose ether, or an ester of either thereof, or a mixture of any two or more thereof, in which the fesoterodine hydrogen fumarate is stabilised in the dispersion in a form not corresponding to its crystalline or amorphous form.

The present dispersion achieves comparable or improved chemical stability in respect of the fesoterodine hydrogen fumarate component to that observed for the commercial xylitol-based tablet formulation, in particular by minimising the levels of the two primary degradation products SPM7605 and SPM7675. The present dispersion is believed to achieve this stabilising effect as it displays the characteristics of a solid molecular dispersion.

Preferably, the present invention relates to a solid molecular dispersion comprising from 3:97 to 12:88 weight % ratio of fesoterodine hydrogen fumarate:an alkyl hydroxyalkylcellulose ether or a hydroxyalkylcellulose ether, or an ester of either thereof, or a mixture of any two or more thereof.

The invention also relates to an inert core bead or particle which is coated with said dispersion, to modified-release coating of such a bead or particle, and to a pharmaceutical capsule formulation comprising such coated beads or particles.

The invention further relates to an inert core bead or particle which is coated with said dispersion and to the manufacture of pharmaceutical tablets comprising such beads or particles.

Fesoterodine, that is 2-[(1R)-3-(diisopropylamino)-1-phenylpropyl]-4-(hydroxymethyl)phenyl isobutyrate, R-(+)-2-(3-(diisopropylamino-1-phenylpropyl)-4-hydroxymethyl-phenyl isobutyrate or R-(+)-isobutyric acid 2-(3-diisopropylamino-1-phenylpropyl)-4-hydroxymethylphenyl ester, has the following chemical structure:

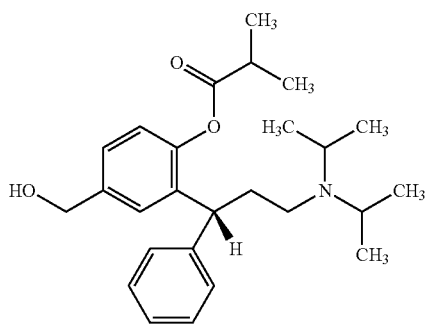 [SMILES: CC(C)C(=O)Oc1ccc(CO)cc1[C@H](CCN(C(C)C)C(C)C)c1ccccc1]

Fesoterodine and its physiologically acceptable acid salts are disclosed in WO99/58478 for use as antimuscarinic agents that are useful for the treatment of, inter alia, urinary incontinence.

Fesoterodine hydrogen fumarate is disclosed in WO01/35957A1 and U.S. Pat. No. 6,858,650 B1 as a preferred crystalline, physiologically compatible, acid addition salt form of fesoterodine.

Fesoterodine per se has only been previously prepared as an unstable oil which presents difficulty for pharmaceutical formulation, processing and use.

Fesoterodine hydrogen fumarate per se is crystalline and is suitable for pharmaceutical formulation and processing but it requires refrigeration in order to maintain adequate stability on storage for pharmaceutical use.

WO2007/141298A1 discloses pharmaceutical compositions comprising fesoterodine, or a pharmaceutically acceptable salt thereof, and a pharmaceutically acceptable stabiliser selected from xylitol, sorbitol, polydextrose, isomalt, dextrose, and combinations thereof. Such compositions are suitable for the manufacture of tablets and preferred tablet compositions described include those comprising fesoterodine hydrogen fumarate, hydroxypropyl methyl cellulose (HPMC) and xylitol which have shown excellent stability on tablet storage under ambient conditions for over 2 years. Indeed, a tablet composition comprising fesoterodine hydrogen fumarate, hydroxypropyl methyl cellulose (HPMC) and xylitol is the drug formulation that is used commercially in view of its acceptable shelf-life. The commercial 4 mg dose formulation is described in WO2007/141298A1 on page 44, Table 1, Example C, and the commercial 8 mg dose formulation on page 45, Table 2, Example H. Studies have shown that the presence of a stabiliser such as xylitol is essential to achieve a pharmaceutically acceptable stability profile.

WO2010/043408 describes microencapsulated fesoterodine formulations but does not disclose formulations containing fesoterodine or a salt thereof, in combination with a polymeric binder, or a solid molecular dispersion thereof.

There is a need for further stable pharmaceutically acceptable formulations comprising fesoterodine hydrogen fumarate. More particularly, there is a need for a further stable formulation comprising fesoterodine hydrogen fumarate that has comparable, or improved, stability on storage than the current xylitol-based tablet formulation that is sold commercially in which the fesoterodine hydrogen fumarate exists in a crystalline form.

BRIEF DESCRIPTION OF THE DRAWINGS

FIG. 1B depicts a summary plot showing the levels of SPM 7675 observed on the IR beads (90:10, 85:15 and 80:20 weight % hydroxypropyl methylcellulose—Methocel E5 LV™:fesoterodine hydrogen fumarate) and the commercial tablet formulation (Xylitol 1 and 2) when stored at 40° C./75% RH.

Figure 1A:
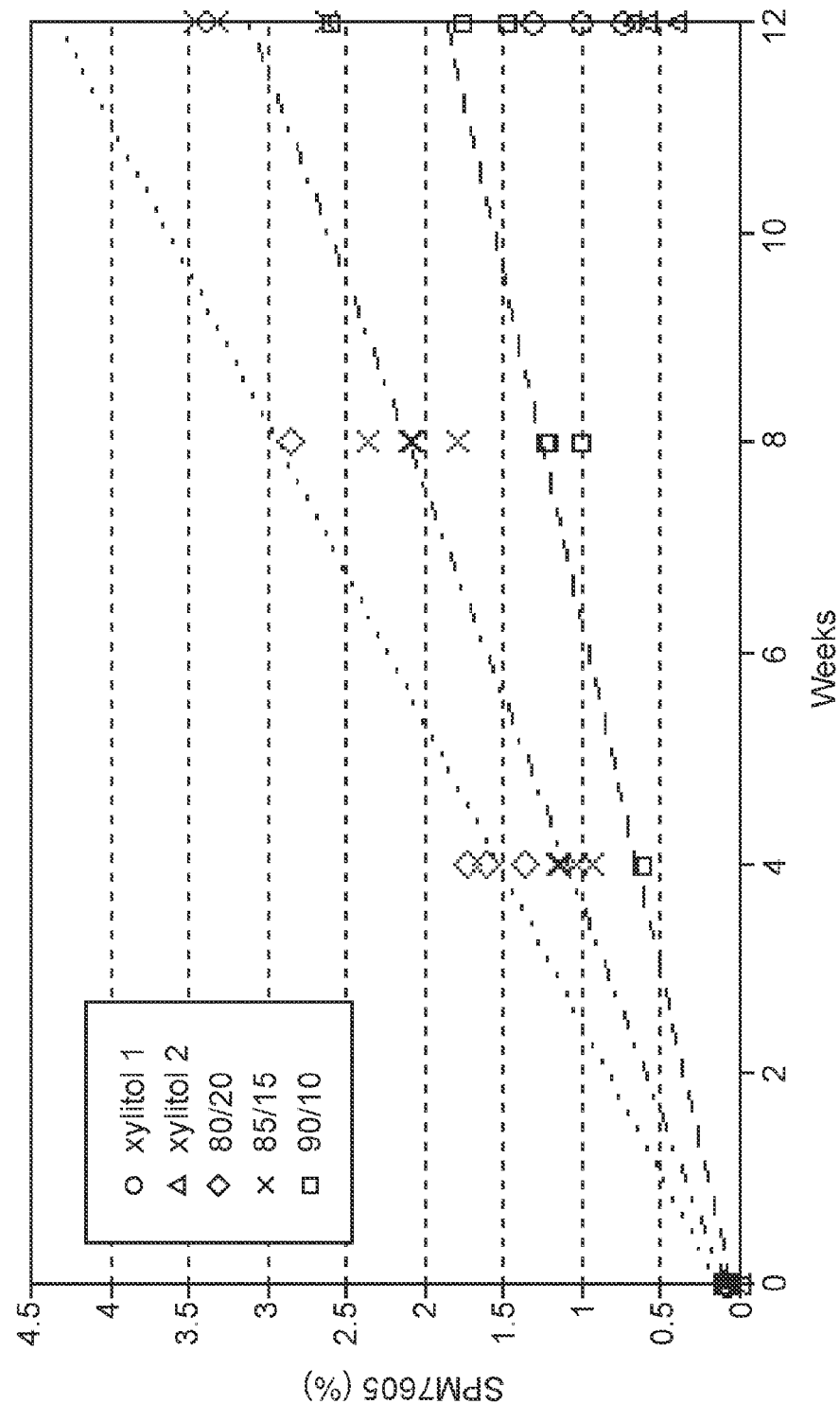
FIG. 1A depicts a summary plot showing the levels of SPM 7605 observed on the IR beads (90:10, 85:15 and 80:20 weight % hydroxypropyl methylcellulose—Methocel E5 LV™:fesoterodine hydrogen fumarate) and the commercial tablet formulation (Xylitol 1 and 2) when stored at 40° C./75% RH.

It has now been found that a pharmaceutical formulation comprising a solid dispersion comprising from 3:97 to 12:88 weight % ratio of fesoterodine hydrogen fumarate:an alkyl hydroxyalkylcellulose ether or a hydroxyalkylcellulose ether, or an ester of either thereof, or a mixture of any two or more thereof, in which the fesoterodine hydrogen fumarate is not in crystalline or amorphous form in said dispersion, has comparable or improved stability on storage to the commercial xylitol-based tablet formulation described above. Without wishing to be bound by theory, it is believed that there exists a solid molecular dispersion of fesoterodine hydrogen fumarate in an alkyl hydroxyalkylcellulose ether or a hydroxyalkylcellulose ether, or an ester of either thereof, or a mixture of any two or more thereof, in said dispersion.

As such, it has now been found that a pharmaceutical formulation comprising a solid molecular dispersion comprising from 3:97 to 12:88 weight % ratio of fesoterodine hydrogen fumarate:an alkyl hydroxyalkylcellulose ether or a hydroxyalkylcellulose ether, or an ester of either thereof, or a mixture of any two or more thereof, has comparable or improved stability on storage to the commercial xylitol-based tablet formulation. The observed stability is directly attributable to the solid molecular dispersion present in the formulation. This finding is unexpected in that it has been surprisingly found that fesoterodine hydrogen fumarate can be stabilised in the presence of a polymeric binder (e.g. HPMC) but in the absence of a stabiliser such as xylitol. Such a pharmaceutical formulation is particularly suitable for development as a modified release, bead-in-capsule formulation of the drug for paediatric use, or for the manufacture of pharmaceutical tablets.

The term "solid dispersion" refers to a group of solid materials comprising at least two different components, generally a polymeric matrix and a drug. The matrix can be either crystalline or amorphous. The drug molecules can be dispersed throughout the matrix as particles composed of amorphous molecular clusters, or as crystals (highly ordered 3D-molecular arrangement), of the drug. Alternatively, if the drug is dispersed within the matrix at the molecular level then this is termed a "solid molecular dispersion". In a solid molecular dispersion the predominant intermolecular interaction is defined as being between each drug molecule and each polymer molecule, even if the drug molecules are present as (e.g.) molecular dimers in the solid molecular dispersion. What is essential is that each drug molecule predominantly interacts with a polymeric matrix environment. For a summary of the characteristics of solid dispersion systems see "*Pharmaceutical applications of solid dispersion systems*", Chiou W L, Riegelman S, Journal of Pharmaceutical Sciences (1971), 60(9), 1281-1302.

The present invention relates to a solid molecular dispersion comprising from 3:97 to 12:88 weight % ratio of fesoterodine hydrogen fumarate:an alkyl hydroxyalkylcellulose ether or a hydroxyalkylcellulose ether, or an ester of either thereof, or a mixture of any two or more thereof.

More preferably, the solid molecular dispersion comprises about either a 1:9 or 1:19 weight % ratio of fesoterodine hydrogen fumarate:an alkyl hydroxyalkylcellulose ether or a hydroxyalkylcellulose ether, or an ester of either thereof, or a mixture of any two or more thereof.

Most preferably, the solid molecular dispersion consists essentially of about a 1:9 or 1:19 weight % ratio of fesoterodine hydrogen fumarate:an alkyl hydroxyalkylcellulose ether or a hydroxyalkylcellulose ether, or an ester of either thereof, or a mixture of any two or more thereof.

The alkyl hydroxyalkylcellulose ether or the hydroxyalkylcellulose ether, or an ester of either thereof, that is used as a component of the dispersion is classified as a polymeric binder. A polymeric binder is defined as a pharmaceutically acceptable material consisting of a polymeric material that is generally used to promote adhesion of a drug to itself or to another formulation component, such as the surface of an inert core bead or particle. Typical polymeric binders used in drug layering operations are water soluble to allow application of the mixture of drug and polymeric binder in an aqueous solution, although water insoluble binders can also be used, as appropriate.

The polymeric binder used in the present invention is an alkyl hydroxyalkylcellulose ether or a hydroxyalkylcellulose ether, or an ester of either thereof, or a mixture of any two or more thereof (referred to herein as the "cellulose ether component") (see Encyclopaedia of Polymer Science and Technology, John Wiley & Sons, Inc., Vol. 5, 507-532, "Cellulose Ethers" (2002) for general information on cellulose ethers).

Examples of an alkyl hydroxyalkylcellulose ether are hydroxypropyl methyl cellulose (HPMC, compendium name=hypromellose, e.g., Methocel E3 or E5—trade marks), hydroxyethyl methyl cellulose (HEMC) and hydroxybutyl methyl cellulose (HBMC).

Examples of a hydroxyalkylcellulose ether are hydroxyethylcellulose (HEC) and hydroxypropylcellulose (HPC).

An example of an ester of an alkyl hydroxyalkylcellulose ether is hydroxypropyl methyl cellulose acetate succinate (HPMCAS) (see Pharmaceutical Research, 26(6), 1419-1431 (2009).

Most preferably, hydroxypropyl methyl cellulose (e.g. Methocel E5 LV—trade mark) is used as the sole cellulose ether component.

The present solid dispersion/solid molecular dispersion may be prepared by first preparing a solution of fesoterodine hydrogen fumarate and the alkyl hydroxyalkylcellulose ether or hydroxyalkylcellulose ether, or an ester of either thereof, or a mixture of any two or more thereof, e.g. hydroxypropyl methyl cellulose alone, in a suitable solvent, e.g. water. This solution may be applied to inert core beads or particles and then the coated inert core beads or particles dried to form immediate-release (IR) beads or particles/granules. Fluid bed coating of the spouted fluid bed type assisted with a draft tube (such as fluid bed Wurster coating) or tumbling fluid bed coating (such as rotary or tangential granulation) can be used for the coating process (see, e.g., Fukumori, Yoshinobu and Ichikawa, Hideki (2006) 'Fluid Bed Processes for Forming Functional Particles', Encyclopedia of Pharmaceutical Technology, 1: 1, 1773-1778). Preferably, the fluid-bed coating is conducted using a fluid-bed coater in Wurster configuration.

Such inert core beads or particles are preferably comprised of a water-soluble or -swellable material and may be any such material that is conventionally used as inert core beads or particles or any other pharmaceutically acceptable water-soluble or water-swellable material that can be made into core beads, particles or pellets. Preferably, the inert core beads or particles are spheres of sucrose/starch (Sugar Spheres NF—trade mark) or sucrose crystals, or are extruded and dried spheres comprised of excipients such as microcrystalline cellulose or lactose. Preferably, the inert core beads or particles are comprised of microcrystalline cellulose alone or in combination with one or more sugars, or are comprised of lactose. Yet more preferably, the inert core beads or particles are comprised of microcrystalline cellulose or lactose alone. Most preferably, the inert core beads or particles are Celphere (trade mark—Asahi Kasei) microcrystalline cellulose spheres of CP-507 grade with a 500-710 micron diameter, or lactose, e.g. Pharmatose 110M (trade mark).

The immediate-release (IR) beads or particles/granules obtained may be coated with a modified-release (MR) layer that provides acceptable control of the release rate of fesoterodine in a patient.

The modified-release layer may be a sustained-release (SR) coating which is designed to release the drug at a steady rate. The sustained-release coating may be a polymer coating such as a cellulose ester, a cellulose ether or an acrylic polymer, or a mixture of any thereof. Preferred coatings include ethyl cellulose, cellulose acetate or cellulose acetate butyrate, or a mixture of any thereof. The coating may be applied as a solution in an organic solvent or as an aqueous dispersion or latex. The coating may be applied using a fluid bed coater, a Wurster coater or a rotary bed coater. If desired the permeability of the coating may be adjusted by blending 2 or more of such coating materials. The porosity of the coating may be tailored by adding a pre-determined amount of a finely-divided, water-soluble material, such as a sugar, salt or water-soluble polymer (e.g. hydroxypropyl cellulose, hydroxypropyl methyl cellulose), to a solution or dispersion of the membrane-forming polymer to be used. When the dosage form resulting is ingested into the aqueous medium of the gastro-intestinal tract, these water-soluble additives are leached out of the membrane, leaving pores which facilitate release of the drug. The membrane coating can also be modified by the addition of a plasticiser such as diethyl phthalate, polyethyleneglycol-400, triacetin, triacetin citrate or propylene glycol. Most preferably, the sustained release coating comprises ethyl cellulose (e.g. Ethocel Standard 10 Premium—trade mark) in combination with hydroxypropylcellulose (e.g. Klucel EF—trade mark) as a pore former.

In a preferred embodiment of the invention, the modified/sustained-release coating is achieved by first preparing a solution of the selected MR/SR components (e.g. ethylcellulose and hydroxypropylcellulose) in a suitable solvent, e.g. aqueous isopropanol, and, secondly, by applying this solution to the IR beads or particles/granules, e.g. using a fluid bed coater as described above (e.g. using a fluid-bed coater in Wurster configuration), and drying the resulting MR/SR-coated beads or particles/granules. The composition and thickness of the MR/SR coating may be varied to achieve the desired drug release profile.

The modified-release layer may be a delayed-release coating which is designed, on dosage form ingestion, to incorporate a delay in time before the onset of drug release. The delayed-release coating may be a pH-sensitive polymer such as cellulose acetate phthalate, cellulose acetate trimellitate, hydroxypropyl methyl cellulose phthalate, polyvinyl acetate phthalate, or may be an anionic acrylic copolymer of methacrylic acid and methyl methacrylate such as those available from RohmPharma, e.g. EUDRAGIT L-100 (trade mark), EUDRAGIT L-30 D-55 (trade mark), EUDRAGIT S-100 (trade mark) or EUDRAGIT FS 30D (trade mark), or a mixture of any thereof. The thickness and composition of the delayed-release coating may be adjusted to give the desired delayed-release properties. In general, thicker coatings are more resistant to erosion and, consequently, provide a longer delay in the release of the drug, as do coatings which are designed to dissolve above ph 7.

Typical IR and MR layer coating thicknesses used for the purposes of the present invention are as follows:
IR layer—10-100 micrometers, preferably 25-30 micrometers
MR layer—10-100 micrometers, preferably 10-15, 15-20 or 20-25 micrometers.

The IR or MR beads or particles/granules according to the invention may be filled into drug capsules by conventional techniques. Preferably, gelatin or hydroxypropyl methyl cellulose capsules are used for pharmaceutical formulation purposes.

Alternatively, the immediate-release beads or particles/granules obtained may be formed into pharmaceutical tablet formulations by conventional techniques.

The solid dispersion, the solid molecular dispersion, the IR/MR beads or particles/granules coated therewith, and the pharmaceutical formulations of the invention, may be used as medicaments. In particular, they may be used for the treatment of incontinence, preferably urinary incontinence. Most preferably, they may used for the treatment of urge urinary incontinence or mixed urinary incontinence.

The invention also provides a solid molecular dispersion obtainable by (a) achieving a solution of fesoterodine hydrogen fumarate and an alkyl hydroxyalkylcellulose ether or a hydroxyalkylcellulose ether, or an ester of either thereof, or a mixture of any two or more thereof, in from 3:97 to 12:88 weight % ratio, and (b) by drying to form said dispersion.

The following Examples illustrate the invention:

EXAMPLE 1

Preparation of a Solution of Fesoterodine Hydrogen Fumarate and HPMC (Hypromellose)

| Component | Quantity/unit; (g/kg) |
| --- | --- |
| Fesoterodine hydrogen fumarate | 30.069* |
| Hypromellose (Methocel E5 LV) | 270.630* |
| Sterile water for irrigation (to be removed in manufacturing process and does not appear in final product) | 3995.000* |

(*quantities based on dry finished product with no overage. Can incorporate 10% overage of the quantities of the coating materials to allow for in-process loss due to tubing volumes, coating of containers, etc.)

Set-up an overhead stirrer and impeller.
Weigh out 90% of water into an appropriate sized vessel.
Set the agitator speed to produce a suitable vortex and gradually add the hypromellose to the water and mix for at least 4 hours, preferably overnight, ensuring the solution does not foam. Cover to prevent evaporation while stirring (ensure there are no lumps after stirring).
Set-up an overhead stirrer and impeller. Weigh out the remaining 10% water into an appropriately sized vessel and add fesoterodine hydrogen fumarate under agitation. Mix for 10 minutes or until the fesoterodine hydrogen fumarate is fully dissolved. Cover to prevent evaporation while stirring.
Add the fesoterodine hydrogen fumarate solution to the hypromellose solution under agitation.
Mix for a minimum of 10 minutes or until all lumps have dissolved.
Determine the quantity of liquid lost due to evaporation. Replace lost liquid with water, rinsing out the fesoterodine hydrogen fumarate solution-containing vessel.
Ensure that the solution prepared is protected from sunlight at all times.

EXAMPLE 2

Preparation of a Solid Molecular Dispersion of Fesoterodine Hydrogen Fumarate and HPMC (Hypromellose) on Microcrystalline Cellulose Beads Using Glatt GPCG 1.1 Coater (Fesoterodine Hydrogen Fumarate Immediate Release (IR) Beads)

Heat Glatt GPCG 1.1 in 6" Wurster configuration to a product temp of ~56° C.
Quickly charge the microcrystalline cellulose spheres (500-710 μm) (Celphere CP-507) (699.301 g/kg—quantity based on dry finished product with no overage. Can incorporate 10% overage of the quantity to allow for in-process loss due to tubing volumes, coating of containers, etc.) into the fluidising chamber of the Glatt GPCG 1.1 coater.
Once the beads are fully fluidised commence spraying within 1 minute.
Example target coating conditions for the Glatt GPCG 1.1:
Airflow: 80 m$^3$/hr (Set)
Inlet Air Temperature: 80° C. (Set)
Atomisation Pressure: 2.0 Bar (Set)
Maximum Spray rate: 12 g/min
Nozzle diameter: 1.2 mm
Wurster Gap: 20 mm
Filters: Socks (20 μm mesh)
Filter shake: 15 secs every 5 mins
Tubing: Silicon, 0.125" ID×0.062" wall
Pump: Watson Marlow 505Du peristaltic
Commence spraying at ~7 g/min (3.9 rpm), after 10 minutes increase the spray rate to ~10 g/min (5.6 rpm). After an additional 10 minutes ramp up the spray rate to ~12 g/min (6.9 rpm).
The product temperature during coating (at/near maximum spray rate in steady state) should be approximately 50° C.
Continue spraying until all the theoretical quantity of coating solution has been sprayed onto the beads.
Cover the solution to prevent evaporation while coating.
After coating, dry the beads by allowing the product temperature to rise by 2° C. before shutting down the fluidisation air & heat.
The beads should be sieved through an 850 μm sieve to screen out agglomerates.

EXAMPLE 3

Preparation of a Solid Molecular Dispersion of Fesoterodine Hydrogen Fumarate and HPMC (Hypromellose) on Microcrystalline Cellulose Beads Using Glatt GPCG 3.1 Coater (Fesoterodine Hydrogen Fumarate Immediate Release (IR) Beads)

Heat Glatt GPCG 3.1 in 6" Wurster configuration to a product temp of ~56° C.

Quickly charge the microcrystalline cellulose spheres (500-710 µm) (Celphere CP-507) (699.301 g/kg—quantity based on dry finished product with no overage. Can incorporate 10% overage of the quantity to allow for in-process loss due to tubing volumes, coating of containers, etc.) into the fluidising chamber of Glatt GPCG 3.1 coater.

Example target coating conditions for the Glatt GPCG 3.1:
Airflow: 50 CFM
Inlet Air Temperature: 75° C. (Set)
Atomisation Pressure: 2.0 Bar (Set)
Maximum Spray rate: ~13.5 g/min
Inlet Air Dew Point: 15° C.
Nozzle diameter: 1.2 mm
Wurster Gap/Partition Height: 30 mm
Filters: Socks (20 µm mesh)
Filter shake: 15 secs every 5 mins
Tubing: Silicon, 0.125" ID×0.062" wall
Pump: Peristaltic Commence spraying at ~8 g/min, after 10 minutes increase the spray rate to ~10 g/min. After an additional 10 minutes ramp up the spray rate to ~12 g/min.

After 1 hour the spray rate can be increased to ~13.5 g/min if the process appears stable with low agglomeration levels.

The product temperature during coating (at/near maximum spray rate in steady state) should be approximately 50° C.

Continue spraying until all the theoretical quantity of coating solution has been sprayed onto the beads.

Cover the solution to prevent evaporation while coating.

After coating, dry the beads by allowing the product temperature to rise by 2° C. before shutting down the fluidisation air & heat.

The beads should be sieved through an 850 µm (20 Mesh) sieve to screen out agglomerates.

EXAMPLE 4

Preparation of 10% (w/w of Final Bead) Modified Release (MR) Fesoterodine Hydrogen Fumarate Beads

| Component | Quantity/unit: (g/kg) (Quantities based on dry finished product and do not include overages) |
|---|---|
| Fesoterodine hydrogen fumarate immediate release (IR) beads (Example 2 or Example 3) | 900.000 |
| Ethylcellulose (Ethocel Standard 10 Premium) | 80.000 |
| Hydroxypropylcellulose (Klucel EF) | 20.000 |
| Isopropyl alcohol (to be removed in manufacturing process and does not appear in final product) | 1327.474 |
| Sterile water for irrigation (to be removed in manufacturing process and does not appear in final product) | 181.019 |
| TOTAL | 1000.000 |

(a) Modified Release Solution Preparation

Calculate MR solution components with 10% overage (all components except fesoterodine hydrogen fumarate immediate release beads).

| | Overall solution - theoretical | Overall solution - 10% overage | Ethylcellulose solution | Hydroxypropylcellulose solution |
|---|---|---|---|---|
| Ethylcellulose | a | A | A | |
| Hydroxypropylcellulose | b | B | | B |
| Isopropyl alcohol | c | C | F-A-G | F-B-G |
| Water | d | D | G | G |
| Total | a + b + c + d = e | E | F | F |
| Half total | | E/2 = F | | |
| Half water | | D/2 = G | | |

Set-up an overhead stirrer and impeller.

Weigh out the required quantity of isopropyl alcohol and 50% of the water into an appropriate sized vessel.

Set the agitator speed to produce a suitable vortex and gradually add the ethylcellulose to the water and mix for at least 4 hours, ensuring the mixture does not foam.

Cover to prevent evaporation while stirring (ensure there are no lumps once stirring has finished).

Set-up an overhead stirrer and impeller.

Weigh out the remaining quantity of isopropyl alcohol and 50% of the water into an appropriate sized vessel.

Set the agitator speed to produce a suitable vortex and gradually add the hydroxypropylcellulose to the water and mix for at least 4 hours.

Cover to prevent evaporation while stirring.

Add the hydroxypropylcellulose solution to the ethylcellulose solution under agitation. Mix for 10 minutes.

Determine the quantity of liquid lost due to evaporation. Replace lost liquid with an isopropyl alcohol/water (88:12) solution, rinsing out the hydroxypropylcellulose-containing vessel, and mix for 10 mins.

Cover to prevent evaporation.

(b) Coating of IR Beads with Modified Release Layer

Coating Using Glatt GPCG 1.1 Fluid Bed Coater

Heat Glatt GPCG 1.1 in 6" Wurster configuration to a product temperature of ~40° C.

Quickly charge the fesoterodine hydrogen fumarate immediate release beads into the fluidising chamber of the Glatt GPCG 1.1 fluid bed coater.

Pre-heat the spheres to ~46° C.

Coat the spheres with the modified release solution (Step (a)) under the following target conditions:
Airflow: 80 m³/hr (Set)
Inlet Air Temperature: 50° C. (Set)
Atomisation Pressure: 2.0 Bar (Set)
Maximum Spray rate: 13.5 g/min Nozzle diameter: 1.2 mm
Wurster Gap: 20 mm
Filters: Bonnets (0.4 mm mesh)
Filter shake: 15 secs every 5 mins
Tubing: Silicon, 0.125" ID×0.062" wall
Pump: Watson Marlow 505Du peristaltic
Commence spraying at ~9.5 g/min (approximately 6 rpm), after 5 minutes increase the spray rate to ~11.5 g/min (approximately 7 rpm). After an additional 5 minutes ramp up the spray rate to ~13.5 g/min (approximately 8 rpm).
The pump rate can be adjusted as necessary to achieve the required spray rates.
The product temperature during coating (at/near maximum spray rate in steady state) should be approximately 39° C.
Continue spraying until all the theoretical quantity of modified release solution has been sprayed onto the beads.
Cover the solution to prevent evaporation during spraying.
After coating, dry the beads by allowing the product temperature to rise by 2° C. before shutting down the fluidisation air & heat.
The beads should be sieved through a 1000 μm sieve (or US Standard 18 Mesh) to screen out agglomerates.
(c) Coating of IR Beads with Modified Release Layer Coating Using Glatt GPCG 3.1 Fluid Bed Coater
Heat Glatt GPCG 3.1 in 6" Wurster configuration to a product temperature of ~40° C.
Quickly charge the fesoterodine hydrogen fumarate immediate release beads into the fluidising chamber of the Glatt GPCG 3.1 fluid bed coater.
Coat the spheres with the modified release solution (Step (a)) under the following target conditions:
Airflow: 50 CFM
Inlet Air Temperature: 50° C. (Set)
Atomisation Pressure: 2.0 Bar (Set)
Maximum Spray rate: 16 g/min
Inlet Air Dew Point: 15° C.
Nozzle diameter: 1.2 mm
Wurster Gap/Partition height: 30 mm
Filters: Bonnets (0.4 mm mesh)
Filter shake: 15 secs every 5 mins
Tubing: Silicon, 0.125" ID×0.062" wall
Pump: Peristaltic
Commence spraying at ~11.0 g/min, after 5 minutes increase the spray rate to ~14.0 g/min. After an additional 5 minutes ramp up the spray rate to ~16.0 g/min.
The product temperature during coating (at/near maximum spray rate in steady state) should be approximately 39° C.
Continue spraying until all the theoretical quantity of coating solution has been sprayed onto the beads.
Cover the solution to prevent evaporation during spraying.
After coating, dry the beads by allowing the product temperature to rise by 2° C. before shutting down the fluidisation air & heat.
The beads should be sieved through a 1000 μm sieve (or US Standard 18 Mesh) to screen out agglomerates.

EXAMPLE 5

Preparation of 15% (w/w of Final Bead) Modified Release (MR) Fesoterodine Hydrogen Fumarate Beads These are prepared by a similar process to that of Example 4 using the following components.

| Component | Quantity/unit: (g/kg) (Quantities based on dry finished product and does not include overages) |
|---|---|
| Fesoterodine hydrogen fumarate immediate release (IR) beads (Example 2 or Example 3) | 850.000 |
| Ethylcellulose (Ethocel Standard 10 Premium) | 120.000 |
| Hydroxypropylcellulose (Klucel EF) | 30.000 |
| Isopropyl alcohol (to be removed in manufacturing process and does not appear in final product) | 1991.211 |
| Sterile water for irrigation (to be removed in manufacturing process and does not appear in final product) | 271.529 |
| TOTAL | 1000.000 |

EXAMPLE 6

Preparation of 20% (w/w of Final Bead) Modified Release (MR) Fesoterodine Hydrogen Fumarate Beads These are prepared by a similar process to that of Example 4 using the following components.

| Component | Quantity/unit: (g/kg) (Quantities based on dry finished product and does not include overages) |
|---|---|
| Fesoterodine hydrogen fumarate immediate release (IR) beads (Example 2 or Example 3) | 800.000 |
| Ethyl cellulose (Ethocel Standard 10 Premium) | 160.000 |
| Hydroxypropylcellulose (Klucel EF) | 40.000 |
| Isopropyl alcohol (to be removed in manufacturing process and does not appear in final product) | 2654.942 |
| Sterile water for irrigation (to be removed in manufacturing process and does not appear in final product) | 362.038 |
| TOTAL | 1000.000 |

EXAMPLE 7

Preparation of Capsules Containing Modified Release Fesoterodine Hydrogen Fumarate Beads Charge beads into a suitable encapsulator (e.g. Bosch GKF 400)

Charge suitable capsules into the encapsulator (e.g., gelatine size 3)

Encapsulate the beads by filling an appropriate amount of MR beads into each capsule using the bead filling station of the encapsulator and ensuring the capsules are closed properly Clean or polish the capsules as appropriate using a standard capsule polisher

EXAMPLE 8

Chemical Stability Studies for IR Beads Coated with a Solid Molecular Dispersion of Fesoterodine Hydrogen Fumarate and Hypromellose (Hydroxypropyl Methylcellulose—Methocel E5 LV (Trade Mark))

Solutions of 90:10, 85:15 and 80:20 weight % hydroxypropyl methylcellulose—Methocel E5 LV (trade mark): fesoterodine hydrogen fumarate (equivalent to 1:9, 1:5.7 and 1:4 weight % fesoterodine hydrogen fumarate:hydroxypropyl methylcellulose—Methocel E5 LV (trade mark), respectively) were prepared and coated onto microcrystalline cellulose (MCC) beads at potencies of approximately 3.0, 3.6 and 4.2% weight % (based on final IR bead) in the following manner.

Solution Preparation and Coating Process Conditions

All solutions were prepared in the same manner following a dedicated solution preparation sheet by a similar method to that of Example 1. A hydroxypropyl methylcellulose—Methocel E5 LV (trade mark) and water solution was prepared at least 4 hours in advance of coating (normally the afternoon prior to commencement of coating), with the fesoterodine hydrogen fumarate portion of the solution in water being prepared on the day of coating then mixed with the hydroxypropyl methylcellulose—Methocel E5 LV (trade mark) solution, prior to coating. The coating conditions are summarised in Table 1.

TABLE 1

Coating Conditions

| | |
|---|---|
| Equipment Parameter: | 1 kg starting batch scale |
| Fluidised bed equipment | Glatt GPCG 1.1 |
| Product container diameter (inch) | 6 |
| Spray nozzle | Schlick, 970 series, form S4 |
| Liquid insert diameter (mm) | 1.2 |
| Atomizing air annulus position | 1 mm below annulus |
| Air distribution plate type | C |
| Product filter | Woven silk filter sock |
| Silicone tubing internal diameter | 0.125 inch (3.17 mm) |
| Fixed parameters: | |
| Spray rate acceleration | Start at ~8 g/min & ramp up at 10 minute intervals |
| Target steady state spray rate (g min$^{-1}$) | ~13 g/min |
| Atomising air pressure (Bar g) | 2.0 |
| Wurster gap (mm) | 20 |
| Target product temperature (° C.) | 50 ± 3° C. |
| Target fluidization air flow (m$^3$ h$^{-1}$) | 80 ± 10% |

Stability Studies

In order to assess the chemical stability of the fesoterodine hydrogen fumarate IR beads (prepared as above at ratios of 90:10, 85:15 and 80:20 weight hydroxypropyl methylcellulose—Methocel E5 LV (trade mark):fesoterodine hydrogen fumarate) batches of each were subdivided into approximately 5 g lots, transferred to 60 cc HDPE (high density polyethylene) bottles and then stored at the accelerated storage conditions of 40° C./75% RH(RH=relative humidity).

Samples were withdrawn after 4, 8 and 12 weeks storage and analysed by HPLC (using similar conditions to those shown in Table 2 with the difference that 75 microliter injection volumes were used) with focus on the two key degradation products SPM 7675 and SPM 7605 (the chemical structures of which are shown below) and the total level of degradation products observed.

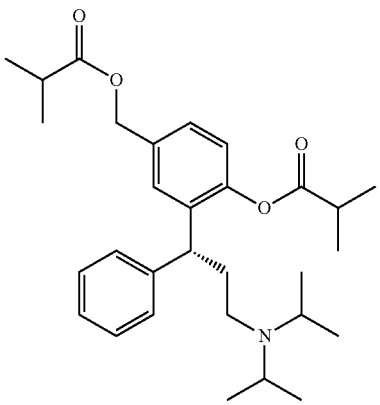

SPM 7675

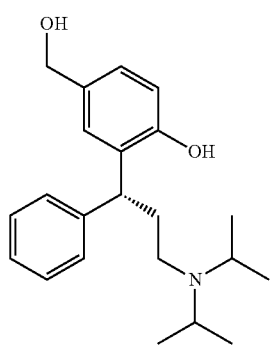

SPM 7605

Results

Figure 1C:
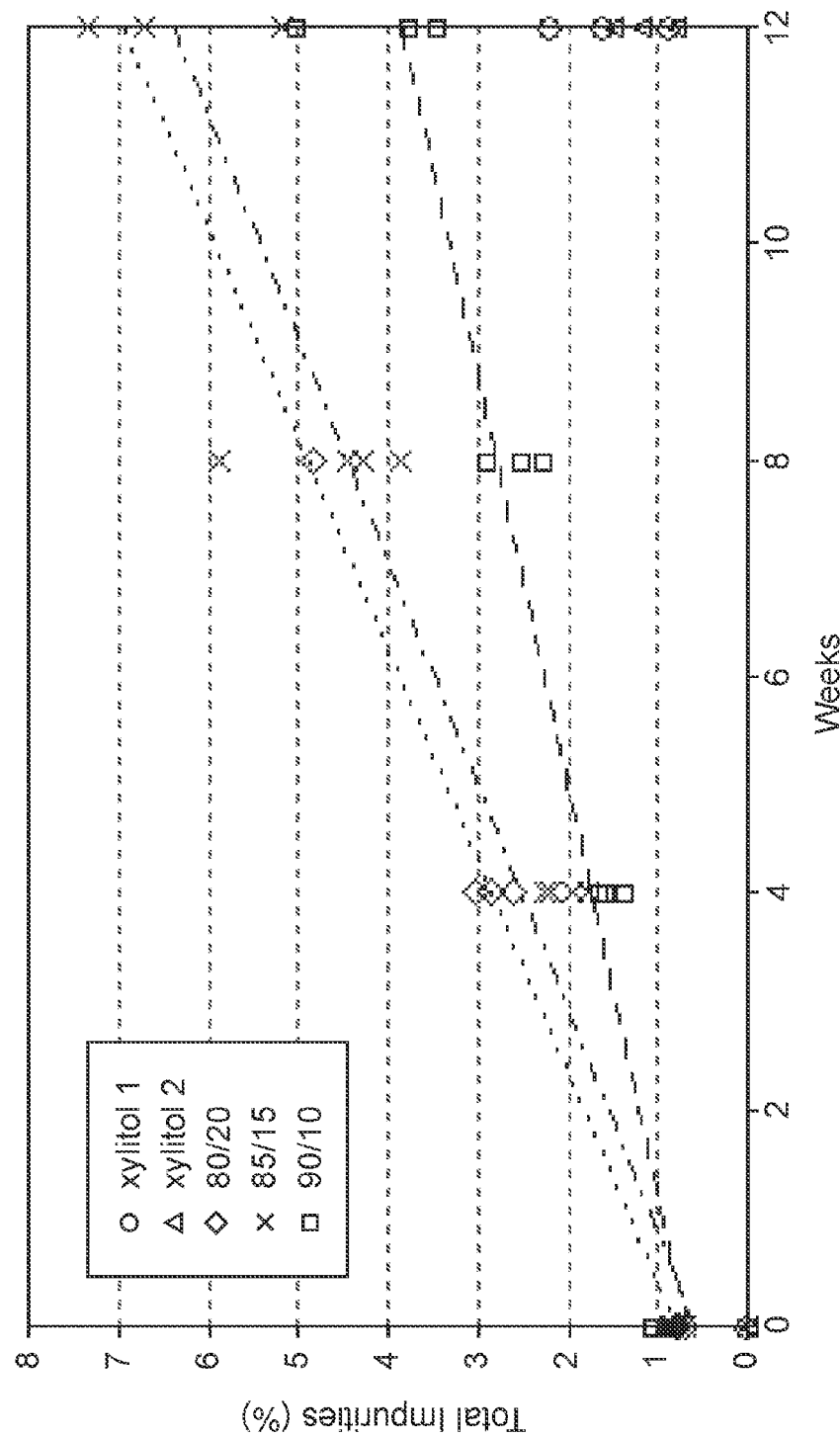
FIG. 1C depicts a summary plot showing the levels of total impurities observed on the IR beads (90:10, 85:15 and 80:20 weight % hydroxypropyl methylcellulose—Methocel E5 LV™:fesoterodine hydrogen fumarate) and the commercial tablet formulation (Xylitol 1 and 2) when stored at 40° C./75% RH.
Figure 2:
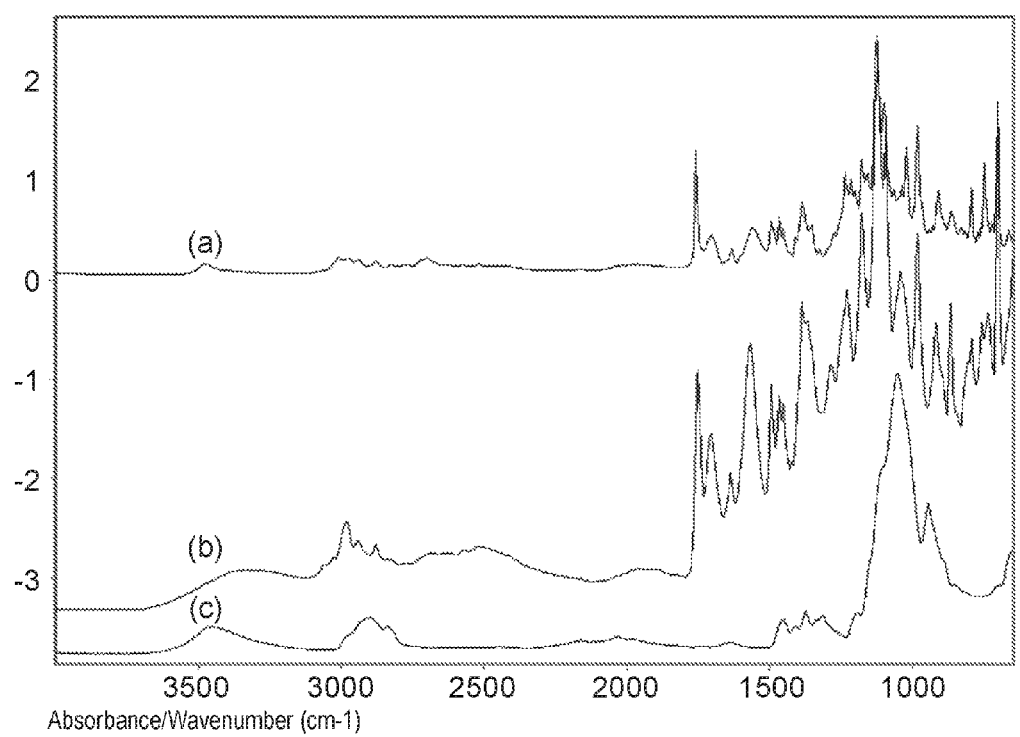
FIG. 2 depicts the FTIR ATR spectra obtained for crystalline fesoterodine hydrogen fumarate (a); amorphous fesoterodine hydrogen fumarate (b); and HPMC-hypromellose-Methocel E5LV(c).
Figure 2A:
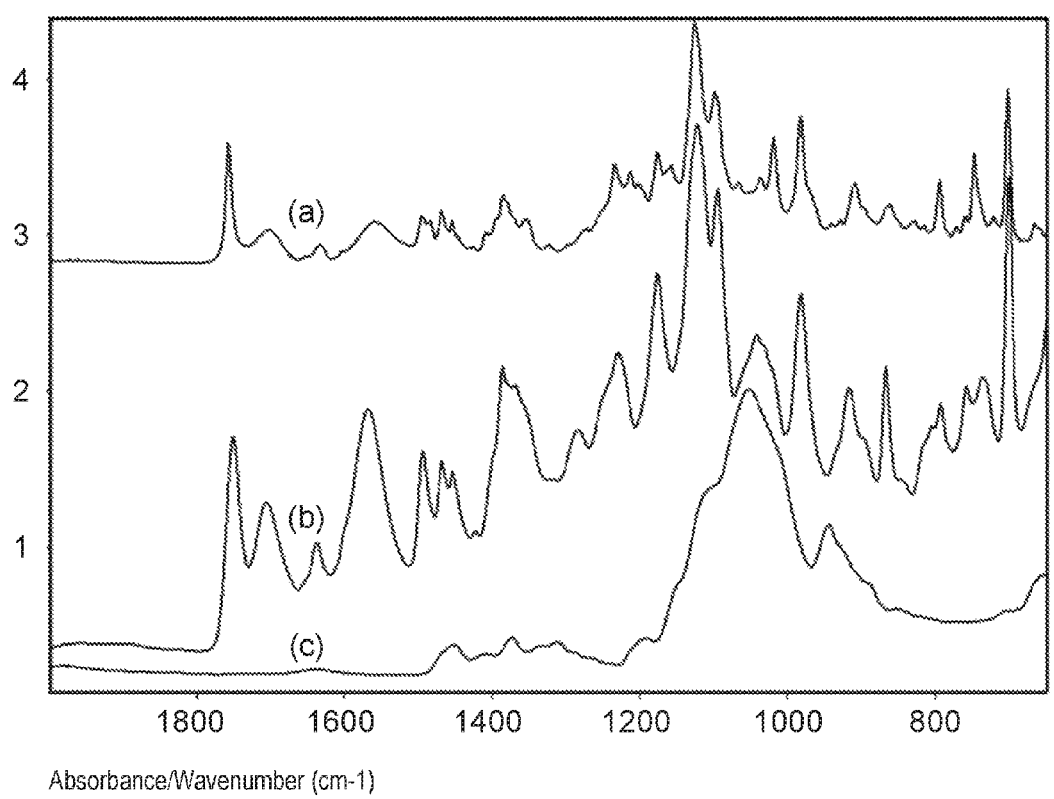
FIG. 2A depicts a fingerprint region of FIG. 2.
Figure 2B:
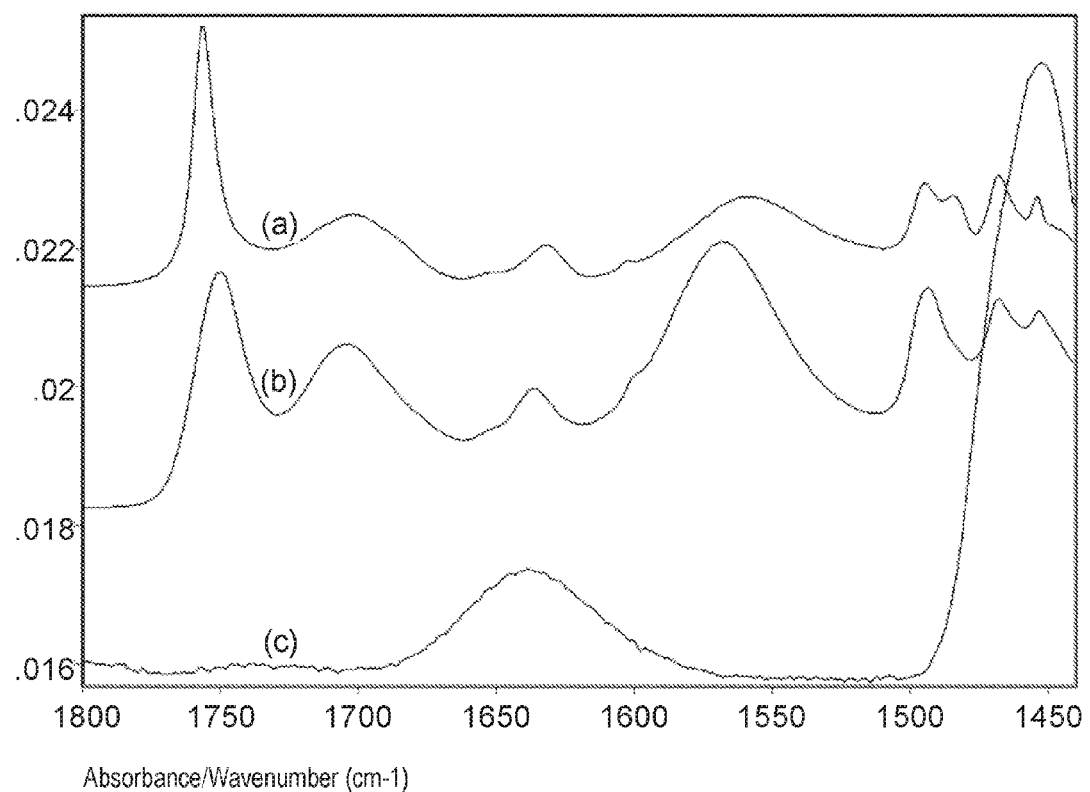
FIG. 2B depicts an area for assessment from FIGS. 2 and 2A.
Figure 3:
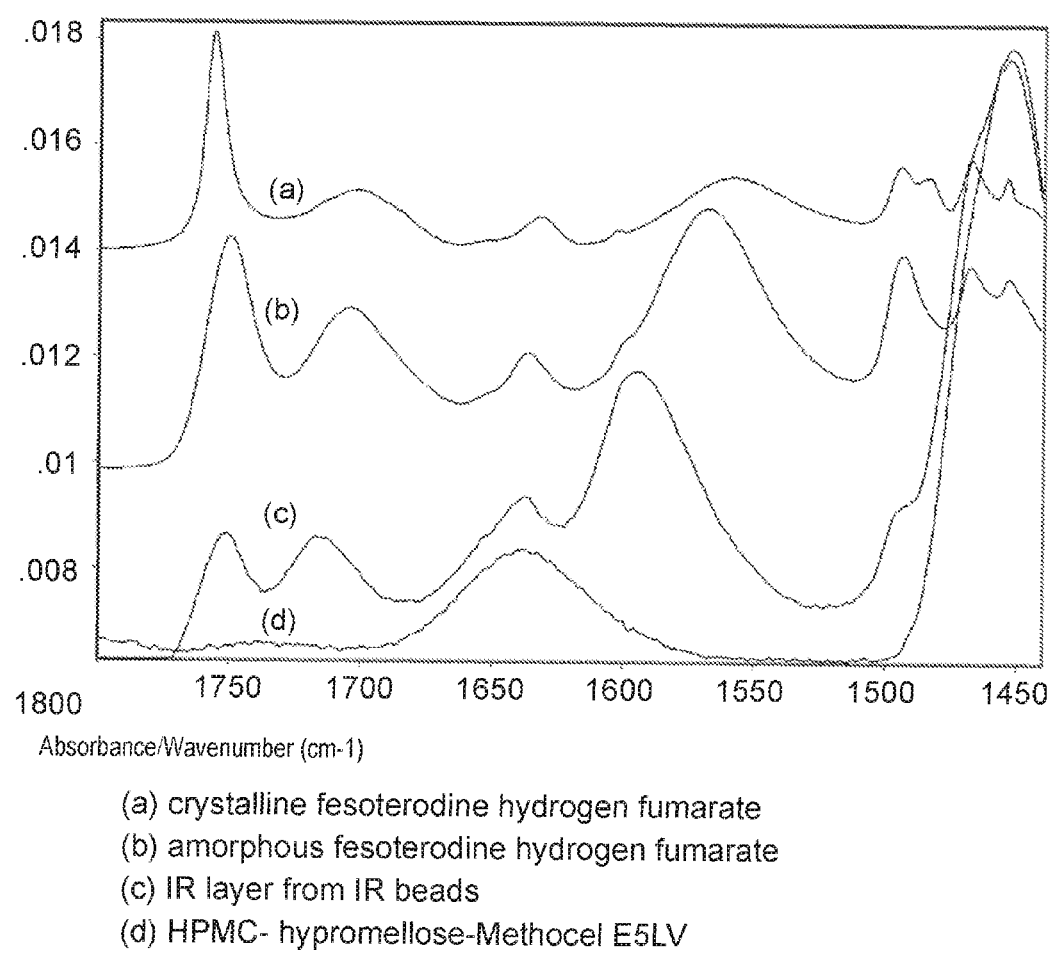
FIG. 3 depicts the FTIR ATR spectra obtained for crystalline fesoterodine hydrogen fumarate (a); amorphous fesoterodine hydrogen fumarate (b); IR layer of IR beads comprising a solid molecular dispersion of fesoterodine hydrogen fumarate and hypromellose of Examples 2 or 3 (c); and HPMC-hypromellose-Methocel E5LV(d).
Figure 3A:
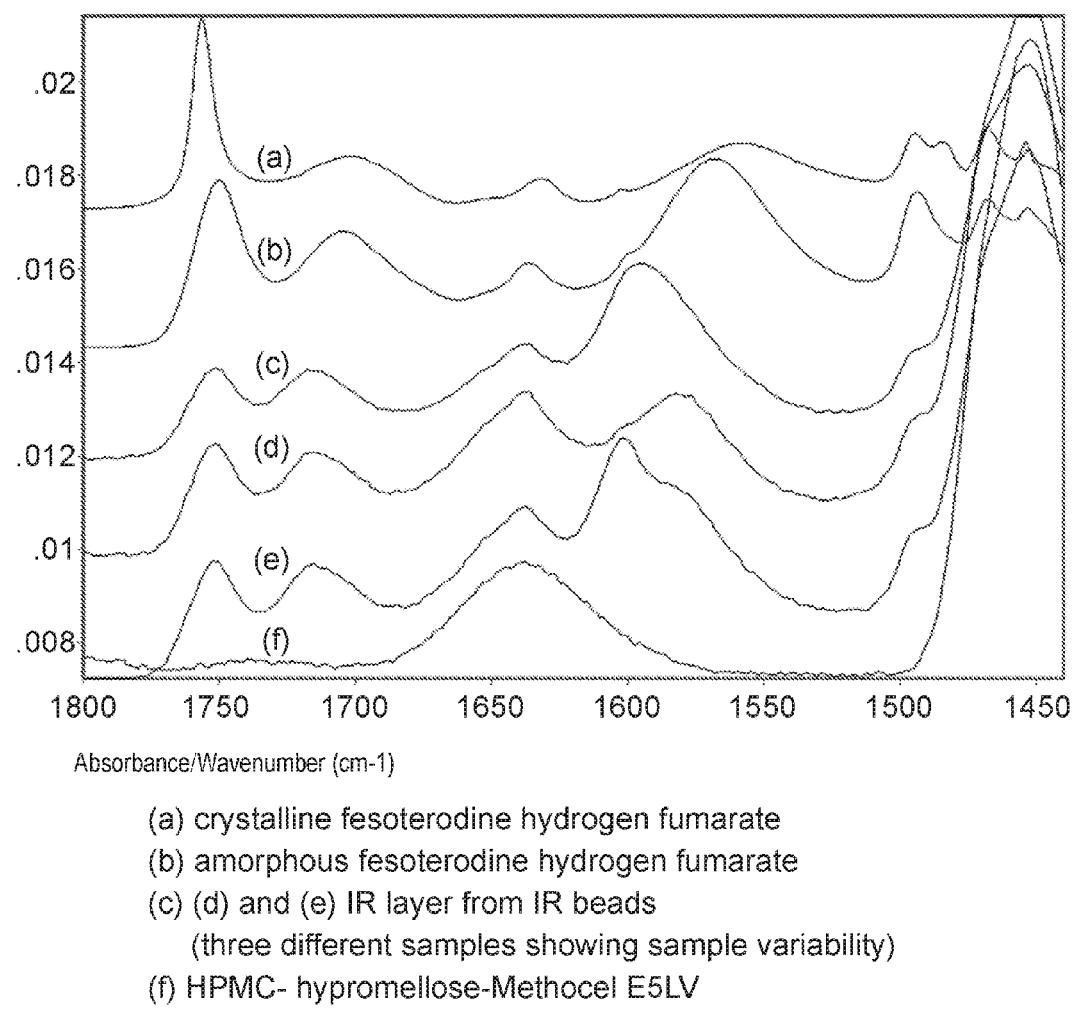
FIG. 3A depicts the FTIR ATR spectra obtained for crystalline fesoterodine hydrogen fumarate (a); amorphous fesoterodine hydrogen fumarate (b); three different samples showing sample variability of IR layer of IR beads comprising a solid molecular dispersion of fesoterodine hydrogen fumarate and hypromellose of Examples 2 or 3 (c) (d) and (e); and HPMC-hypromellose-Methocel E5LV (f).
Figure 4:
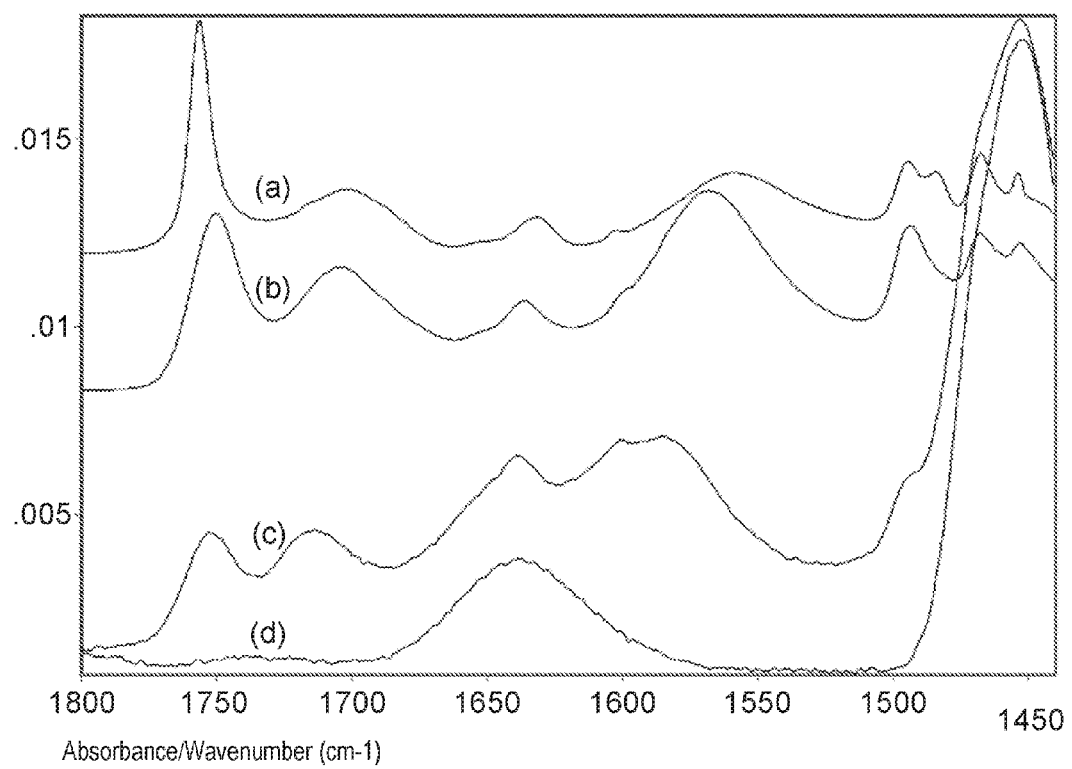
FIG. 4 depicts the FTIR ATR spectra obtained for crystalline fesoterodine hydrogen fumarate (a); amorphous fesoterodine hydrogen fumarate (b); IR layer of 10% MR beads comprising a solid molecular dispersion of fesoterodine hydrogen fumarate and hypromellose of Example 4 (c); and HPMC-hypromellose-Methocel E5LV (d).
Figure 4A:
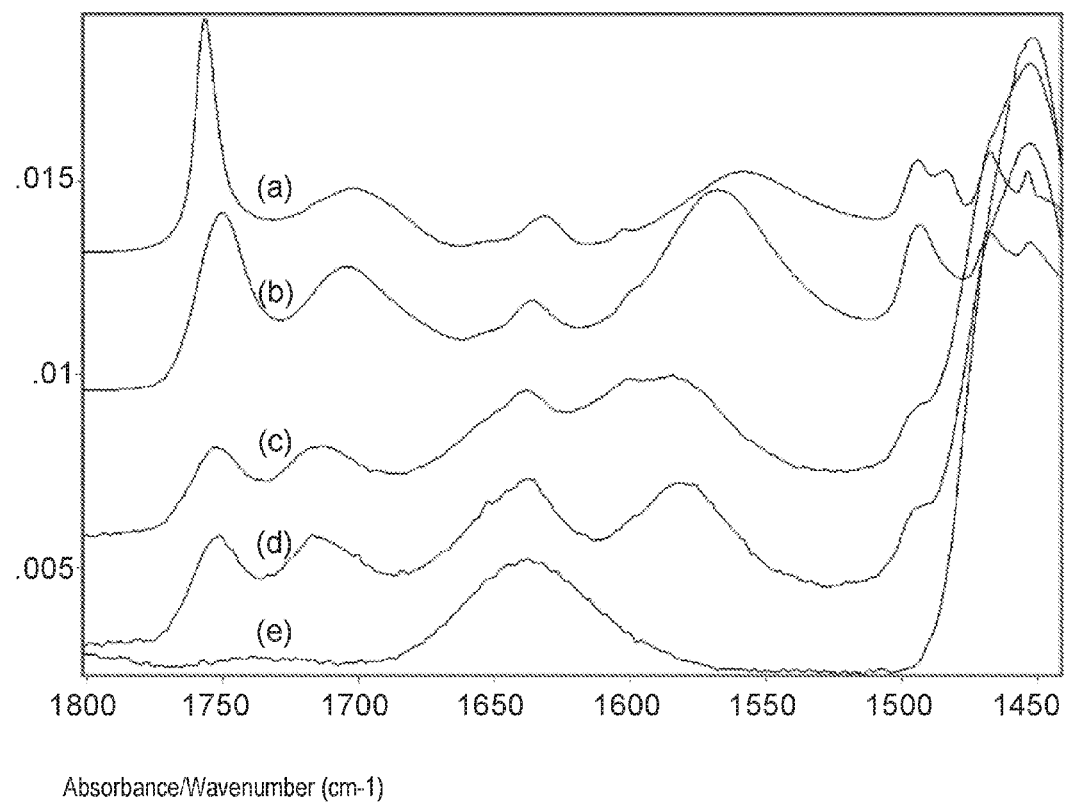
FIG. 4A depicts the FTIR ATR spectra obtained for crystalline fesoterodine hydrogen fumarate (a); amorphous fesoterodine hydrogen fumarate (b); two different samples showing sample variability of IR layer of 10% MR beads comprising a solid molecular dispersion of fesoterodine hydrogen fumarate and hypromellose of Example 4 (c) and (d); and HPMC-hypromellose-Methocel E5LV (e).
Figure 5:
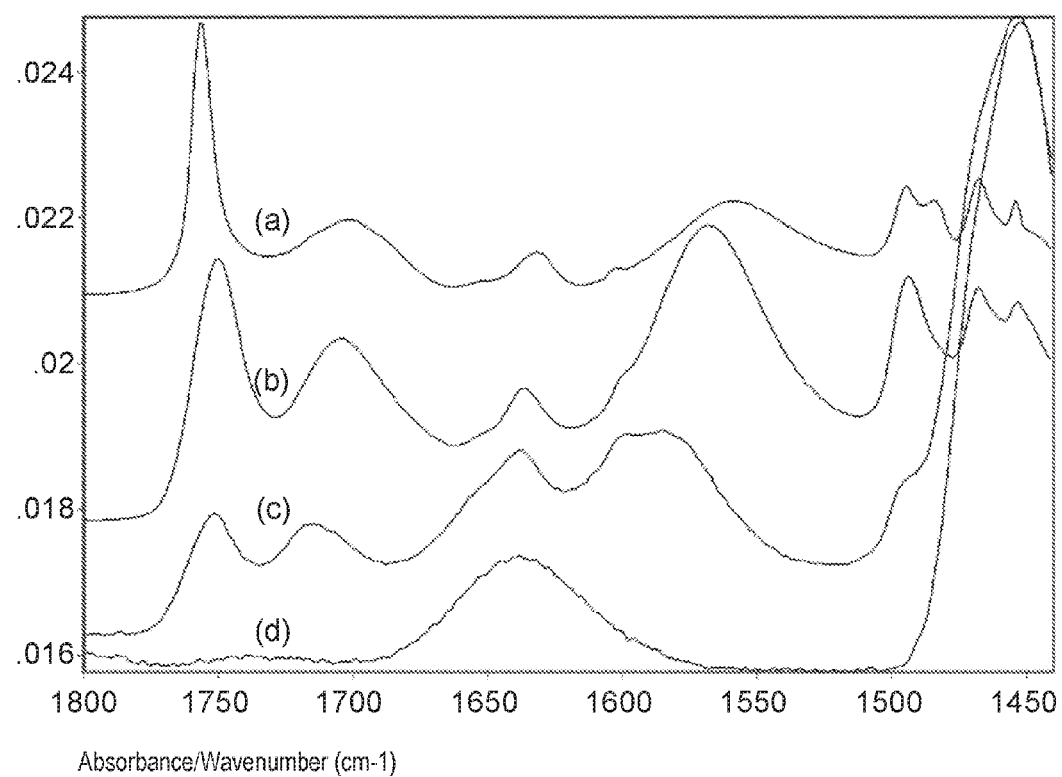
FIG. 5 depicts the FTIR ATR spectra obtained for crystalline fesoterodine hydrogen fumarate (a); amorphous fesoterodine hydrogen fumarate (b); IR layer of 20% MR beads comprising a solid molecular dispersion of fesoterodine hydrogen fumarate and hypromellose of Example 6 (c); and HPMC-hypromellose-Methocel E5LV (d).
Figure 5A:
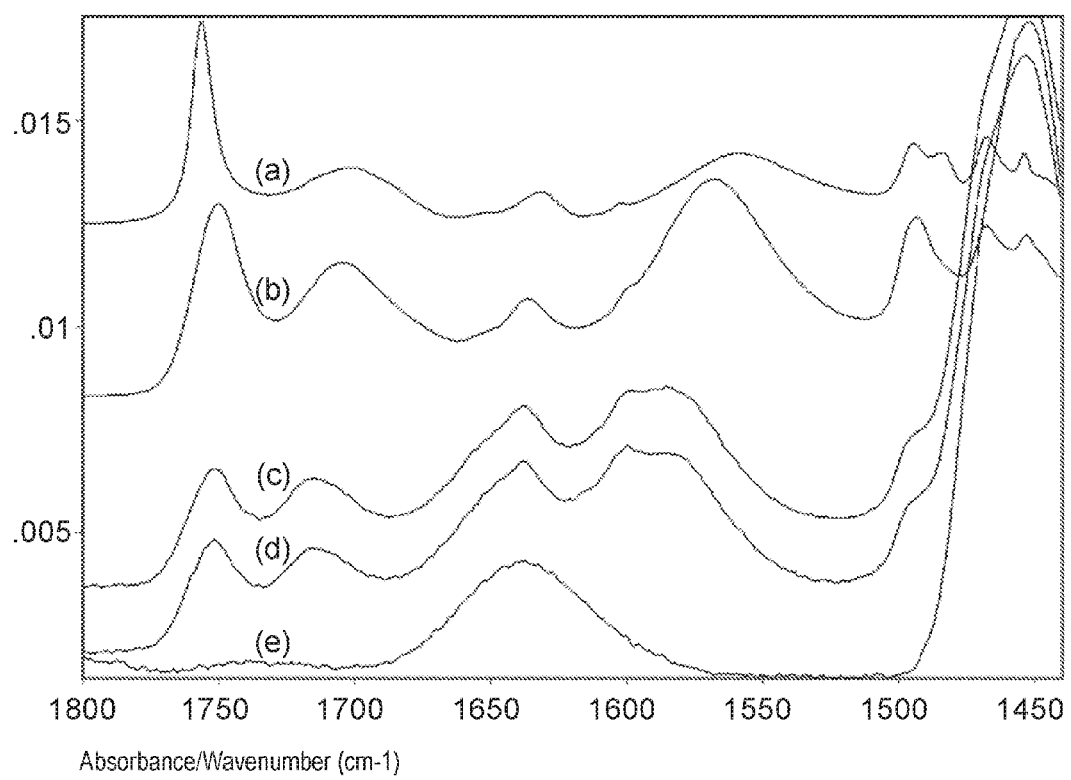
FIG. 5A depicts the FTIR ATR spectra obtained for crystalline fesoterodine hydrogen fumarate (a); amorphous fesoterodine hydrogen fumarate (b); two different samples showing sample variability of IR layer of 20% MR beads comprising a solid molecular dispersion of fesoterodine hydrogen fumarate and hypromellose of Example 4 (c) and (d); and HPMC-hypromellose-Methocel E5LV (e).
Figure 6:
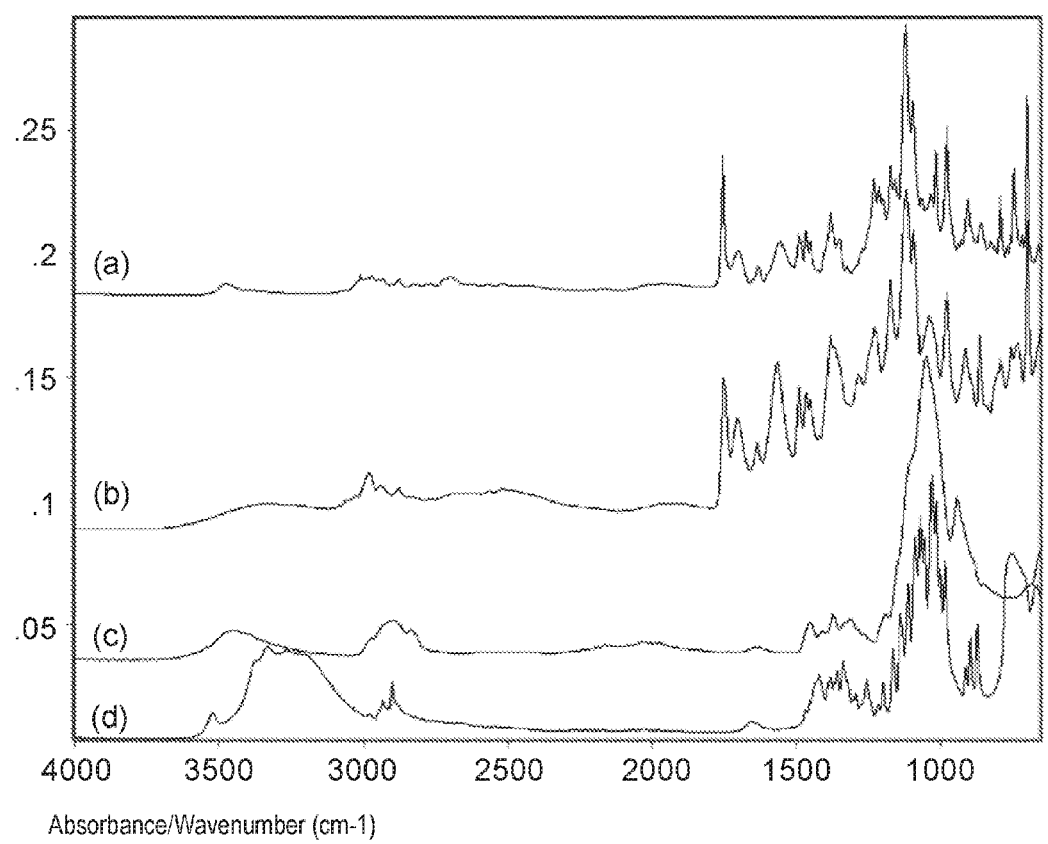
FIG. 6 depicts the FTIR ATR spectra obtained for fesoterodine hydrogen fumarate (a); amorphous fesoterodine hydrogen fumarate (b); HPMC-hypromellose-Methocel E5LV; and Lactose (Pharmatose 110 mesh).
Figure 6A:
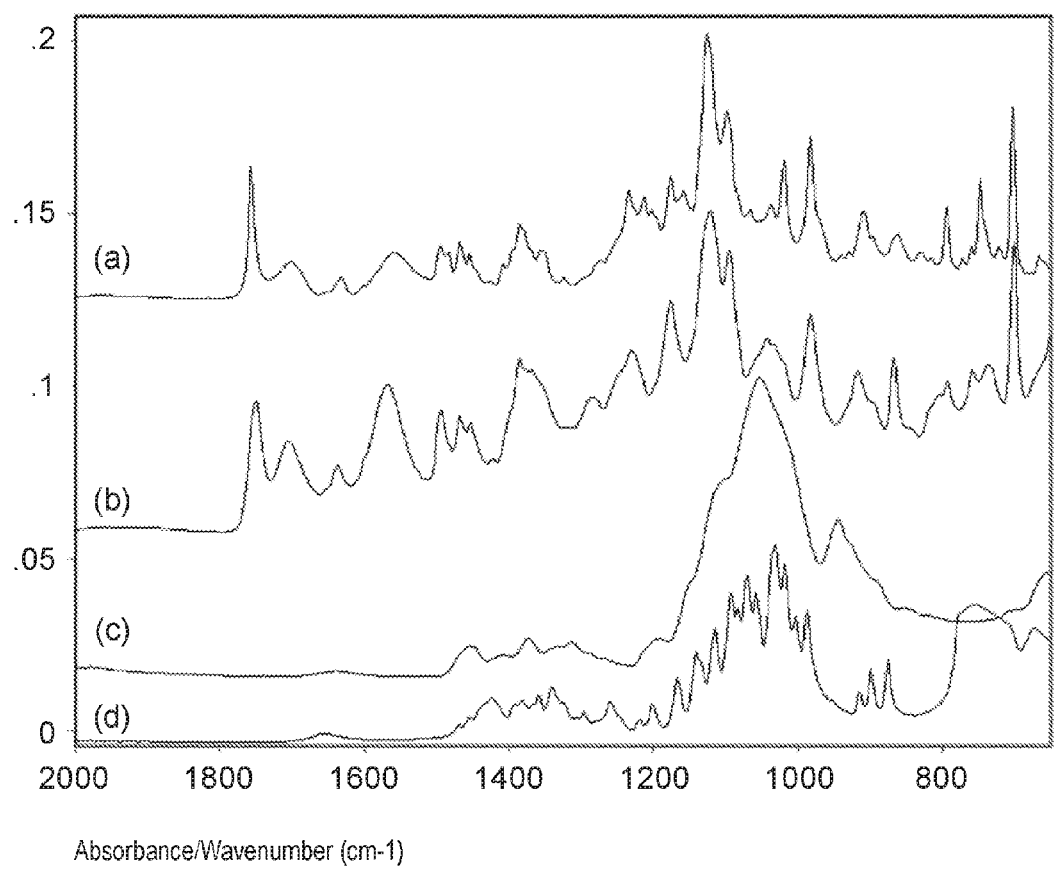
FIG. 6A depicts a fingerprint region of FIG. 6.
Figure 6B:
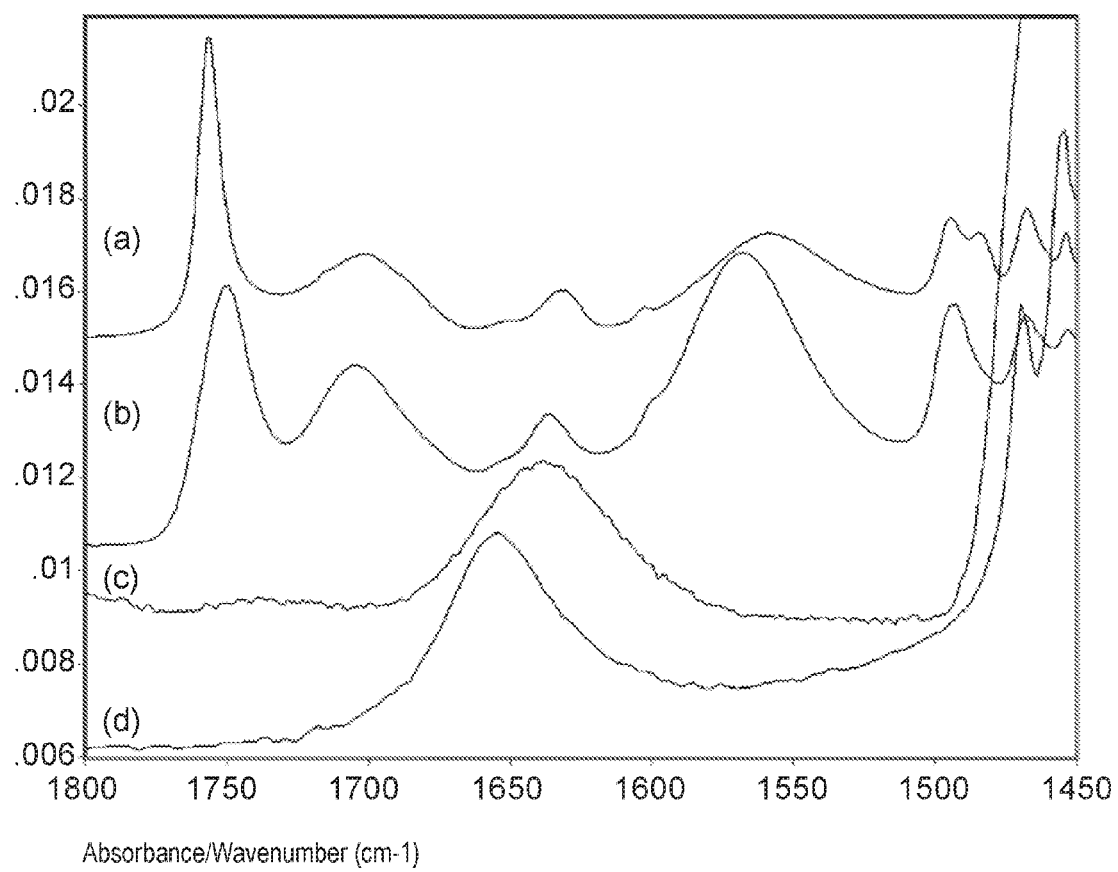
FIG. 6B depicts an area for assessment from FIGS. 6 and 6A.
Figure 7:
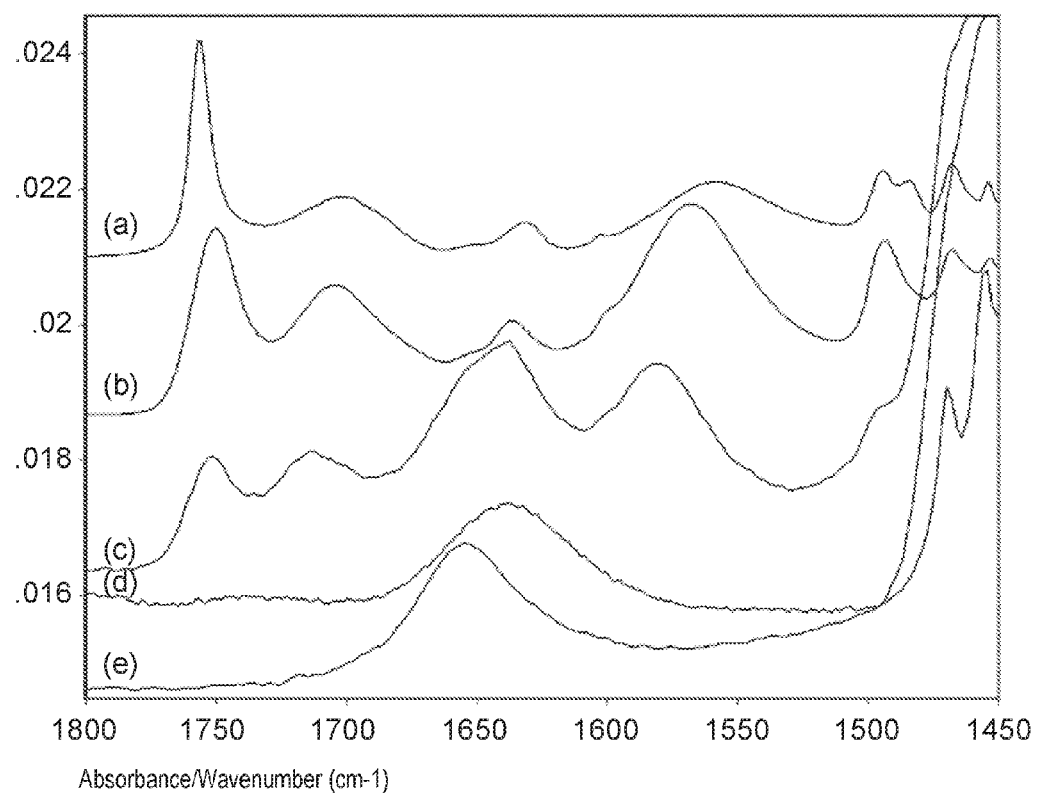
FIG. 7 depicts the FTIR ATR spectra obtained for crystalline fesoterodine hydrogen fumarate (a); amorphous fesoterodine hydrogen fumarate (b); 1:9% weight fesoterodine hydrogen fumarate/HPMC on lactose particles (c); HPMC-hypromellose-Methocel E5LV (d); and Lactose (Pharmatose 110 mesh) (e).
Figure 7A:
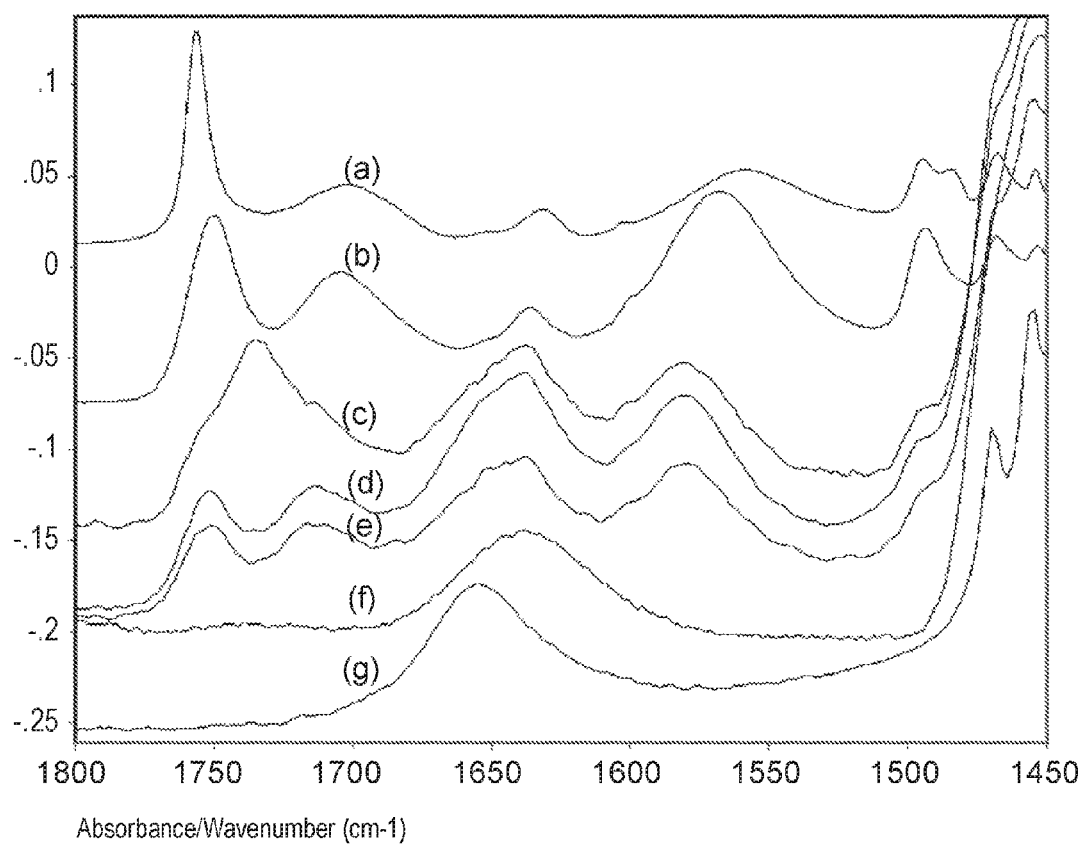
FIG. 7A depicts the FTIR ATR spectra obtained for crystalline fesoterodine hydrogen fumarate (a); amorphous fesoterodine hydrogen fumarate (b); three different samples showing sample variability of 1:9% weight fesoterodine hydrogen fumarate/HPMC on lactose particles (c) (d) and (e); HPMC-hypromellose-Methocel E5LV (f); and Lactose (Pharmatose 110 mesh) (g).
Figure 8:
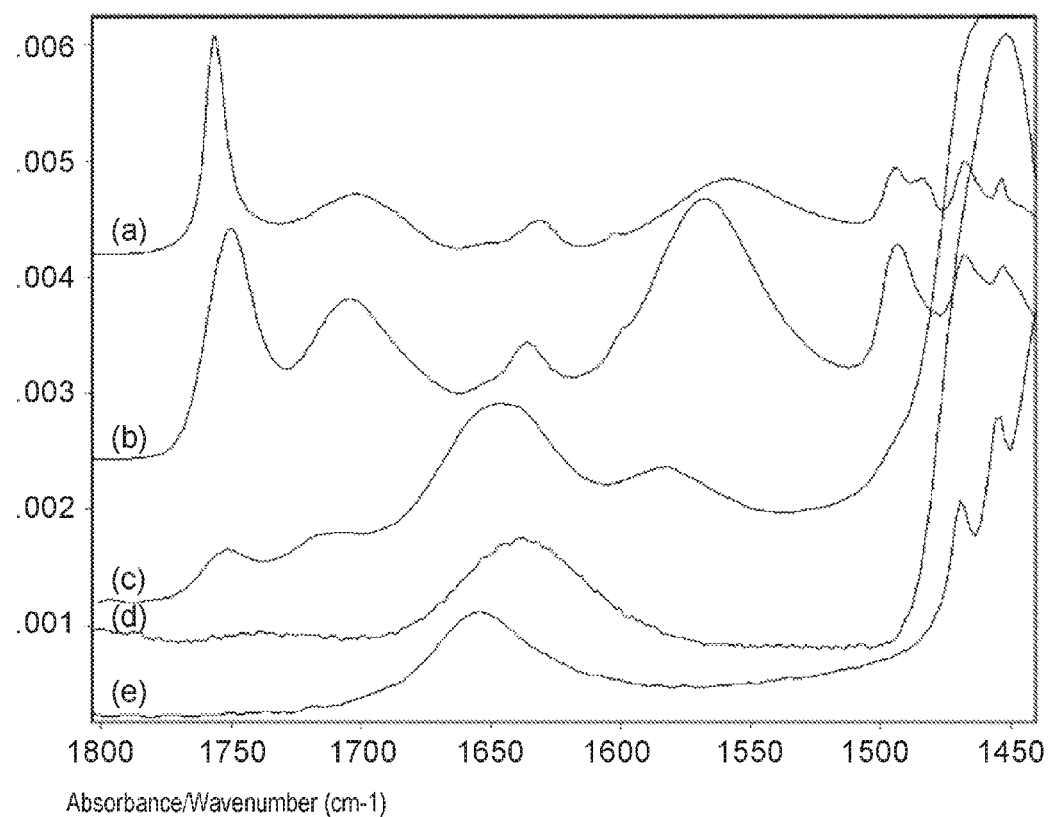
FIG. 8 depicts the FTIR ATR spectra obtained for crystalline fesoterodine hydrogen fumarate (a); amorphous fesoterodine hydrogen fumarate (b); 1:9% weight fesoterodine hydrogen fumarate/HPMC on lactose particles (c); HPMC-hypromellose-Methocel E5LV (d); and Lactose (Pharmatose 110 mesh) (e).
Figure 8A:
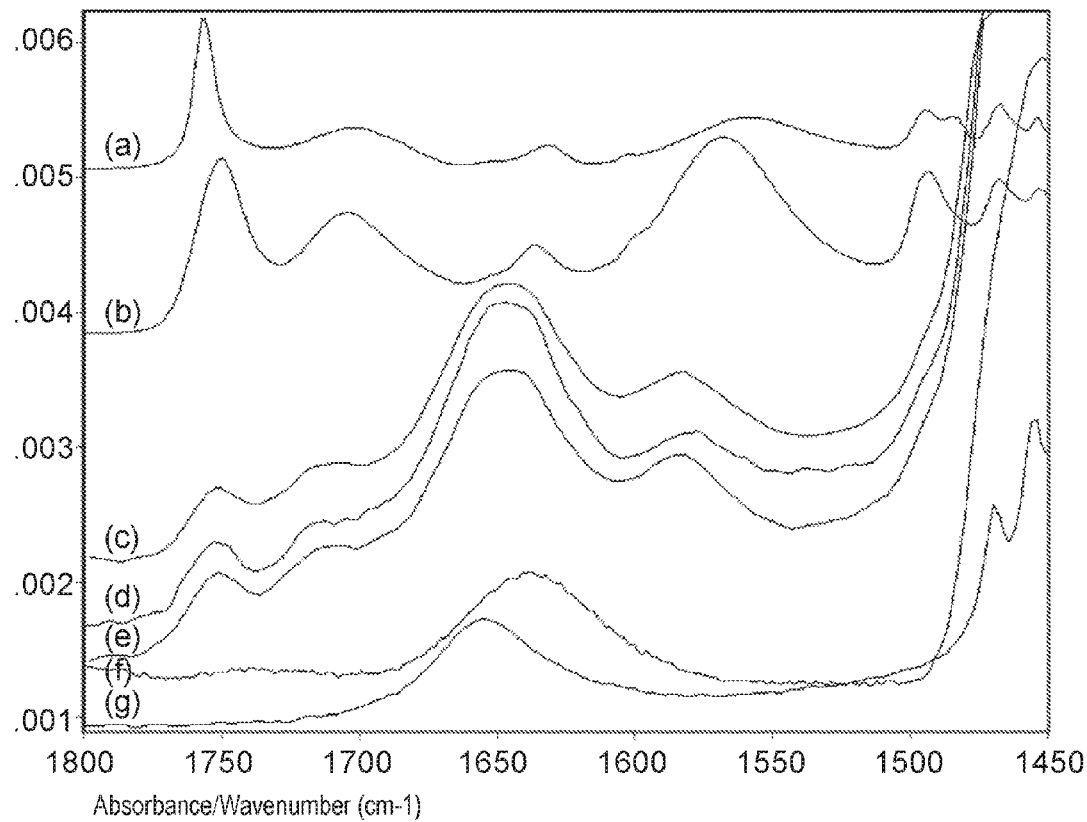
FIG. 8A depicts the FTIR ATR spectra obtained for crystalline fesoterodine hydrogen fumarate (a); amorphous fesoterodine hydrogen fumarate (b); three different samples showing sample variability of 1:9% weight fesoterodine hydrogen fumarate/HPMC on lactose particles (c) (d) and (e); HPMC-hypromellose-Methocel E5LV (f); and Lactose (Pharmatose 110 mesh) (g).

Summary plots showing the levels of SPM 7675, SPM 7605 and the total degradation products observed in the IR beads (90:10, 85:15 and 80:20 weight hydroxypropyl methylcellulose—Methocel E5 LV (trade mark):fesoterodine hydrogen fumarate) when stored at 40° C./75% RH are shown in FIGS. 1(a)-(c).

For comparative purposes, FIGS. 1(a)-(c) also include data on the levels of SPM 7675, SPM 7605 and total degradation products present in the fesoterodine hydrogen fumarate commercial xylitol-based tablet formulation (Xylitol 1* and Xylitol 2**) stored under similar accelerated stability conditions.

In summary, it can be seen that the fesoterodine hydrogen fumarate IR beads prepared with a ratio of 90:10 weight % hydroxypropyl methylcellulose—Methocel E5 LV (trade mark):fesoterodine hydrogen fumarate have a comparable chemical stability to the commercial xylitol tablet formulation.

(*Xylitol 1—sample of 4 mg fesoterodine commercial tablets (see WO2007/141298A1 on page 44, Table 1, Example C) packaged in blisters in accordance with European Union regulatory requirements. The packaging material is a laminated aluminium foil, mouldable for bottoms of push-through packages. The composite film consists of the following materials:

Oriented polyamide (oPA), thickness of about 25 μm

Aluminium, thickness of about 45 μm

PVC, thickness of about 60 μm)

(**Xylitol 2—sample of 4 mg fesoterodine commercial tablets (see WO2007/141298A1 on page 44, Table 1, Example C) from a package containing 90 tablets per bottle each with a desiccant canister filled with 3 g of silica gel.)

EXAMPLE 9

Chemical Stability and Dissolution Studies for IR Beads Coated with a Solid Molecular Dispersion of 1:9 Weight % Fesoterodine Hydrogen Fumarate:Hypromellose (Hydroxypropyl Methylcellulose—Methocel E5 LV—Trade Mark) and for Sustained Release (SR, i.e. MR) Coated Bead Formulations Thereof Process Description—Immediate Release (IR) Beads These were prepared by a similar process to that described in Example 2.

Process Description—10% and 20% Sustained Release (SR) Beads

These were prepared by a similar process to that described in Example 4 and 6, respectively, using a Glatt GPCG 1.1 fluid bed coater.

Stability Studies for Fesoterodine Hydrogen Fumarate Immediate Release (IR) and Sustained Release (SR) Beads Stability studies were conducted on both fesoterodine hydrogen fumarate IR beads and fesoterodine hydrogen fumarate SR beads (10% and 20% w/w of final bead).

Fesoterodine hydrogen fumarate IR and SR beads (10% and 20% SR coat) were packaged in sealed double polyethylene bags with desiccant in between liners inside a fibreboard drum and stored at 5° C., 25° C./60% relative humidity (RH) and 30° C./75% RH.

Visual appearance, chemical stability (degradation products by HPLC) and dissolution were tested initially, after 3 and 6 months storage at 5° C., and after 6 weeks and 3 months storage at 25° C./60% RH and 30° C./75% RH.

Analytical Methods (a) Degradation Products by HPLC

The method for the determination of the degradation products of fesoterodine hydrogen fumarate IR and SR beads was a reversed-phase HPLC method with conditions as described in Table 2. Identification was accomplished by comparing retention times of the impurity markers and samples. Quantification of specified and unspecified degradation products was achieved by the comparison of peak area response in a test sample with that of an external standard solution. Total degradation products is the sum of all specified and unspecified degradation products by HPLC, excluding Process Related Impurities, present above the reporting threshold of 0.05%.

TABLE 2

Chromatographic Conditions

| | | |
|---|---|---|
| Mobile phase A (MPA) | 0.1% trifluoroacetic acid (aq) | |
| Mobile phase B (MPB) | 0.1% trifluoroacetic acid (far UV Acetonitrile) | |
| Detector | UV absorbance at 220 nm | |
| Injection volumes | REF MIX 75 µL | |
| | LOQ 20 µL | |
| | TEST 20 µL | |
| Column temperature | 35° C. | |
| Auto sampler temperature | 5° C. | |
| Flow Rate | 1.2 mL/min | |
| Run Time | 23 minutes | |

TABLE 2-continued

Chromatographic Conditions

| Elution Mode | Gradient | | | | | | |
|---|---|---|---|---|---|---|---|
| | Time (min) | 0.0 | 10.0 | 10.1 | 19.0 | 19.1 | 23.0 |
| | MPA (%) | 75 | 75 | 50 | 50 | 75 | 75 |
| | MPB (%) | 25 | 25 | 50 | 50 | 25 | 25 |
| Column | Spheribond CN 5 µm or Waters Spherisorb | | | | | | |
| Stationary Phase | CN 5 µm or equivalent | | | | | | |

(b) Dissolution

The rate of dissolution of fesoterodine hydrogen fumarate IR and SR beads is determined using a rotating paddle procedure (USP Apparatus 2) in 900 mL of USP phosphate buffer dissolution medium. The amount of fesoterodine hydrogen fumarate dissolved in the dissolution medium is determined by a reversed-phase HPLC method with conditions as described in Table 3.

TABLE 3

Chromatographic Conditions

| | |
|---|---|
| Mobile phase A (MPA) | Potassium phosphate buffer @ pH ~6.5 + 5% far UV acetonitrile |
| Mobile phase B (MPB) | Far UV acetonitrile |
| Detector | UV absorbance at 220 nm |
| Injection volume | 75 µL |
| Column temperature | 30° C. |
| Flow Rate | 2.0 mL/min |
| Run Time | 2 minutes |
| Elution Mode | Isocratic |
| | MPA (%) 75 |
| | MPB (%) 25 |
| Column Stationary Phase | Water XBridge C18 5 µm or equivalent |

Results

Stability data for fesoterodine hydrogen fumarate IR beads are presented in Tables 4 to 6, for fesoterodine fumarate SR beads (10% SR coat) in Tables 7 to 9, and for fesoterodine fumarate SR beads (20% SR coat) in Tables 10 to 12.

The immediate release (IR) beads coated with a solid molecular dispersion of 1:9 weight % fesoterodine hydrogen fumarate:hypromellose (hydroxypropyl methyl cellulose—Methocel E5 LV—trade mark) showed no significant increase in the levels of degradation products after 6 months storage at 5° C. and only small and acceptable increases after 3 months storage at 25° C./60% RH and 30° C./75% RH.

Similarly, the sustained release (SR) beads (at both 10 and 20% SR coating levels) showed no significant increase in the levels of degradation products after 6 months storage at 5° C. and only small and acceptable increases after 3 months storage at 25° C./60% RH and 30° C./75% RH.

Dissolution profiles of both the IR and SR beads were satisfactory at all storage conditions.

TABLE 4

Stability of fesoterodine hydrogen fumarate IR Beads stored at 5° C.

| Test | Acceptance Criteria | Initial | Time Point 3 months Results | 6 months |
|---|---|---|---|---|
| Appearance | Off white free flowing beads. No evidence of visible foreign matter or contamination. | Meets Test | Meets Test | Meets Test |
| | Degradation Products | | | |
| | SPM 7605 | 0.10% | 0.13% | 0.16% |
| | SPM 7675 | 0.19% | 0.15% | 0.16% |
| | Total | 1.4%$^a$ | 0.69% | 0.69% |
| Dissolution | Report Result Time Point (minutes) | | | |
| | 15 | NT | 107 | 106 |
| | 30 | 80 | 111 | 109 |
| | 45 | NT | 111 | 112 |
| | 60 | 82 | 111 | 111 |

TABLE 5

Stability of fesoterodine hydrogen fumarate IR Beads stored at 25° C./60% RH

| Test | Acceptance Criteria | Initial | Time Point 6 weeks Results | 3 months |
|---|---|---|---|---|
| Appearance | Off white free flowing beads. No evidence of visible foreign matter or contamination. | Meets Test | Meets Test | Meets Test |
| | Degradation Products | | | |
| | SPM 7605 | 0.10% | 0.24% | 0.32% |
| | SPM 7675 | 0.19% | 0.08% | 0.21% |
| | Total | 1.4%$^a$ | 0.71% | 0.90% |
| Dissolution | Report Result Time Point (minutes) | | | |
| | 15 | NT | 105 | 91 |
| | 30 | 80 | 106 | 94 |
| | 45 | NT | 108 | 98 |
| | 60 | 82 | 108 | 99 |

TABLE 6

Stability of fesoterodine hydrogen fumarate IR Beads stored at 30° C./75% RH

| Test | Acceptance Criteria | Initial | Time Point 6 weeks Results | 3 months |
|---|---|---|---|---|
| Appearance | Off white free flowing beads. No evidence of visible foreign matter or contamination. | Meets Test | Meets Test | Meets Test |
| | Degradation Products | | | |
| | SPM 7605 | 0.10% | 0.48% | 0.89% |
| | SPM 7675 | 0.19% | 0.12% | 0.29% |
| | Total | 1.4%$^a$ | 1.1% | 1.6% |
| Dissolution | Report Result Time Point (minutes) | | | |
| | 15 | NT | 103 | 98 |
| | 30 | 80 | 106 | 101 |
| | 45 | NT | 109 | 101 |
| | 60 | 82 | 109 | 102 |

TABLE 7

Stability of fesoterodine hydrogen fumarate SR Beads (10% SR Coat) stored at 5° C.

| Test | Acceptance Criteria | Time Point | | |
|---|---|---|---|---|
| | | Initial | 3 months Results | 6 months |
| Appearance | Off white free flowing beads. No evidence of visible foreign matter or contamination. | Meets Test | Meets Test | Meets Test |
| | Degradation Products | | | |
| | SPM 7605 | 0.11% | 0.13% | 0.16% |
| | SPM 7675 | 0.21% | 0.14% | 0.16% |
| | Total | 1.2%$^a$ | 0.60% | 0.69% |
| Dissolution | Report Result Time Point (hours) | | | |
| | 1 | 14 | 15 | 13 |
| | 2 | 39 | 40 | 37 |
| | 4 | 84 | 82 | 77 |
| | 16 | 108 | 105 | 102 |

TABLE 8

Stability of fesoterodine hydrogen fumarate SR Beads (10% SR Coat) stored at 25° C./60% RH

| Test | Acceptance Criteria | Time Point | | |
|---|---|---|---|---|
| | | Initial | 6 weeks Results | 3 months |
| Appearance | Off white free flowing beads. No evidence of visible foreign matter or contamination. | Meets Test | Meets Test | Meets test |
| | Degradation Products | | | |
| | SPM 7605 | 0.11% | 0.25% | 0.34% |
| | SPM 7675 | 0.21% | 0.12% | 0.21% |
| | Total | 1.2%$^a$ | 0.56% | 0.93% |
| Dissolution | Report Result Time Point (hours) | | | |
| | 1 | 14 | 16 | 11 |
| | 2 | 39 | 42 | 35 |
| | 4 | 84 | 84 | 79 |
| | 16 | 108 | NT | 107 |

TABLE 9

Stability of fesoterodine hydrogen fumarate SR Beads (10% SR Coat) stored at 30° C./75% RH

| Test | Acceptance Criteria | Time Point | | |
|---|---|---|---|---|
| | | Initial | 6 weeks Results | 3 months |
| Appearance | Off white free flowing beads. No evidence of visible foreign matter or contamination. | Meets Test | Meets Test | Meets Test |
| | Degradation Products | | | |
| | SPM 7605 | 0.11% | 0.50% | 0.96% |
| | SPM 7675 | 0.21% | 0.16% | 0.30% |
| | Total | 1.2%$^a$ | 0.90% | 1.7% |
| Dissolution | Report Result Time Point (hours) | | | |
| | 1 | 14 | 15 | 14 |
| | 2 | 39 | 35 | 35 |
| | 4 | 84 | 75 | 70 |
| | 16 | 108 | NT | 92 |

TABLE 10

Stability of fesoterodine hydrogen fumarate SR Beads (20% SR Coat) stored at 5° C.

| | | | Time Point | |
|---|---|---|---|---|
| Test | Acceptance Criteria | Initial | 3 months Results | 6 months |
| Appearance | Off white free flowing beads. No evidence of visible foreign matter or contamination. | Meets Test | Meets Test | Meets Test |
| | Degradation Products | | | |
| | SPM 7605 | 0.11% | 0.14% | 0.19% |
| | SPM 7675 | 0.23% | 0.15% | 0.16% |
| | Total | 1.1% | 0.64% | 0.72% |
| Dissolution | Report Result Time Point (hours) | | | |
| | 1 | 0 | 3 | 4 |
| | 2 | 0 | 9 | 11 |
| | 4 | 28 | 28 | 31 |
| | 16 | 93 | 83 | 93 |
| | | 20 | | |

TABLE 11

Stability of fesoterodine hydrogen fumarate SR Beads (20% SR Coat) stored at 25° C./60% RH

| | | | Time Point | |
|---|---|---|---|---|
| Test | Acceptance Criteria | Initial | 6 weeks Results | 3 months |
| Appearance | Off white free flowing beads. No evidence of visible foreign matter or contamination. | Meets Test | Meets Test | Meets Test |
| | Degradation Products | | | |
| | SPM 7605 | 0.11% | 0.29% | 0.35% |
| | SPM 7675 | 0.23% | 0.12% | 0.21% |
| | Total | 1.1% | 0.89% | 0.95% |
| Dissolution | Report Result Time Point (hours) | | | |
| | 1 | 0 | 7 | 2 |
| | 2 | 0 | 13 | 9 |
| | 4 | 28 | 32 | 28 |
| | 16 | 93 | NT | 106 |

TABLE 12

Stability of fesoterodine hydrogen fumarate SR Beads (20% SR Coat) stored at 30° C./75% RH

| | | | Time Point | |
|---|---|---|---|---|
| Test | Acceptance Criteria | Initial | 6 weeks Results | 3 months |
| Appearance | Off white free flowing beads. No evidence of visible foreign matter or contamination. | Meets Test | Meets Test | Meets Test |
| | Degradation Products | | | |
| | SPM 7605 | 0.11% | 0.50% | 0.94% |
| | SPM 7675 | 0.23% | 0.16% | 0.30% |
| | Total | 1.1% | 0.93% | 1.7% |
| Dissolution | Report Result Time Point (hours) | | | |
| | 1 | 0 | 7 | 3 |
| | 2 | 0 | NT | 9 |
| | 4 | 28 | 29 | 26 |
| | 16 | 93 | NT | 95 |

NT = Not tested a) Isopropyl alcohol (IPA) used in the sample dilution solvent was found to enhance the level of an unspecified impurity. IPA was replaced by methanol as the dilution solvent from the 3 M time point

EXAMPLE 10

Preparation of Tablets Containing a Solid Molecular Dispersion of 1:19 or 1:9 weight % Fesoterodine Hydrogen Fumarate:HPMC (Hypromellose) on Lactose Particles Using a Glatt GPCG 1.1 Coater a) Preparation of a Solution of Fesoterodine Hydrogen Fumarate and HPMC (Hypromellose)

| Component* | 1:9 Formulation Quantity per tablet (mg) | 1:19 Formulation Quantity per tablet (mg) |
|---|---|---|
| Fesoterodine hydrogen fumarate | 8.0 | 8.0 |
| Lactose (Pharmatose 110M) | 65.853 | 65.853 |
| Hypromellose (Methocel E5) | 72.0 | 152.0 |
| Isopropanol | 1.064 | 2.128 |
| Water | 0.456 | 0.912 |

(*quantities based on dry finished product with no overage. Can incorporate 10% overage of the quantities of the coating materials to allow for in-process loss due to tubing volumes, coating of containers, etc.)

Calculate amounts of materials to use based on a 300 g starting charge of lactose in the coater.
Set-up an overhead stirrer and impeller.
Weigh out 50% of water into an appropriate sized vessel.
Dissolve fesoterodine hydrogen fumarate in water
Mix remainder of water with isopropanol (IPA)
Set the agitator speed to produce a suitable vortex and gradually add the HPMC to the IPA/water and mix for a suitable time ensuring that the solution does not foam. Cover to prevent evaporation while stirring (ensure there are no lumps after stirring).
Add the remaining water/API solution to the HPMC solution with agitation b) Preparation of a Solid Molecular Dispersion of Fesoterodine Hydrogen Fumarate and Hypromellose on Lactose Powder Using Glatt GPCG 1.1 Coater Heat Glatt GPCG 1.1 in 6" Wurster configuration to a product temp of ~30° C.
Charge the lactose powder (300 g) into the coater
Once the powder is fully fluidised commence spraying within 1 minute.
The product temperature during coating (at/near maximum spray rate in steady state) should be approximately 30° C.
Continue spraying until all the theoretical quantity of coating solution has been sprayed onto the powder.
Cover the solution to prevent evaporation while coating.
After coating, dry the granules by allowing the product temperature to rise by 2° C. before shutting down the fluidisation air & heat.

c) Preparation of Tablets Containing the Granules from Step (b)

| Component* | 1:9 Formulation Quantity per tablet (mg) | 1:19 Formulation Quantity per tablet (mg) |
|---|---|---|
| Fesoterodine Granules | 145.853 | 225.853 |
| Hypromellose (Methocel K100M) | 78.137 | 120.995 |
| Glyceryl Behenate (Compritol 888 ATO) | 6.512 | 10.084 |
| Talc | 5.535 | 8.571 |
| Total | 236.0 | 365.5 |

Blend fesoterodine granules and hypromellose in a suitable blender.
Add Compritol and talc to the blender and blend.
Compress tablets using a suitable tablet press and appropriately sized tooling.

EXAMPLE 11

Determination of the Comparative Chemical Stability of Samples of Fesoterodine Hydrogen Fumarate with HPMC and Other Polymeric Binders on Lactose Particles a) Sample Preparation The 1:19 and 1:9 HPMC samples were prepared as described in Example 10, steps (a) and (b).

The non-HPMC samples were prepared by a similar method to that described in Example 10, steps (a) and (b), using the specified non-HPMC polymeric binder. All non-HPMC samples contained 1:9 weight % of fesoterodine hydrogen fumarate:polymeric binder.

b) Stability Data

The analytical methodology employed for the determination of the degradation products SPM-7605 and SPM 7675 (see chemical structures in Example 8) in samples of fesoterodine hydrogen fumarate and HPMC/other polymeric binder on lactose was similar to that described in Example 9 with minor modifications to the HPLC conditions as described in Table 13.

TABLE 13

| | | | | | |
|---|---|---|---|---|---|
| Mobile phase A (MPA) | 0.1% trifluoroacetic acid (aqueous) | | | | |
| Mobile phase B (MPB) | 0.1% trifluoroacetic acid (far UV acetonitrile) | | | | |
| Detector | UV absorbance at 220 nm | | | | |
| Injection volumes | Test | 75 µL | | | |
| Flow Rate | 1.2 mL/min | | | | |
| Run Time | 45 minutes | | | | |
| Elution Mode | Gradient | | | | |
| | Time (min) | 0.0 | 35.0 | 35.1 | 45.0 |
| | MPA (%) | 72 | 72 | 50 | 50 |
| | MPB (%) | 28 | 28 | 50 | 50 |
| Column Stationary Phase | Waters Spherisorb CN 5 µm or equivalent | | | | |

12 week chemical stability data were generated on the samples after storage at 40 C/75% RH under closed conditions using induction sealed HDPE bottles and using a 1 g desiccant cartridge. The results obtained are summarised in Table 14.

TABLE 14

| Polymeric binder used in sample[1,2] (on lactose particles) | SPM 7605 % | SPM 7675 % | Fesoterodine % |
|---|---|---|---|
| EC 10 cP | 12.88 | 1.27 | 84.93 |
| Eudragit L | 4.87 | — | 95.02 |
| Eudragit NE 30D | 11.37 | 4.74 | 80.54 |

TABLE 14-continued

| Polymeric binder used in sample[1,2] (on lactose particles) | SPM 7605 % | SPM 7675 % | Fesoterodine % |
|---|---|---|---|
| Eudragit RS 30D | 11.83 | 4.74 | 79.41 |
| Eudragit RS PO | 18.50 | 3.33 | 73.50 |
| HPMC (1:19) | 0.97 | 0.18 | 98.36 |
| HPMC (1:9) | 1.68 | 0.40 | 97.53 |
| Kollicoat SR 30D | 9.47 | 1.09 | 86.05 |
| Kollidon SR | 8.42 | 0.75 | 88.02 |
| PVA | 1.82 | 1.03 | 96.62 |
| PVP | 7.11 | 0.29 | 90.77 |
| Xylitol (reference)[3] | 4.37 | 0.51 | 92.77 |

[1]All formulations were in a 1:9 wt % ratio of fesoterodine hydrogen fumarate:polymeric binder except where noted
[2]See Table 15 for specific details of the polymeric binders used.
[3]1:9 weight % of fesoterodine hydrogen fumarate:xylitol.

TABLE 15

| Polymeric binder | Compendial Name | Trade Name | Supplier |
|---|---|---|---|
| EC 10 cP | Ethylcellulose USP | Ethocel Std 10 | Dow |
| Eudragit L | Methacrylic Acid Copolymer, Type A NF | Eudragit L | Evonik |
| Eudragit NE 30D | Polyacrylate dispersion 30% | Eudragit NE 30D | Evonik |
| Eudragit RS 30D | Ammonio Methacrylate Copolymer Dispersion Type B | Eudragit RS 30D | Evonik |
| Eudragit RS PO | Ammonio Methacrylate Copolymer Type B NF | Eudragit RS PO | Evonik |
| HPMC (1:19) | Hypromellose USP | Methocel E5 | Dow |
| HPMC (1:9) | Hypromellose USP | Methocel E5 | Dow |
| Kollicoat SR 30D | Polyvinyl acetate dispersion USP | Kollicoat SR 30D | BASF |
| Kollidon SR | Polyvinyl acetate/polyvinylpyrrolidone | Kollidon SR | BASF |
| PVA | Polyvinyl alcohol USP | Mowiol 4-88 | Polysciences |
| PVP | Povidone USP | Kollidon 30 | BASF |
| Xylitol | Xylitol USP | Xylisorb 90 | Roquette | c) Results

It is clearly evident from Table 14 that of the polymeric binder samples analysed, only fesoterodine and HPMC samples (in ratios of either 1:19 or 1:9 wt. %) provided acceptable chemical stability as judged by the levels observed for the key SPM 7605 and SPM 7675 degradants when the samples as described were stored for 12 weeks at 40° C./75% R.H.

EXAMPLE 12

Comparative Chemical Stability of Tablets Containing Solid Molecular Dispersions of 1:19 or 1:9 Weight % Fesoterodine Hydrogen Fumarate:HPMC (Hypromellose) on Lactose Particles Versus the Commercial Xylitol-Based Tablet a) Sample Preparation The tablets containing the 1:19 and 1:9 HPMC dispersions on lactose were prepared as described in Example 10, steps (a), (b) and (c)

b) Stability Data

The analytical methodology employed for the determination of the degradation products SPM7605 and SPM7675 (see chemical structures in Example 8) in samples of fesoterodine hydrogen fumarate in HPMC dispersions on lactose was similar to that described in Example 9 with minor modifications to the HPLC conditions as described in Table 16.

TABLE 16

| Mobile phase A (MPA) | 0.1% trifluoroacetic acid (aq) | | | | |
|---|---|---|---|---|---|
| Mobile phase B (MPB) | 0.1% trifluoroacetic acid (far UV Acetonitrile) | | | | |
| Detector | UV absorbance at 220 nm | | | | |
| Injection Volume | TEST 75 µL | | | | |
| Column temperature | 35° C. | | | | |
| Auto sampler temperature | 10° C. | | | | |
| Flow Rate | 1.2 mL/min | | | | |
| Run Time | 45 minutes | | | | |
| Elution Mode | Gradient | | | | |
| | Time (min) | 0.0 | 39 | 39.1 | 41.0 | 45.0 |
| | MPA (%) | 74 | 74 | 50 | 50 | 74 |
| | MPB (%) | 26 | 26 | 50 | 50 | 26 |
| Column Stationary Phase | Spheribond CN 5 µm or Waters Spherisorb CN 5 µm or equivalent | | | | |

The comparative stability of tablets containing 1:19 or 1:9 HPMC dispersions on lactose versus the commercial xylitol-based tablet (8 mg strength) was assessed by storage of samples for 10 days at the purposefully selected, stressed (high temperature), storage conditions of 60° C./30% RH, 50° C./50% RH and 50° C./30% RH. The results are summarised in Tables 17, 18 and 19.

TABLE 17

Stability of fesoterodine hydrogen fumarate commercial xylitol-based 8 mg tablets stored at stressed conditions

| | | Condition | | |
|---|---|---|---|---|
| Degradation Products | Initial | 60° C./30% RH | 50° C./50% RH | 50° C./30% RH |
| | | Results | | |
| Time point | Initial | 3 d | 5 d | 5 d | 10 d | 10 d |
| SPM 7605% | 0.33 | 1.40 | 1.98 | 3.37 | 7.28 | 1.59 |
| SPM 7675% | 0.17 | 0.49 | 0.67 | 0.74 | 1.35 | 0.51 |
| Total % | 0.93 | 2.7 | 4.2 | 5.2 | 12.4 | 3.0 |

TABLE 18

Stability of tablets containing 1:9 wt % fesoterodine hydrogen fumarate:HPMC on lactose particles stored at stressed conditions

| | | Condition | | |
|---|---|---|---|---|
| Degradation Products | Initial | 60° C./30% RH | 50° C./50% RH | 50° C./30% RH |
| | | Results | | |
| Time point | Initial | 3 d | 5 d | 5 d | 10 d | 10 d |
| SPM 7605% | 0.22 | 1.22 | 1.69 | 1.45 | 2.37 | 1.48 |
| SPM 7675% | 0.10 | 0.26 | 0.35 | 0.29 | 0.29 | 0.34 |
| Total % | 1.2 | 2.3 | 5.1 | 4.3 | 4.3 | 4.1 |

TABLE 19

Stability of tablets containing 1:19 wt %
fesoterodine hydrogen fumarate:HPMC
on lactose particles stored at stressed conditions

| | | Condition | | | |
|---|---|---|---|---|---|
| Degradation Products | Initial | 60° C./ 30% RH | 50° C./ 50% RH | | 50° C./ 30% RH |
| | | Results | | | |
| Time point | Initial | 3 d | 5 d | 5 d | 10 d | 10 d |
| SPM 7605% | 0.16% | 0.66 | 0.92 | 0.77 | 1.28 | 0.82 |
| SPM 7675% | 0.12% | 0.15 | 0.18 | 0.14 | 0.19 | 0.15 |
| Total % | 1.4% | 2.1 | 2.1 | 1.7 | 2.4 | 3.0 |

It is clearly evident from Tables 17, 18 and 19 that the levels of SPM 7605 and SPM 7675 in tablets containing 1:9 or 1:19 wt % fesoterodine hydrogen fumarate:HPMC on lactose particles were less than levels observed for the commercial xylitol-based tablet under all three storage conditions used.

Analysis

1. Analysis of IR Layer of IR and MR Beads Comprising a Solid Molecular Dispersion of Fesoterodine Hydrogen Fumarate and HPMC (Hypromellose) on Microcrystalline Cellulose Beads by Fourier Transform Infrared (FTIR) Spectroscopy IR and MR Bead Sample Preparation (a) IR Beads (see Examples 2 and 3)

The beads were cut in half with a scalpel after which the IR layer was peeled off using a scalpel and tweezers. The peeled off IR layers were lightly pressed down onto a glass slide with a glass cover slip, after which they were transferred to the Attenuated Total Reflection (ATR) window for analysis. IR layers of five or six half beads were used for the collection of one spectrum.

(b) MR Beads (see Examples 4 and 6)

The beads were cut in half with a scalpel after which the MR layer was peeled off using a scalpel and tweezers. Then the IR layer was peeled off. The peeled off IR layers were lightly pressed down onto a glass slide with a glass cover slip, after which they were transferred to the ATR window for analysis. For the 20% MR coated beads (see Example 6), IR layers of one or two half beads were used for the collection of one spectrum. For the 10% MR coated beads (see Example 4), IR layers of five half beads were used for the collection of one spectrum.

Crystalline Fesoterodine Hydrogen Fumarate Reference

This was obtained by the method described in U.S. Pat. No. 6,858,650 B1, Preparation 6.

Preparation of Amorphous Fesoterodine Hydrogen Fumarate Reference

Crystalline fesoterodine hydrogen fumarate (see above) was cryogenically ball milled using a Retsch MM301 mill and 1.5 mL Retsch stainless steel mill chamber and ball. Each milling session lasted 10 minutes and the mill speed was set at 30 Hz. The mill chamber with sample inside was cooled in liquid nitrogen for 5 minutes before milling, and between each subsequent milling session. The sample was milled for 50 minutes in total, after which a PXRD pattern was collected to confirm that the sample was amorphous fesoterodine hydrogen fumarate.

FTIR

The infrared spectra were acquired using a ThermoNicolet Nexus FTIR spectrometer equipped with a 'DurasampIIR' single reflection ATR accessory (diamond surface on zinc selenide substrate) and d-TGS KBr detector. The spectra were collected at 2 $cm^{-1}$ resolution and a co-addition of 512 scans. Happ-Genzel apodization was used. Using ATR FTIR will cause the relative intensities of infrared bands to differ from those seen in a transmission FTIR spectrum using KBr disc or nujol mull sample preparations. Due to the nature of ATR FTIR, the bands at lower wavenumber are more intense than those at higher wavenumber.

FTIR Data Treatment

Spectra were transferred into absorbance units within the ThermoNicolet Omnic 6.1a software Results FIGS. 2-5a inclusive show the FTIR ATR spectra obtained for

- crystalline fesoterodine hydrogen fumarate
- amorphous fesoterodine hydrogen fumarate
- IR layer of IR beads comprising a solid molecular dispersion of fesoterodine hydrogen fumarate and hypromellose (see Example 2 or 3)
- IR layer of 10% MR beads comprising a solid molecular dispersion of fesoterodine hydrogen fumarate and hypromellose (see Example 4)
- IR layer of 20% MR beads comprising a solid molecular dispersion of fesoterodine hydrogen fumarate and hypromellose (see Example 6)

The results show that

- when assessing infrared peak frequency positions and intensities obtained by analysis of the IR layers of IR and MR beads, there are peaks that overlap with the peaks seen for amorphous fesoterodine fumarate as well as those seen for crystalline fesoterodine hydrogen fumarate, and there are peaks with different frequency positions and intensities that can be used to characterise the IR layers of IR and MR beads, amorphous fesoterodine fumarate and crystalline fesoterodine hydrogen fumarate.
- in the spectra obtained from the samples of the IR layers of IR and MR beads, the absence of some of the more intense, characteristic peaks observed in the spectra obtained from samples of crystalline fesoterodine hydrogen fumarate and amorphous fesoterodine hydrogen fumarate.
- there are obvious changes in relative intensities of peaks in the spectra obtained from the samples of the IR layers of IR and MR beads in comparison to the peaks in the spectra obtained from samples of crystalline fesoterodine hydrogen fumarate and amorphous fesoterodine hydrogen fumarate.

Without being bound by theory, it is believed that these changes in peak frequency position and intensity observed show that there is a clear interaction of fesoterodine hydrogen fumarate with the HPMC polymeric binder in the IR layers of IR and MR beads. These effects are similar to those described by Konno and Taylor, J. Pharm. Sci (2006) 95, 12, 2692-2705. These effects are believed to be caused by the presence of a solid molecular dispersion of fesoterodine hydrogen fumarate in the HPMC polymeric binder in the IR layers of the IR and MR beads analysed. In other words it is believed that neither amorphous molecular clusters, nor crystals, of fesoterodine hydrogen fumarate in the HPMC polymeric binder could be detected in the IR layers of the IR and MR beads analysed.

2. Analysis of IR Granules Comprising a Solid Molecular Dispersion of FESOTERODINE HYDROGEN FUMARATE and HPMC (Hypromellose) on Lactose Particles by Fourier Transform Infrared (FTIR) Spectroscopy The IR granules were prepared as described in Examples 10a and 10b.

Sample Preparation

No sample preparation was performed. The sample was placed onto the ATR crystal and pressure was applied.

FTIR

The infrared spectra were acquired using a ThermoNicolet Nexus FTIR spectrometer equipped with a 'DurasampIIR' single reflection ATR (attenuated total reflection) accessory (diamond surface on zinc selenide substrate) and d-TGS KBr detector. The reference spectra for crystalline and amorphous fesoterodine hydrogen fumarate, HPMC (Methocel E5LV) and lactose (Pharmatose—trade mark) were collected using the following experimental settings:

| Sample | No scans | Resolution (cm$^{-1}$) |
| --- | --- | --- |
| Crystalline fesoterodine hydrogen fumarate | 128 | 4 |
| Amorphous fesoterodine hydrogen fumarate | 256 | 4 |
| HPMC (Methocel E5LV) | 128 | 4 |
| Lactose (Pharmatose 110 mesh) | 64 | 4 |

For the sample containing a solid molecular dispersion of 1:9 weight % fesoterodine hydrogen fumarate/HPMC on lactose particles the spectra were collected at 4 cm$^{-1}$ resolution and a co-addition of 512 scans.

For the sample containing a solid molecular dispersion of 1:19 weight % fesoterodine hydrogen fumarate/HPMC on lactose particles the spectra were collected at 8 cm$^{-1}$ resolution and a co-addition of 512 scans.

Happ-Genzel apodization was used. Using ATR FT-IR will cause the relative intensities of infrared bands to differ from those seen in a transmission FT-IR spectrum using KBr disc or nujol mull sample preparations. Due to the nature of ATR FT-IR, the bands at lower wavenumber are more intense than those at higher wavenumber.

The FTIR spectra obtained are shown In FIGS. 6, 6a, 6b, 7, 7a, 8 and 8a.

FTIR Data Treatment

Spectra were transferred into absorbance units within ThermoNicolet Omnic 6.1a software and saved as .spc files. The spectra were then opened in Grams/A1 8.0 where a peak fit was performed using 4 peaks in the region 1792 cm$^{-1}$ to 1521 cm$^{-1}$, using a mixture of Gaussian/Lorentzian peak shape and 50 iterations for the fit.

Evidence for the Presence of a Solid Molecular Dispersion Rather than a Physical Mixture of Amorphous or Crystalline Domains in a Matrix.

When assessing infrared peak positions for the samples containing a solid dispersion of fesoterodine hydrogen fumarate/HPMC on lactose particles there are peaks that overlap with those for amorphous fesoterodine hydrogen fumarate as well as those for crystalline fesoterodine hydrogen fumarate.

However, the absence of some of the more intense, characteristic peaks seen for the amorphous and crystalline fesoterodine hydrogen fumarate samples in the spectra for the fesoterodine hydrogen fumarate/HPMC on lactose particle samples analysed, as well as the obvious changes in relative intensities and shifts compared to the amorphous and crystalline fesoterodine hydrogen fumarate samples, allows a conclusion that there is a clear interaction of the fesoterodine hydrogen fumarate with the HPMC matrix in the fesoterodine hydrogen fumarate/HPMC on lactose particle samples. This interaction causes typical shifts in the infrared frequencies of certain functional groups, as described in the literature by Konno and Taylor, J. Pharm. Sci, 95, 12, 2692-2705 (2006). Therefore we can conclude that fesoterodine hydrogen fumarate is present in the fesoterodine hydrogen fumarate/HPMC on lactose particle samples as a solid molecular dispersion.

3. Analysis of IR Granules Comprising Fesoterodine Hydrogen Fumarate and Either PVA or Methyl Methacrylate (Eudragit) on Lactose Particles by Fourier Transform Infrared (FTIR) Spectroscopy and PXRD

PXRD

Capillary PXRD data was collected on the samples of fesoterodine hydrogen fumarate and either PVA or methyl methacrylate (Eudragit NE 30D or Eudragit RS PO) on lactose particles prepared as in Example 11.

PXRD data was collected using a Bruker-AXS Ltd D8 Advance powder X-ray diffractometer fitted with a capillary stage, a theta-theta goniometer, a KA-1 (Cu) primary monochromator and a Braun position sensitive detector. The sample was mounted in a 1.0 or 1.5 mm quartz capillary. The sample was rotated whilst being irradiated with copper K-alpha1 X-rays (wavelength=1.5406 Ångstroms) with the X-ray tube operated at 40 kV/40 mA. The analysis was performed with the goniometer running in continuous mode set for a 6 second count per 0.011° step over a two theta range of 2 to 55°.

The patterns that were collected show no evidence for crystalline fesoterodine hydrogen fumarate in the samples. It would have been expected that PXRD would be capable of detecting crystalline fesoterodine hydrogen fumarate at the API concentration levels (ca. 5% w/w %) in these samples and hence it is concluded that the samples analysed did not contain crystalline fesoterodine hydrogen fumarate.

FTIR

FTIR ATR analysis was carried out on the above samples of fesoterodine hydrogen fumarate and either PVA or methyl methacrylate (Eudragit) on lactose particles in an attempt to determine if the fesoterodine hydrogen fumarate was present in either an amorphous state or as a solid molecular dispersion with the polymeric binder used.

The region of the spectra where important information on characteristic fesoterodine hydrogen fumarate functional groups is obtained spans from 1800-1500 cm$^{-1}$.

Unfortunately methyl methacrylate (Eudragit) itself displays a very intense peak around 1724 cm$^{-1}$ that masks several characteristic fesoterodine hydrogen fumarate peaks leaving only one observable characteristic fesoterodine hydrogen fumarate peak around 1581 cm$^{-1}$. Unfortunately this peak is not effective alone in distinguishing the existence of fesoterodine hydrogen fumarate in an amorphous state from the existence of fesoterodine hydrogen fumarate in solid molecular dispersion in the sample of fesoterodine hydrogen fumarate and methyl methacrylate (Eudragit) on lactose particles.

For the sample of fesoterodine hydrogen fumarate and PVA on lactose particles, FTIR ATR analysis showed that there are dominant PVA peaks ranging from 1731-1568 cm$^{-1}$ leaving no clear region to assess peaks characteristic of fesoterodine hydrogen fumarate and to distinguish the existence of fesoterodine hydrogen fumarate in an amorphous state from the existence of fesoterodine hydrogen fumarate in solid molecular dispersion in the sample of fesoterodine hydrogen fumarate and PVA on lactose particles.

In summary, despite use of best efforts, it could not be determined if the samples of fesoterodine hydrogen fumarate and either PVA or methyl methacrylate (Eudragit) on lactose particles contained fesoterodine hydrogen fumarate in an amorphous state or fesoterodine hydrogen fumarate in a solid molecular dispersion.

The invention claimed is:

1. A solid molecular dispersion comprising from 3:97 to 12:88 weight % ratio of fesoterodine hydrogen fumarate to a polymeric binder selected from the group consisting of an alkyl hydroxyalkylcellulose ether, a hydroxyalkylcellulose ether, an ester of either thereof, and a mixture of any two or more thereof.

2. The dispersion as claimed in claim 1 comprising about a 1:9 weight % ratio of fesoterodine hydrogen fumarate to a polymeric binder selected from the group consisting of an alkyl hydroxyalkylcellulose ether, a hydroxyalkylcellulose ether, an ester of either thereof, and a mixture of any two or more thereof.

3. The dispersion as claimed in claim 2 consisting essentially of fesoterodine hydrogen fumarate and a polymeric binder selected from the group consisting of an alkyl hydroxyalkylcellulose ether, a hydroxyalkylcellulose ether, an ester of either thereof, and a mixture of any two or more thereof.

4. The dispersion as claimed in claim 1 consisting essentially of about a 1:9 weight % ratio of fesoterodine hydrogen fumarate to a polymeric binder selected from the group consisting of an alkyl hydroxyalkylcellulose ether, a hydroxyalkylcellulose ether, an ester of either thereof, and a mixture of any two or more thereof.

5. The dispersion as claimed in claim 1 wherein the polymeric binder is a cellulose ether selected from the group consisting of hydroxypropyl methyl cellulose (HPMC), hydroxyethyl methyl cellulose (HEMC), hydroxybutyl methyl cellulose (HBMC), hydroxyethylcellulose (HEC), hydroxypropyl cellulose (HPC), hydroxypropyl methyl cellulose acetate succinate (HPMCAS) and a mixture of any two or more thereof.

6. The dispersion as claimed in claim 5 wherein the cellulose ether component is hydroxypropyl methyl cellulose.

7. A method for treating urinary incontinence comprising administering to a patient in need thereof a therapeutically effective amount of the dispersion as claimed in claim 1.

8. An inert core bead or particle which is coated with a dispersion as claimed in claim 1.

9. The inert core bead or particle as claimed in claim 8 wherein the core bead or particle comprises microcrystalline cellulose.

10. A pharmaceutical tablet formulation comprising an inert core bead or particle as claimed in claim 9.

11. The inert core bead or particle as claimed in claim 9 which is further coated with a modified-release layer.

12. The inert core bead or particle as claimed in claim 11 wherein the modified release layer comprises ethyl cellulose and hydroxypropyl cellulose.

13. A pharmaceutical formulation comprising modified-release beads as claimed in claim 11.

14. The formulation as claimed in claim 13 wherein the modified-release beads are encapsulated.

15. A method of treating urinary incontinence comprising administering to a patient in need thereof a therapeutically effective amount of a formulation as claimed in claim 13.

16. The inert core bead or particle as claimed in claim 8 wherein the core bead or particle comprises lactose.

17. A pharmaceutical tablet formulation comprising an inert core bead or particle as claimed in claim 16.

18. A method of treating urinary incontinence comprising administering to a patient in need thereof a therapeutically effective amount of the inert core bead or particle of claim 8.

19. A dispersion as claimed in claim 1, comprising about a 1:19 weight % ratio of fesoterodine hydrogen fumarate to a polymeric binder selected from the group consisting of an alkyl hydroxyalkylcellulose ether, a hydroxyalkylcellulose ether, an ester of either thereof, and a mixture of any two or more thereof.

20. A dispersion as claimed in claim 19 consisting essentially of about a 1:19 weight % ratio of fesoterodine hydrogen fumarate to a polymeric binder selected from the group consisting of an alkyl hydroxyalkylcellulose ether, a hydroxyalkylcellulose ether, an ester of either thereof, and a mixture of any two or more thereof.

21. A solid dispersion comprising from 3:97 to 12:88 weight % ratio of fesoterodine hydrogen fumarate to a polymeric binder selected from the group consisting of an alkyl hydroxyalkylcellulose ether, a hydroxyalkylcellulose ether, an ester of either thereof, and a mixture of any two or more thereof, in which the fesoterodine hydrogen fumarate is stabilized in the dispersion in a form not corresponding to its crystalline or amorphous form.

22. The solid dispersion of claim 21 which displays the FTIR characteristics shown in FIG. 3, 3A, 4, 4A, 5, 5A, 7, 7A, 8 or 8A.

23. The dispersion as claimed in claim 21 comprising about a 1:9 weight % ratio of fesoterodine hydrogen fumarate to a polymeric binder selected from the group consisting of an alkyl hydroxyalkylcellulose ether, a hydroxyalkylcellulose ether, an ester of either thereof, and a mixture of any two or more thereof.

24. The dispersion as claimed in claim 23 consisting essentially of fesoterodine hydrogen fumarate and a polymeric binder selected from the group consisting of an alkyl hydroxyalkylcellulose ether, a hydroxyalkylcellulose ether, an ester of either thereof, and a mixture of any two or more thereof.

25. A dispersion as claimed in claim 21, comprising about a 1:19 weight % ratio of fesoterodine hydrogen fumarate to a polymeric binder selected from the group consisting of an alkyl hydroxyalkylcellulose ether, a hydroxyalkylcellulose ether, an ester of either thereof, and a mixture of any two or more thereof.

26. A dispersion as claimed in claim 25 consisting essentially of about a 1:19 weight % ratio of fesoterodine hydrogen fumarate to a polymeric binder selected from the group consisting of an alkyl hydroxyalkylcellulose ether, a hydroxyalkylcellulose ether, an ester of either thereof, and a mixture of any two or more thereof.

27. The dispersion as claimed in claim 21 consisting essentially of about a 1:9 weight % ratio of fesoterodine hydrogen fumarate to a polymeric binder selected from the group consisting of an alkyl hydroxyalkylcellulose ether, a hydroxyalkylcellulose ether, an ester of either thereof, and a mixture of any two or more thereof.

28. The dispersion as claimed in claim 21 wherein the polymeric binder is a cellulose ether selected from the group consisting of hydroxypropyl methyl cellulose (HPMC), hydroxyethyl methyl cellulose (HEMC), hydroxybutyl methyl cellulose (HBMC), hydroxyethylcellulose (HEC), hydroxypropyl cellulose (HPC), hydroxypropyl methyl cellulose acetate succinate (HPMCAS) and a mixture of any two or more thereof.

29. An inert core bead or particle which is coated with a dispersion as claimed in claim 21.

30. The inert core bead or particle as claimed in claim 29 wherein the core bead or particle comprises microcrystalline cellulose.

31. A pharmaceutical tablet formulation comprising an inert core bead or particle as claimed in claim 30.

32. The inert core bead or particle as claimed in claim 29 wherein the core bead or particle comprises lactose.

33. A pharmaceutical tablet formulation comprising an inert core bead or particle as claimed in claim 32.

34. A process for the preparation of a solid molecular dispersion, comprising:
  (a) preparing a solution comprising fesoterodine hydrogen fumarate and a polymeric binder selected from the group consisting of an alkyl hydroxyalkylcellulose ether or a hydroxyalkylcellulose ether, a hydroxyalkylcellulose ether, an ester of either thereof, and a mixture of any two or more thereof, in from 3:97 to 12:88 weight % ratio, and
  (b) drying the solution to form said dispersion.

* * * * *